(12) United States Patent
Pellicciari et al.

(10) Patent No.: US 11,066,437 B2
(45) Date of Patent: Jul. 20, 2021

(54) METHODS AND INTERMEDIATES FOR THE PREPARATION OF BILE ACID DERIVATIVES

(71) Applicant: Intercept Pharmaceuticals, Inc., New York, NY (US)

(72) Inventors: Roberto Pellicciari, Perugia (IT); Antimo Gioiello, Perugia (IT); Gabriel Galvin, San Diego, CA (US); Ronald D. Lewis, II, San Diego, CA (US); Mathew Yanik, San Diego, CA (US); Myoung Goo Kim, Summerfield, NC (US); Frederik Ronald Leusink, Zuidhorn (NL); Bartjan Koning, Aduard (NL); Thomas Hensel, Groningen (NL)

(73) Assignee: Intercept Pharmaceuticals, Inc., New York, NY (US)

( * ) Notice: Subject to any disclaimer, the term of this patent is extended or adjusted under 35 U.S.C. 154(b) by 0 days.

(21) Appl. No.: 16/016,486

(22) Filed: Jun. 22, 2018

(65) Prior Publication Data

US 2018/0371009 A1 Dec. 27, 2018

Related U.S. Application Data

(60) Provisional application No. 62/523,937, filed on Jun. 23, 2017.

(51) Int. Cl.
*C07J 9/00* (2006.01)
*C07J 31/00* (2006.01)

(52) U.S. Cl.
CPC ............. *C07J 9/005* (2013.01); *C07J 31/006* (2013.01)

(58) Field of Classification Search
CPC ................................ C07J 9/005; C07J 31/006
See application file for complete search history.

(56) References Cited

U.S. PATENT DOCUMENTS

| 2,554,882 | A | 5/1951 | Reichstein |
| 3,277,121 | A | 10/1966 | Bharucha et al. |
| 9,611,289 | B2 | 4/2017 | Pellicciari |
| 2016/0130297 | A1 | 5/2016 | Or et al. |
| 2016/0145295 | A1 | 5/2016 | Or et al. |
| 2016/0145296 | A1 | 5/2016 | Or et al. |

(Continued)

FOREIGN PATENT DOCUMENTS

| DE | 30 40 634 A1 | 5/1982 |
| WO | WO 2002/075298 A2 | 9/2002 |

(Continued)

OTHER PUBLICATIONS

Reich et al, Helvetica Chimica Acta, Bile acids and related substances. XXII. 11(a)-Keto-and 11(a)-hydroxycholanic acids,1943, 26, pp. 562-585. (Year: 1943).*

(Continued)

*Primary Examiner* — Paul A Zucker
(74) *Attorney, Agent, or Firm* — Cooley LLP; Ivor R. Elrifi; Chen Chen

(57) ABSTRACT

The present disclosure relates to methods and novel intermediates useful in the preparation of a compound of formula I

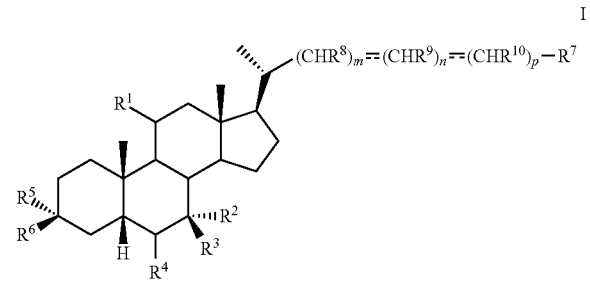

or pharmaceutically acceptable salt, hydrate, solvate or amino acid, sulfate or glucuronide conjugate, or prodrug thereof, comprising the step of reacting a compound of formula I-4 with a halogenating reagent to provide a compound of formula I-5a

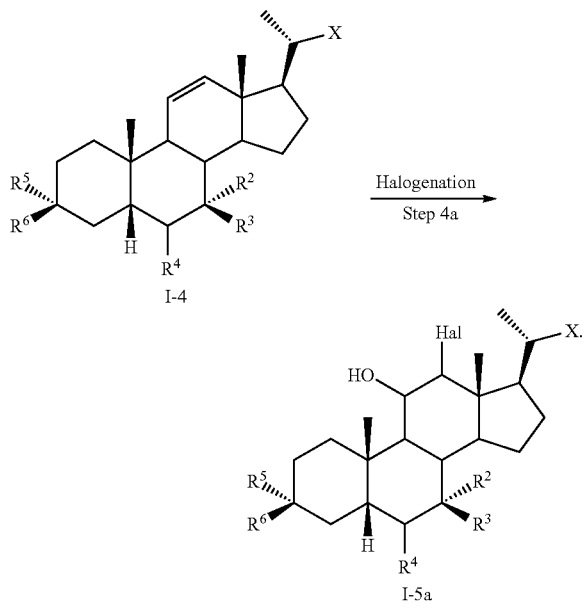

22 Claims, No Drawings

(56) References Cited

U.S. PATENT DOCUMENTS

| | | | |
|---|---|---|---|
| 2016/0185815 | A1 | 6/2016 | Wang et al. |
| 2016/0229886 | A1 | 8/2016 | Shen et al. |
| 2016/0289262 | A1 | 10/2016 | Wang et al. |
| 2017/0136040 | A1 | 5/2017 | Moriarty et al. |

FOREIGN PATENT DOCUMENTS

| | | | |
|---|---|---|---|
| WO | WO 2014/184271 | A1 | 11/2014 |
| WO | WO 2017/027396 | A1 | 2/2017 |
| WO | WO 2017/062763 | A1 | 4/2017 |
| WO | WO 2018/081285 | A1 | 5/2018 |

OTHER PUBLICATIONS

Reddy et al, Helvetica Chimica Acta, N-Iodosuccinimide: A Highly Effective Regioselective Reagent for Iodoesterification of Alkenes, 2013, 96, pp. 1313-1324. (Year: 2013).*
Constantin J. et al., "Introduction of the 11-Keto Function in the Steroids", J. Am. Chem. Soc. (1952), vol. 74, p. 3908-3910.
Fieser L. et al., "The Conversion of Cholic Acid into 3α-Hydroxy-12-keto-$\Delta^{9(11)}$-cholenic Acid", J. Am. Chem. Soc. (1951), vol. 73, p. 4133-4135.
Fristad W. et al., "Silanes in Organic Synthesis. 9. Enesilylation as a Method for 1,2-Carbonyl Migration within Ketones and for Conversion to 1,2-Transposed Allylic Alcohols", J. Org. Chem. (1980), vol. 45, p. 3028-3037.
GenBank Accession No. NM 021745.1, "Rattus norvegicus nuclear receptor subfamily 1, group H, member 4 (Nr1h4), mRNA", (2018), 5 pages.
GenBank Accession No. NM 009108, "Mus musculus nuclear receptor subfamily 1, group H, member 4 (Nr1h4), transcript variant 3, mRNA", (2018), 5 pages.
GenBank Accession No. NM 005123, "*Homo sapiens* nuclear receptor subfamily 1 group H member 4 (NR1H4), transcript variant 2, mRNA", (2018), 5 pages.
Gioiello A. et al., "Bile Acid Derivatives as Ligands of the Farnesoid X Receptor: Molecular Determinants for Bile Acid Binding and Receptor Modulation", Current Topics in Medicinal Chemistry, (2014), vol. 14, p. 2159-2174.
Hassner A. et al., "Transposition of Ketones via 2-Nitro Ketones", J. Org. Chem. (1968), vol. 33, No. 5, p. 1733-1739.
Hicks et al. "Improved Methods for the Preparation of 3(α)-Hydroxy-$\Delta^{9,11}$-Cholenic Acid", J. Biol. Chem. (1945), p. 633-640.
Hicks et al. "The Introduction of Oxygen into the Steroid Nucleus at the $C_{11}$ Position", J. Biol. Chem. (1945), p. 641-644.

Huber et al. "Generation of multiple farnesoid-X receptor isoforms through the use if alternative promoters", Gene (2002), vol. 290, p. 35-43.
Ishida et al. "Study on the Bile Salts from Sunfish, *Mola mola* L. I. The Structures of Sodium Cyprinol Sulfates, the Sodium Salt of a New Bile Acid Conjugated with Taurine, and a New Bile Alcohol and Its New Sodium Sulfates", Chem Pharm Bull (1998), vol. 46, p. 12-16.
Kaspersen F. et al., "A review of the methods of chemical synthesis of sulphate and glucuronide conjugates", Xenobiotica (1987), vol. 17, No. 12, p. 1451-1471.
Marshall J. et al. "A Nonoxidative Method for Ketone Transposition" J. Org. Chem. (1969), vol. 34, p. 4188-4199.
Mostarda S. et al. "Glucuronidation of bile acids under flow conditions: design of experiments and Koenigs-Knorr reaction optimization", Organic & Biomolecular Chemistry, (2014), vol. 12, p. 9592-9600.
Paquette L. et al., "Silanes in Organic Synthesis. 8. Preparation of Vinylsilanes from Ketones and Their Regiospecific Cyclopentenone Annulation", J. Org. Chem. (1980), vol. 45, No. 15, p. 3017-3037.
Pellicciari R. et al., "Discovery of 3α,7α,11β-Trihydroxy-6α-ethyl-5β-cholan-24-oic Acid (TC-100), a Novel Bile Acid as Potent and Highly Selective FXR Agonist for Enterohepatic Disorders", Journla of Medicinal Chemistry (2016), vol. 59, p. 9201-9214.
Ritter "Roles of glucuronidation and UDP-glucuronosyltransferases in xenobiotic bioactivation reactions", Chemico-Biological Interactions (2000), vol. 129, p. 171-193.
Stachulski A. et al. "Acyl Glucuronides: Biological Activity, Chemical Reactivity, and Chemical Synthesis", J. Med. Chem. (2006), vol. 49, p. 6931-6945.
Stachulski A. et al. "The synthesis of O-glucuronides", Nat. Prod. Rep. (1998), vol. 15, p. 173-186.
Stork G. et al. "Simple Preparation of a Useful C/D-Ring Fragment for the Construction of 11-Keto Steroids", Tetrahedron Letters (1984), vol. 25, p. 5367-5370.
Ott et al. "Uber Gal lensauren und verwandte Stoffe. 27. Mitteilung. [alpha]-Oxyde der beiden 3-Oxy- und der 3-Keto-cholen-(11)-saure", Helvetica Chimica Acta, vol. 26, No. 6, 1943, pp. 1799-1815. (English description provided).
Lardon et al. "Uber Gallensauren und verwandte Stoffe. 35. Mitteilung1). 3[alpha]-Acetoxy-nor-, bisnor- und -atio-cholen-(9)-saure-methylester", Helvetica Chimica Acta, vol. 28, No. 1, 1945, pp. 1420-1426. (English description provided).
Sarett, L. "Partial Synthesis of Pregnene-4-Triol-17(beta),20(beta),21-Dione-3, 11 and Pregnene-4-Diol-17(beta),21-Trione-3,11, 20 Monoacetate", Journal of Biological Chemistry, vol. 162, No. 3, 1946, pp. 601-631.

* cited by examiner

METHODS AND INTERMEDIATES FOR THE PREPARATION OF BILE ACID DERIVATIVES

BACKGROUND

Bile acids (BAs) and their derivatives have been shown to modulate farnesoid X receptor (FXR) and regulate FXR-mediated diseases and conditions (Gioiello, et al., Curr. Top. Med. Chem. 14 (2014), 2159). Such natural bile acids such as chenodeoxycholic acid (CDCA), deoxycholic acid (DCA), lithocholic acid (LCA), and the taurine and glycine conjugates thereof are known FXR ligands. A semi-synthetic bile acid analogue, 3α,7α-dihydroxy-6α-ethyl-5β-cholan-24-oic acid (6-ethyl-chenodeoxycholic acid (6-ECDCA) or obeticholic acid (OCA)), disclosed in WO 2002/75298 is a highly potent FXR modulator, which is currently marketed as OCALIVA® for the treatment of primary biliary cholangitis (PBC). Another semi-synthetic bile acid analog, 3α,7α,11β-trihydroxy-6α-ethyl-5β-cholan-24-oic acid (compound 100) while being a potent FXR agonist, also showed specificity against G protein-coupled receptor TGR5 (GPBAR1, M-BAR, GPBAR, or GPR131).

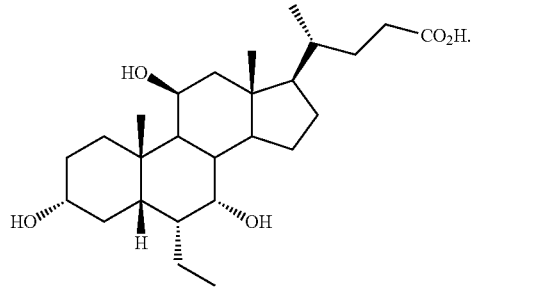

100

Identification of potent and selective bile acid-based FXR agonists is fundamental not only to further explore the physiological roles and pathological implications of bile acid signaling, but also to advance novel therapeutic opportunities associated with the selective modulation of the receptors by bile acid analogs. More efficacious and selective bile acid-based FXR agonists may demonstrate added therapeutic value by avoiding potential side effects associated with TGR5 activation (e.g., itching, gallbladder filling, and cholesterol gallstone formation) (Pellicciari et al., J. Med. Chem. 59 (2016), 9201-9214).

Methods of synthesizing compound 100 and its analogs have been described in WO 2014/184271 and more recently in WO 2017/062763. However, there remains a need for more efficient methods of preparing selective FXR modulators, such as compound 100 and its analogs, including processes with a reduced number of steps, increased yields, and providing high purity of intermediates and final products. The present application addresses this need.

SUMMARY OF THE INVENTION

The present invention provides methods of preparing bile acid derivatives.

In one aspect, the present invention relates to a method of preparing a compound of formula I

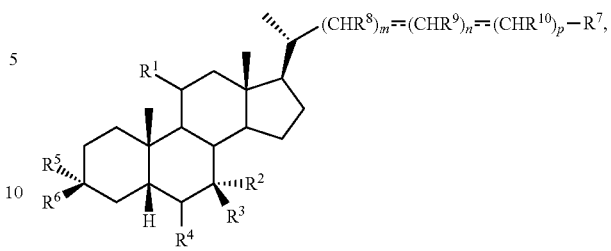

I or a pharmaceutically acceptable salt, solvate, or amino acid, sulfate or glucuronide conjugate or prodrug thereof, wherein:
$R^1$, $R^2$, $R^2$, $R^3$, $R^4$, $R^5$, $R^6$, $R^7$, $R^8$, $R^9$, $R^{10}$, m, n, and p are as described herein.

In another aspect, the present disclosure relates to a method of preparing a compound of formula II:

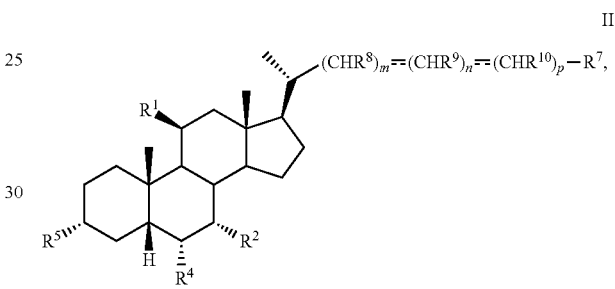

II or a pharmaceutically acceptable salt, solvate, or amino acid, sulfate or glucuronide conjugate or prodrug thereof, wherein:
$R^1$, $R^2$, $R^4$, $R^5$, $R^7$, $R^8$, $R^9$, $R^{10}$, m, n, and p are as described herein.

In another aspect, the present disclosure relates to a method of preparing a compound of formula III:

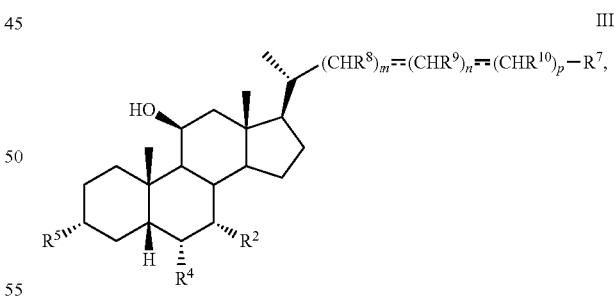

III or a pharmaceutically acceptable salt, solvate, or amino acid, sulfate or glucuronide conjugate or prodrug thereof, wherein:
$R^1$, $R^2$, $R^4$, $R^5$, $R^7$, $R^8$, $R^9$, $R^{10}$, m, n, and p are as described herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. The materials, methods, and examples are illustrative only and are not intended to be limiting. In the case of conflict, the present specification, including definitions, will control. In the specification, the singular forms also include the plural unless the context clearly dictates otherwise. All publications, patent applications, patents, and other references mentioned herein are incorporated by reference. The references cited herein are not admitted to be prior art to the claimed invention.

Other features and advantages of the invention will be apparent from the following detailed description.

DETAILED DESCRIPTION

Definitions

Certain terms used in the specification and claims are collected here.

As used herein, the phrase "a compound of the disclosure" refers to a compound of any one of formula I, Ia, Ib, I-9, II, III, IIIa, IIIb, C2, D5, 44, 44a, 45, and 100 or any other compound explicitly disclosed herein.

The term "$C_1$-$C_6$ alkyl" or "Alk" or "alkyl", as used herein, refers to a straight-chain or branched hydrocarbon moiety having 1, 2, 3, 4, 5, or 6 carbon atoms. Examples of $C_1$-$C_6$ alkyl moieties include, but are not limited to, methyl, ethyl, n-propyl, isopropyl, cyclopropyl, n-butyl, isobutyl, sec-butyl, t-butyl, n-pentyl, isopentyl, and n-hexyl. "$C_1$-$C_4$ alkyl" refers to a straight-chain or branched hydrocarbon moiety having 1, 2, 3, or 4 carbon atoms.

The term "alkenyl" refers to a straight-chain or branched hydrocarbon moiety containing at least one carbon-carbon double bond. Both the trans and cis isomers of the carbon-carbon double bond are encompassed under the term "alkenyl". Examples of alkenyl moieties include, but are not limited to, vinyl, allyl, 1-butenyl, 2-butenyl, 3-butenyl, and 2-hexenyl.

As used herein, "alkynyl" refers to a straight-chain or branched hydrocarbon moiety containing at least one carbon-carbon triple bond. Examples of alkynyl moieties include, but are not limited to, ethynyl, 2-propynyl, 5-but-1-en-3-ynyl, and 3-hexynyl.

The term "alkoxy" refers to a straight-chain or branched saturated hydrocarbon covalently attached to an oxygen atom. Examples of alkoxy moieties include, but are not limited to, methoxy, ethoxy, isopropyloxy, n-propoxy, n-butoxy, t-butoxy, and pentoxy.

As used herein, the term "halogen" or "Hal" refers to fluorine, bromine, chlorine, and iodine.

As used herein, "carbocycle", "carbocyclic", or "carbocyclic ring" is intended to include any stable monocyclic or bicyclic ring having the specified number of carbons, any of which may be saturated, unsaturated, or aromatic. Carbocyclic ring includes cycloalkyl and aryl. For example, a $C_3$-$C_8$ carbocyclic ring is intended to include a monocyclic or bicyclic ring having 3, 4, 5, 6, 7, or 8 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, and phenyl.

As used herein, "heterocycle", "heterocyclic", or "heterocyclic group" includes any ring structure (saturated, unsaturated, or aromatic) which contains at least one ring heteroatom (e.g., N, O or S). Heterocycle includes heterocycloalkyl and heteroaryl. Examples of heterocycles include, but are not limited to, morpholine, pyrrolidine, tetrahydrothiophene, piperidine, piperazine, oxetane, pyran, tetrahydropyran, azetidine, and tetrahydrofuran. Examples of heterocyclic groups include, but are not limited to, benzimidazolyl, benzofuranyl, benzothiofuranyl, tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isoindazolyl, isoindolinyl, isoindolyl, isoquinolinyl, isothiazolyl, isoxazolyl, methylenedioxyphenyl, morpholinyl, pyridinyl, pyridyl, and pyrimidinyl.

As used herein, the term "cycloalkyl" refers to a saturated or unsaturated nonaromatic hydrocarbon mono- or multiring (e.g., fused, bridged, or spiro rings) system having 3 to 10 carbon atoms (e.g., $C_3$-$C_6$). Examples of cycloalkyl include, but are not limited to, cyclopropyl, cyclobutyl, cyclopentyl, cyclohexyl, cycloheptyl, cyclooctyl, cyclopentenyl, cyclohexenyl, and cycloheptenyl.

As used herein, any recited moiety which includes, but is not limited to, alkyl, alkenyl, alkynyl, alkoxy, carbocyclic ring, heterocyclic ring, cycloalkyl, etc. can be optionally substituted. The term "optionally substituted" refers to the indicated moiety which may or may not be substituted, and when substituted is mono-, di-, or tri-substituted, such as with 1, 2, or 3 substituents. In some instances, the substituent is halogen or OH.

As used herein, the term "protecting group" refers to an appropriate moiety for masking, for example, a hydroxyl functionality, which is stable/non-reactive under the reaction condition (e.g., non-reactive with an agent used in the reaction). One skilled in the art will recognize the particular moieties employed for protecting certain functional groups, e.g., hydroxyl group, instead of another functionality, e.g. carboxylic acid. The protecting group reagents include, but are not limited to acylating agents (e.g., acetic anhydride, benzoyl chloride, pivaloyl chloride, etc.), silylating agents (e.g., TMS-Cl, TES-Cl, TBDMS-Cl, etc.), ether forming reagents (MOM-Cl, MEM-Cl, dihydropyran, ethyl vinyl ether, haloalkanes such as iodomethane, bromomethane, iodoethane, bromoethane, etc.), chloroformates (methyl chloroformate, ethyl chloroformate, isobutyl chloroformate, benzyl chloroformate, etc.), in the presence of an appropriate base (e.g., carbonate salts, bicarbonate salts, pyridine, triethylamine, diisopropyl ethylamine, N-methylmorpholine, etc.). Alternatively, an ester-based solvent (e.g., methyl acetate, ethyl acetate, isopropyl acetate, ethyl formate, methyl trifluoroacetate, methyl propionate, etc.) can be used in conjunction with an acid (e.g., methanesulfonic acid, p-toluenesulfonic acid, conc. sulfuric acid, etc.) to selectively acylate the disclosed compounds, e.g., at C-3 position.

As used herein, the term "leaving group" or "LG" refers to a labile functionality that has a propensity to dissociate from carbon (e.g., Cl, Br, I, sulfonated alcohols such as methane sulfonates, p-toluenesulfonates, trifluoromethane sulfonates, trifluoroacetates, sulforylated alcohols, phosphorylated alcohols, etc.). The leaving groups can be either replaced with another functional group or eliminated, e.g., to produce an unsaturated compound, such as, for example, compound of formula B.

As used herein, the term "pharmaceutically acceptable salt" refers to base addition salts including, but are not limited to, alkali metal salts selected from sodium, lithium or potassium salt or alkaline earth metal salts selected from calcium or magnesium. Base addition salts further include inorganic and organic amine salts including, but are not limited to, ammonium, methylammonium, ethylammonium, diethylammonium, triethylammonium, lysine, arginine, N-methylglucamine, and choline. Conventional non-toxic salts also include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, and toluene sulfonic.

"Solvate", as used herein, refers to a solvent addition form of a compound of formula (A) that contains either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier is "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "pharmaceutically acceptable excipient" refers to an excipient that is useful in preparing a pharmaceutical composition that is generally safe, non-toxic and neither biologically nor otherwise undesirable, and includes excipient that is acceptable for veterinary use as well as human pharmaceutical use.

A "pharmaceutical composition" is a formulation containing a compound of formula (A) or a pharmaceutically acceptable salt thereof. In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of a compound of the disclosure or salts thereof) in a unit dose of composition is an effective amount and is varied according to the particular treatment involved.

One skilled in the art will appreciate that it may be necessary to make routine variations to the dosage depending, for example, on the age and condition of the patient. The dosage will also depend on the route of administration. A variety of routes are contemplated, including oral, ocular, ophthalmic, pulmonary, rectal, parenteral, transdermal, subcutaneous, intravenous, intramuscular, intraperitoneal, intranasal, and the like. Dosage forms for the topical or transdermal administration of a compound of this application include powders, sprays, ointments, pastes, creams, lotions, gels, solutions, patches and inhalants. In another embodiment, the active compound is mixed under sterile conditions with a pharmaceutically acceptable carrier, and with any preservatives, buffers, or propellants that are required.

As used herein, the term "amino acid conjugates" refers to conjugates of a compound of the disclosure with any suitable amino acid. Taurine ($-NH(CH_2)_2SO_3H$), glycine ($-NHCH_2CO_2H$), and sarcosine ($-N(CH_3)CH_2CO_2H$) are examples of amino acid conjugates. Suitable amino acid conjugates of the compounds have the added advantage of enhanced integrity in bile or intestinal fluids. Suitable amino acids include, but are not limited to taurine, glycine, and sarcosine. The amino acid conjugates of the compounds of the disclosure can be prepared according to methods known in the art. For example, a free or protected bile acid or bile acid derivative can be coupled to an amino acid (protected or unprotected), e.g., glycine, sarcosine, or taurine amino acid, using standard peptide coupling conditions (e.g., in the presence of a base (e.g., triethylamine, diisopropyl ethylamine (DIPEA), etc.) and specific coupling reagents, for example, N-Ethoxycarbonyl-2-ethoxy-1,2-dihydroquinoline (EEDQ), 4-(4,6-Dimethoxy-1,3,5-triazin-2-yl)-4-methylmorpholinium chloride (DMTMM), etc.).

As defined herein, the term "metabolite" refers to glucuronidated and sulfated derivatives of the compounds described herein, wherein one or more glucuronic acid or sulfate moieties are linked to the compound of the disclosure. Glucuronic acid moieties may be linked to the compounds through glycosidic bonds with the hydroxyl groups of the compounds (e.g., 3-hydroxyl, 7-hydroxyl, 11-hydroxyl, and/or the hydroxyl of the $R^7$ group). Sulfated derivatives of the compounds may be formed through sulfation of the hydroxyl groups (e.g., 3-hydroxyl, 7-hydroxyl, 11-hydroxyl, and/or the hydroxyl of the $R^7$ group). Examples of metabolites include, but are not limited to, 3-O-glucuronide, 7-O-glucuronide, 11-O-glucuronide, 3-O-7-O-diglucuronide, 3-O-11-O-triglucuronide, 7-O-11-O-triglucuronide, and 3-O-7-O-11-O-triglucuronide, of the compounds described herein, and 3-sulfate, 7-sulfate, 11-sulfate, 3,7-bisulfate, 3,11-bisulfate, 7,11-bisulfate, and 3,7,11-trisulfate, of the compounds described herein. Many drug molecules have been conjugated to glucuronic acid in order to obtain the required derivatives as tools for improving insights on their absorption, metabolism and bioavailability. Isolation of the metabolites is often laborious and analytical standards are necessary as reference compounds for quantification of metabolite levels in clinical samples and for further pharmacological evaluation. The study of metabolites of drugs can contribute to the toxicity, research, and safety assessment of the drug molecules. Some glucuronides have similar or even greater biological activity compared to their corresponding parent drug molecules. For example, well-known active glucuronide is morphine 6-O-glucuronide, which has even more analgesic action than morphine (Ritter, Chem. Biol. Interact. 129 (2000) 171-193). Methods of chemical and enzymatic synthesis of glucuronides are well-known in the art. The Koenigs-Knorr reaction is one of the most widely applied methods for the synthesis of alkyl and aryl O-glucuronide compounds. In this reaction, the aglycone (starting alcohol or phenol) is coupled with, for example, methyl acetobromo-α-D-glucuronate in the presence of, for example, silver salts. If the substrate molecule (aglycone) has multiple glucuronidation sites, chemical synthesis can yield a mixture of mono- and polyglucuronides unless the unwanted glucuronidation sites are protected. The reaction gives glucuronides in variable yields depending on the catalyst, solvent, aglycone, and the ratio of the starting materials used. Other methods have been used for the synthesis of glucuronides including flow methods (Mostarda, et al. Org. Biomol. Chem. 12 (2014) 9592-9600); the main differences between the reactions are in the glycosyl donor (Stachulski, et al., J. Med. Chem. 49 (2006) 6931-6945; Kaspersen, et al., Xenobiotica 17 (1987) 1451-1471 (methods of chemical synthesis of sulfate and glucuronide conjugates.); Stachulski, et al., Nat. Prod. Rep. 15 (1998) 173-186).

The term "prodrug" as used herein, refers to a bile acid derivative or compound that, after administration, is metabolized (i.e., converted within the body) into a pharmacologically active drug. Inactive prodrugs are pharmacologically inactive medications that are metabolized into an active form within the body. Instead of administering a drug directly, a corresponding prodrug might be used instead to improve how a medicine is absorbed, distributed, metabolized, and excreted (ADME). Prodrugs are often designed to improve bioavailability when a drug itself is poorly absorbed from the gastrointestinal tract. A prodrug may be used to improve how selectively the drug interacts with cells or processes that are not its intended target. This can reduce adverse or unintended effects of a drug, especially important in treatments having severe unintended and undesirable side effects.

The term "treating", as used herein, refers to relieving, lessening, reducing, eliminating, modulating, or ameliorating, i.e., causing regression of the disease state or condition.

The term "preventing", as used herein, refers to completely or almost completely stop a disease state or condition, from occurring in a patient or subject, especially when the patient or subject is predisposed to such or at risk of contracting a disease state or condition. Preventing can also include inhibiting, i.e., arresting the development, of a disease state or condition, and relieving or ameliorating, i.e., causing regression of the disease state or condition, for example when the disease state or condition may already be present.

The phrase "reducing the risk of", as used herein, refers to lowering the likelihood or probability of a central nervous system disease, inflammatory disease and/or metabolic disease from occurring in a patient, especially when the subject is predisposed to such occurrence.

"Combination therapy" (or "co-therapy") refers to the administration of a compound of the disclosure and at least a second agent as part of a specific treatment regimen intended to provide the beneficial effect from the co-action of these therapeutic agents (i.e., the compound of the disclosure and at least a second agent). The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present application. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be affected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or mechanical treatments). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks. As used herein, "combination therapy" means that a compound of the application can be administered in conjunction with another therapeutic agent. "In conjunction with" refers to administration of one treatment modality in addition to another treatment modality, such as administration of a compound of the application as described herein in addition to administration of another therapeutic agent to the same subject. As such, "in conjunction with" refers to administration of one treatment modality before, during, or after delivery of a second treatment modality to the subject.

An "effective amount" of a compound of the disclosure, or a combination of compounds is an amount (quantity or concentration) of compound or compounds. In one embodiment, when a therapeutically effective amount of a compound is administered to a subject in need of treatment symptoms arising from the disease are ameliorated immediately or after administration of the compound one or more times. The amount of the compound to be administered to a subject will depend on the particular disorder, the mode of administration, coadministered compounds, if any, and the characteristics of the subject, such as general health, other diseases, age, sex, genotype, body weight, and tolerance to drugs. The skilled artisan will be able to determine appropriate dosages depending on these and other factors.

The term "prophylactically effective amount" means an amount (quantity or concentration) of a compound of the present disclosure, or a combination of compounds, that is administered to prevent or reduce the risk of a disease—in other words, an amount needed to provide a preventative or prophylactic effect. The amount of the present compound to be administered to a subject will depend on the particular disorder, the mode of administration, coadministered compounds, if any, and the characteristics of the subject, such as general health, other diseases, age, sex, genotype, body weight, and tolerance to drugs. The skilled artisan will be able to determine appropriate dosages depending on these and other factors.

A "subject" includes mammals, e.g., humans, companion animals (e.g., dogs, cats, birds, and the like), farm animals (e.g., cows, sheep, pigs, horses, and the like), and laboratory animals (e.g., rats, mice, guinea pigs, and the like). Typically, the subject is human.

As used herein, farnesoid X receptor or FXR refers to all mammalian forms of such receptor including, for example, alternative splice isoforms and naturally occurring isoforms (see, e.g., Huber et al., Gene 290:35-43 (2002)). Representative FXR species include, without limitation rat FXR (GenBank Accession No. NM 021745), mouse FXR (GenBank Accession No. NM 009108), and human FXR (GenBank Accession No. NM 005123).

The term "about" as used herein when referring to a measurable value such as an amount, a temporal duration, and the like, is meant to encompass variations of ±20% or ±10%, in some embodiments ±5%, in some embodiments ±1%, and in some embodiments ±0.1% from the specified value, as such variations are appropriate to practice the disclosed methods or to make and used the disclosed compounds and in the claimed methods.

Methods of the Invention

In one aspect, the present disclosure relates to a method of preparing a compound of formula I:

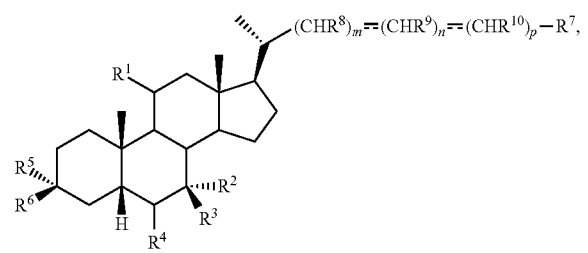

I or a pharmaceutically acceptable salt, solvate, amino acid, sulfate or glucuronide conjugate, or prodrug thereof, wherein:

$R^1$ is OH, alkoxy, or oxo;

$R^2$ and $R^3$ are each independently H, OH, $OSO_3H$, $OCOCH_3$, $OPO_3H_2$, halogen, or alkyl optionally substituted with one or more halogen or OH, or $R^2$ and $R^3$ taken together with the carbon atom to which they are attached form a carbonyl;

$R^4$ is H, halogen, alkyl optionally substituted with one or more halogen or OH, alkenyl, or alkynyl;

$R^5$ and $R^6$ are each independently H, OH, $OSO_3H$, $OCOCH_3$, $OPO_3H_2$, halogen, or alkyl optionally substituted with one or more halogen or OH, or $R^5$ and $R^6$ taken together with the carbon atom to which they are attached form a carbonyl;

$R^7$ is OH, $OSO_3H$, $SO_3H$, $OSO_2NH_2$, $SO_2NH_2$, $OPO_3H_2$, $PO_3H_2$, $CO_2H$, $C(O)NHOH$, $NH(CH_2)_2SO_3H$, $NHCH_2CO_2H$, tetrazolyl, oxadiazolyl, thiadiazolyl, 5-oxo-1,2,4-oxadiazolyl, 5-oxo-1,2,4-thiadiazolyl, oxazolidine-dionyl, thiazolidine-dionyl, 3-hydroxyisoxazolyl, 3-hydroxyisothiazolyl, pyrimidine, 3,5-difluoro-4-hydroxyphenyl or 2,4-difluoro-3-hydroxyphenyl;

$R^8$, $R^9$, and $R^{10}$ are each independently H, OH, halogen, or alkyl optionally substituted with one or more halogen or OH, or $R^8$ and $R^9$ taken together with the carbon atoms to which they are attached form a 3- to 6-membered carbocyclic or heterocyclic ring comprising 1 or 2 heteroatoms selected from N, O, and S, or $R^9$ and $R^{10}$ taken together with the carbon atoms to which they are attached form a 3- to 6-membered carbocyclic or heterocyclic ring comprising 1 or 2 heteroatoms selected from N, O, and S;

m is 0, 1, or 2;

n is 0 or 1; and p is 0 or 1;

the method comprising the steps 1-8 as shown in Scheme A.

Scheme A

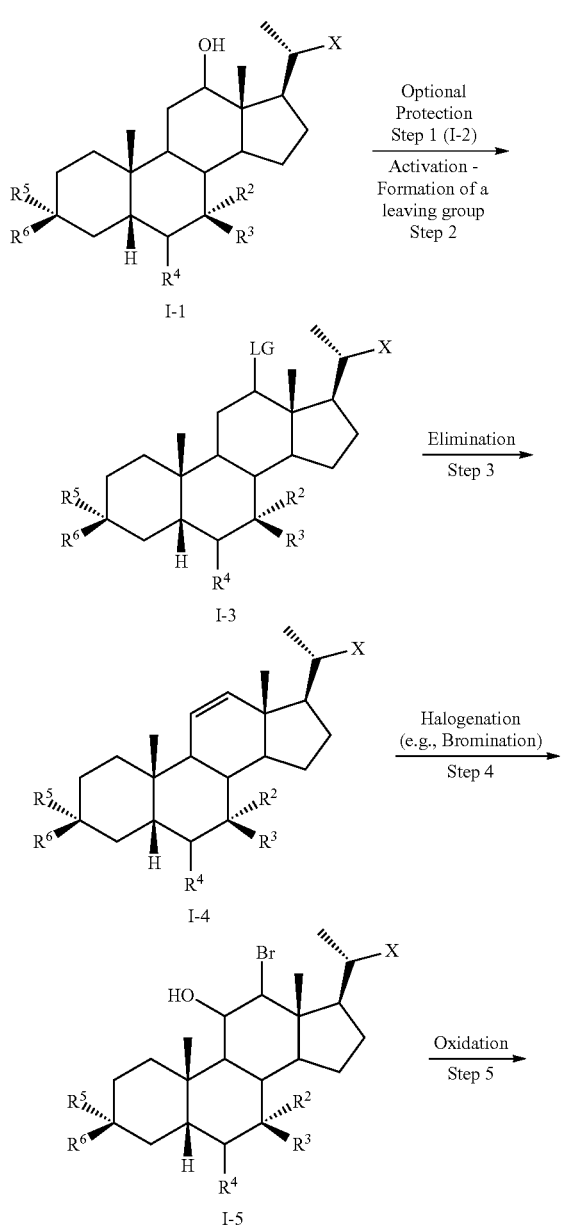

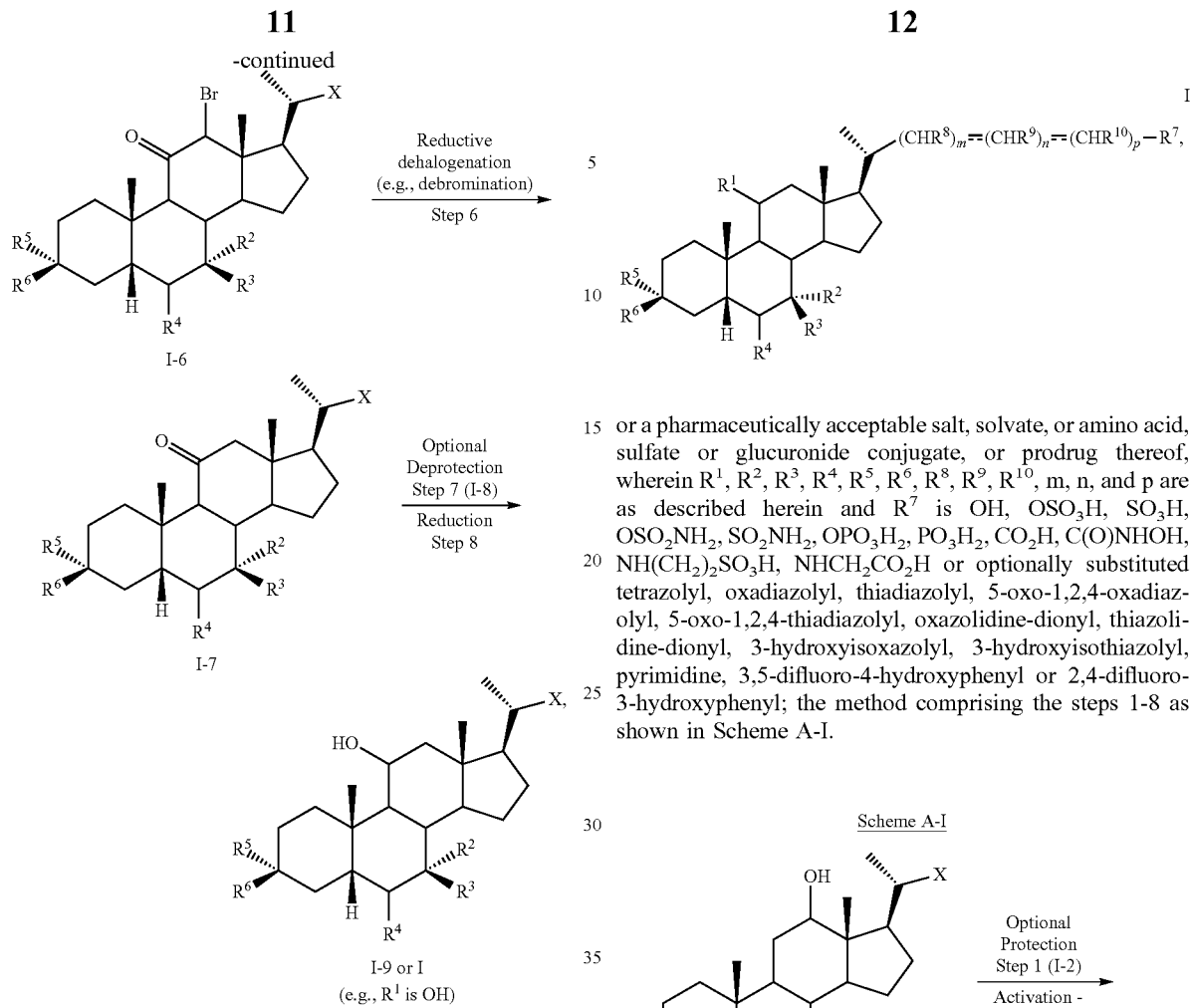

I-6

I-7

I-9 or I
(e.g., R¹ is OH)

wherein X is —(CHR⁸)$_m$═(CHR⁹)$_n$═(CHR¹⁰)$_p$—R⁷; R², R³, R⁵, R⁶, R⁷, R⁸, R⁹, and R¹⁰ are as described above and each may be protected by R¹¹ or another suitable protecting group if needed.

According to Scheme A, the process of preparing the compound of formula I comprises the steps of
1) optionally protecting a compound of formula I-1 to provide compound of formula I-2;
2) treating the compound of formula I-1 or I-2 with an appropriate activating agent to provide a compound of formula I-3, wherein LG is a leaving group;
3) treating the compound of formula I-3 with a base to prepare a compound of formula I-4;
4) reacting a compound of formula I-4 with a halogenating (e.g., brominating) reagent to provide a compound of formula I-5;
5) reacting the compound of formula I-5 with an oxidizing agent to prepare a compound of formula I-6;
6) reacting the compound of formula I-6 with a reducing agent to prepare the compound of formula I-7 (reductive dehalogenation or debromination);
7) optionally deprotecting the compound of formula I-7 to obtain the compound of formula I-8; and
8) reacting the compound of formula I-7 or I-8 with a reducing agent to provide the compound of formula I-9 or I.

Some embodiments of the present disclosure relate to a method of preparing a compound of formula I:

or a pharmaceutically acceptable salt, solvate, or amino acid, sulfate or glucuronide conjugate, or prodrug thereof, wherein R¹, R², R³, R⁴, R⁵, R⁶, R⁸, R⁹, R¹⁰, m, n, and p are as described herein and R⁷ is OH, OSO₃H, SO₃H, OSO₂NH₂, SO₂NH₂, OPO₃H₂, PO₃H₂, CO₂H, C(O)NHOH, NH(CH₂)₂SO₃H, NHCH₂CO₂H or optionally substituted tetrazolyl, oxadiazolyl, thiadiazolyl, 5-oxo-1,2,4-oxadiazolyl, 5-oxo-1,2,4-thiadiazolyl, oxazolidine-dionyl, thiazolidine-dionyl, 3-hydroxyisoxazolyl, 3-hydroxyisothiazolyl, pyrimidine, 3,5-difluoro-4-hydroxyphenyl or 2,4-difluoro-3-hydroxyphenyl; the method comprising the steps 1-8 as shown in Scheme A-I.

Scheme A-I

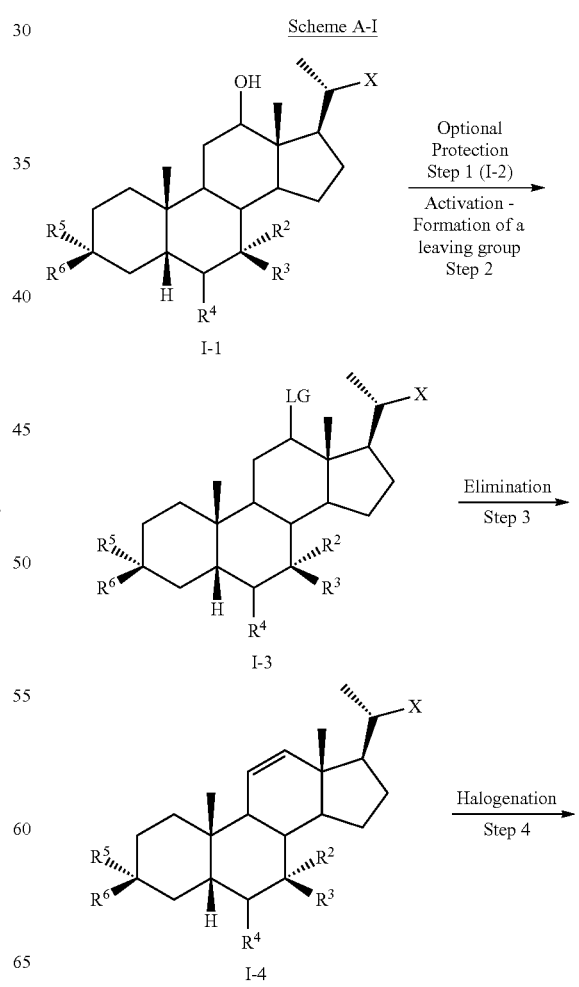

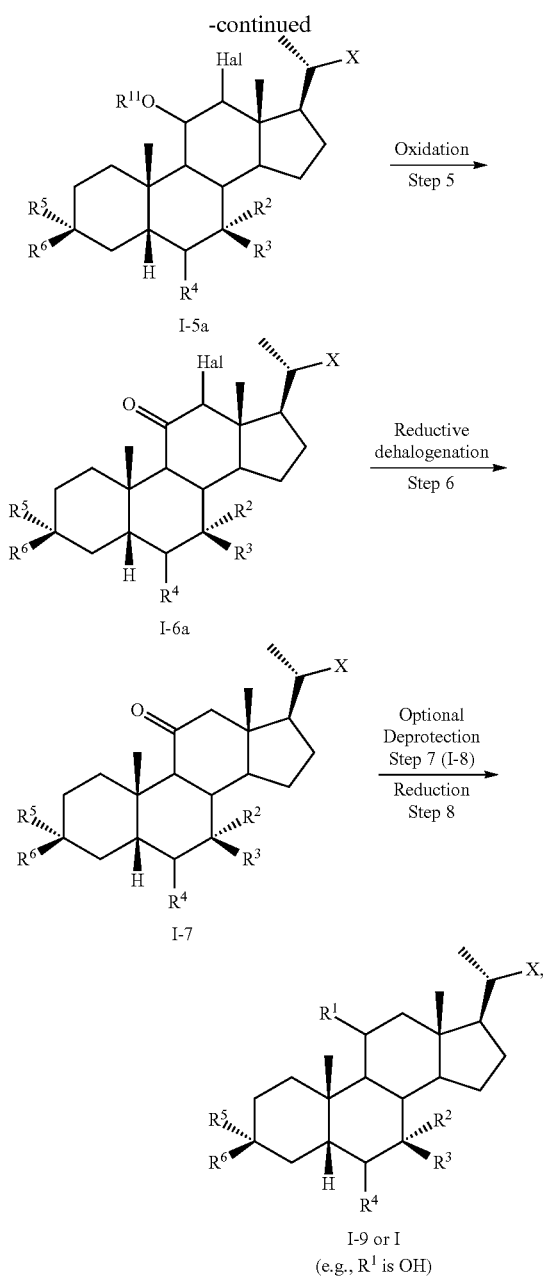

I-5a

Oxidation Step 5

I-6a

Reductive dehalogenation Step 6

I-7

Optional Deprotection Step 7 (I-8)

Reduction Step 8

I-9 or I
(e.g., $R^1$ is OH)

wherein X is —$(CHR^8)_m$ === $(CHR^9)_n$ === $(CHR^{10})_p$—$R^7$; $R^1$, $R^2$, $R^3$, $R^4$, $R^5$, $R^6$, $R^7$, $R^8$, $R^9$, and $R^{10}$ are as described above and each —OH can be —$OR^{11}$, wherein $R^{11}$ is H or any suitable protecting group; Hal is halogen (e.g., Br, I, or as described herein) and LG is a suitable leaving group.

According to Scheme A-I, the process of preparing the compound of formula I comprises the steps of
1) optionally protecting a compound of formula I-1 to provide compound of formula I-2;
2) treating the compound of formula I-1 or I-2 with an appropriate activating agent to provide a compound of formula I-3, wherein LG is a leaving group;
3) treating the compound of formula I-3 with a base to prepare a compound of formula I-4;
4) reacting a compound of formula I-4 with a halogenating (e.g., brominating or iodinating) reagent to provide a compound of formula I-5a;
5) reacting the compound of formula I-5a with an oxidizing agent to prepare a compound of formula I-6a;
6) reacting the compound of formula I-6a with a reducing agent to prepare the compound of formula I-7 (reductive dehalogenation, e.g., debromination or deiodination);
7) optionally deprotecting the compound of formula I-7 to obtain the compound of formula I-8; and
8) reacting the compound of formula I-7 or I-8 with a reducing agent to provide the compound of formula I-9 or I. In one of the embodiments X is —$(CHR^8)_m$ === $(CHR^9)_n$ === $(CHR^{10})_p$—$CO_2Me$, where $R^8$, $R^9$, and $R^{10}$ are as described herein.

In certain embodiments, Hal is iodine. In some embodiments Hal is bromine.

In some embodiments, compounds of the disclosure, or pharmaceutically acceptable salts, solvates, or amino acid conjugates thereof are isotopically labeled (or radiolabeled). Examples of isotopes that can be incorporated into compounds of the disclosure, or pharmaceutically acceptable salts, solvates, or amino acid conjugates thereof include isotopes of hydrogen, carbon, nitrogen, fluorine, such as $^2H$, $^3H$, $^{11}C$, $^{13}C$, $^{14}C$, and $^{18}F$. In some embodiments, compounds of the disclosure are deuterated, i.e., incorporate $^2H$, tritiated, i.e., incorporate $^3H$, and radiolabed with carbon-14, i.e., $^{14}C$. Isotopically labeled compounds of the disclosure, or pharmaceutically acceptable salts, solvates, or amino acid conjugates thereof can generally be prepared by carrying out the procedures disclosed in the Schemes and/or in the Examples, by substituting a readily available isotopically labeled reagent for a non-isotopically labeled reagent.

In certain embodiments, the present disclosure relates to a method of preparing a compound of formula I or I-9, where $R^1$ is alpha-hydroxy, compound of formula I-9a:

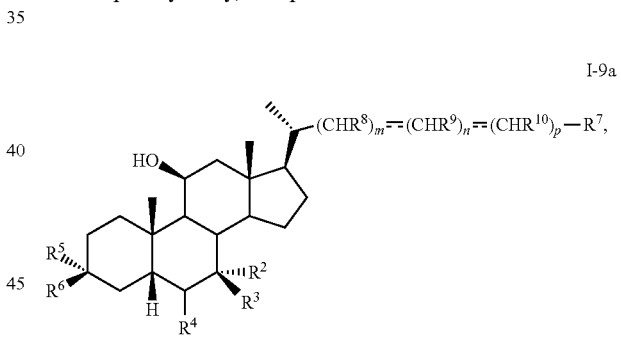

I-9a or a pharmaceutically acceptable salt, solvate, or amino acid, sulfate or glucuronide conjugate, or prodrug thereof, wherein $R^2$-$R^{10}$ are as described herein.

In some embodiments, the compound of formula I or I-9 or I-9a, wherein $R^7$ is $OSO_3H$, $SO_3H$, $OSO_2NH_2$, $SO_2NH_2$, $OPO_3H_2$, $PO_3H_2$, $CO_2H$, $C(O)NHOH$, tetrazolyl, oxadiazolyl, thiadiazolyl, 5-oxo-1,2,4-oxadiazolyl, 5-oxo-1,2,4-thiadiazolyl, oxazolidinedionyl, thiazolidinedionyl, 3-hydroxyisoxazolyl, 3-hydroxyisothiazolyl, pyrimidine, 3,5-difluoro-4-hydroxyphenyl or 2,4-difluoro-3-hydroxyphenyl, all of which can be optionally further substituted, can be pepsred using synthetic procedures described in WO 2017/062763, US20160130297, US20160145295, US20160145296, US20160185815, US20160229886, US20160289262, and WO 2018/081285 or using other procedure known in the art. The presently disclosed method provides an efficient synthesis of intermediates that can be further elaborated to various side chain analogs, including, but not limited to compounds with the following side chains:

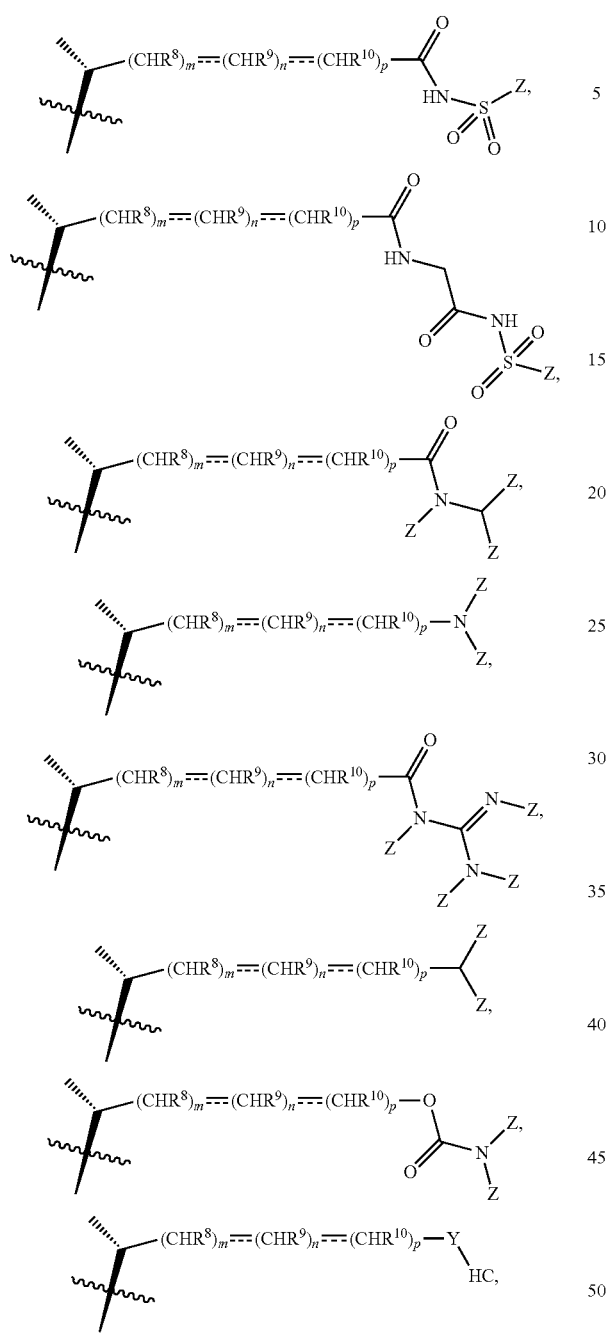

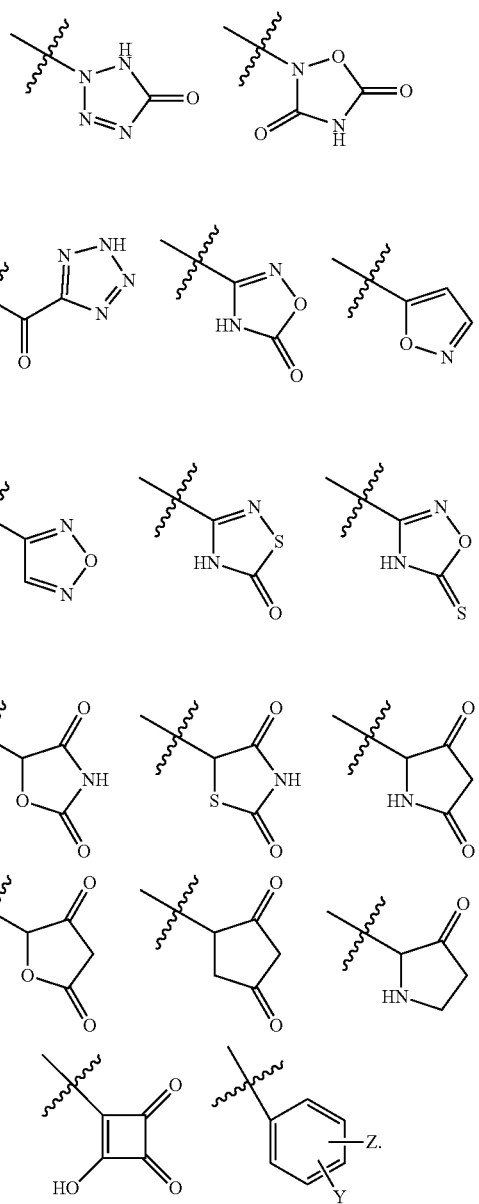

where Z is any same or different appropriate substituent, Y-heteroatom (e.g., O, N, or S), and HC is any appropriate heterocycle (e.g., aromatic or non-aromatic 4-6-membered ring), which, for example, can include, but is not limited to the following groups

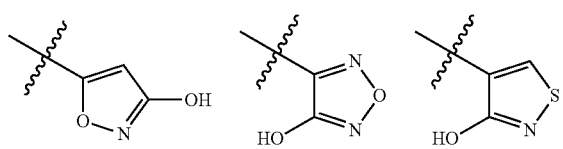

In one of the embodiments, in Scheme A-I, step 1) is protecting a compound of formula I-1 to provide compound of formula I-2, wherein $R^{11}$ is a protecting group

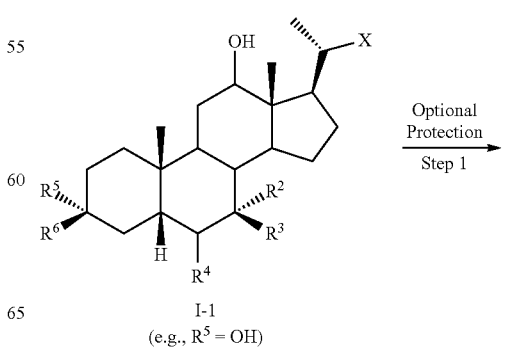

-continued

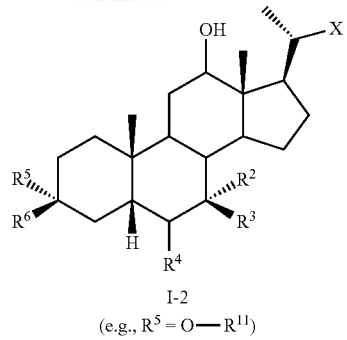

I-2
(e.g., R⁵ = O—R¹¹)

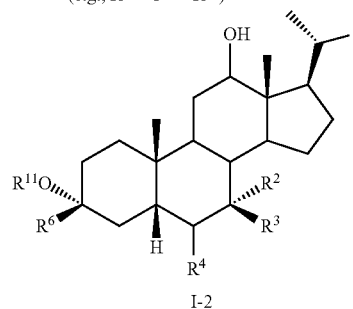

I-2 and step 2) is treating the compound of formula I-1 or I-2 with an appropriate activating agent to provide a compound of formula I-3, wherein LG is a leaving group, which can be performed sequentially in one pot without isolation of intermediates via a telescopic process (two-step, one-pot procedure).

In certain embodiments, the present disclosure relates to a method of preparing a compound of formula I:

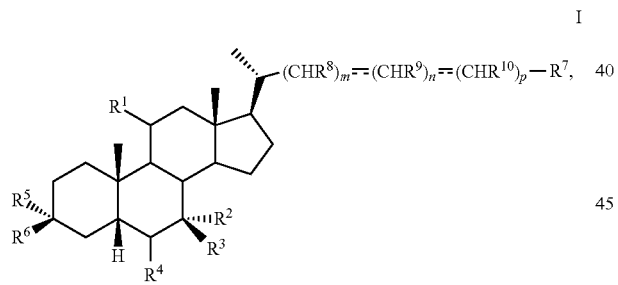

I or a pharmaceutically acceptable salt, solvate, amino acid or sulfate or glucuronide conjugate, or prodrug thereof, wherein $R^1$ is OH, alkoxy, or oxo;

$R^2$ and $R^3$ are each independently H, OH, OSO$_3$H, OCOCH$_3$, OPO$_3$H$_2$, halogen, or alkyl optionally substituted with one or more halogen or OH, or $R^2$ and $R^3$ taken together with the carbon atom to which they are attached form a carbonyl;

$R^4$ is H, halogen, alkyl optionally substituted with one or more halogen or OH, alkenyl, or alkynyl;

$R^5$ and $R^6$ are each independently H, OH, OSO$_3$H, OCOCH$_3$, OPO$_3$H$_2$, halogen, or alkyl optionally substituted with one or more halogen or OH, or $R^5$ and $R^6$ taken together with the carbon atom to which they are attached form a carbonyl;

$R^7$ is OH, OSO$_3$H, SO$_3$H, OSO$_2$NH$_2$, SO$_2$NH$_2$, OPO$_3$H$_2$, PO$_3$H$_2$, CO$_2$H, C(O)NHOH, NH(CH$_2$)$_2$SO$_3$H, NHCH$_2$CO$_2$H or optionally substituted tetrazolyl, oxadiazolyl, thiadiazolyl, 5-oxo-1,2,4-oxadiazolyl, 5-oxo-1,2,4-thiadiazolyl, oxazolidine-dionyl, thiazolidine-dionyl, 3-hydroxyisoxazolyl, 3-hydroxyisothiazolyl, pyrimidine, 3,5-difluoro-4-hydroxyphenyl or 2,4-difluoro-3-hydroxyphenyl;

$R^8$, $R^9$, and $R^{10}$ are each independently H, OH, halogen, or alkyl optionally substituted with one or more halogen or OH, or $R^8$ and $R^9$ taken together with the carbon atoms to which they are attached form a 3- to 6-membered carbocyclic or heterocyclic ring comprising 1 or 2 heteroatoms selected from N, O, and S, or $R^9$ and $R^{10}$ taken together with the carbon atoms to which they are attached form a 3- to 6-membered carbocyclic or heterocyclic ring comprising 1 or 2 heteroatoms selected from N, O, and S;

m is 0, 1, or 2;

n is 0 or 1; and p is 0 or 1;

the method comprising the steps of
1) optionally protecting a compound of formula I-1 to provide compound of formula I-2;
2) treating the compound of formula I-1 or I-2 with an appropriate activating agent to provide a compound of formula I-3, wherein LG is a leaving group;
3) treating the compound of formula I-3 with a base to prepare a compound of formula I-4;
4) reacting a compound of formula I-4 with a halogenating (e.g., brominating or iodinating) reagent to provide a compound of formula I-5a;
5) reacting the compound of formula I-5a with an oxidizing agent to prepare a compound of formula I-6a;
6) reacting the compound of formula I-6a with a reducing agent to prepare the compound of formula I-7 (reductive dehalogenation or debromination or deiodination);
7) optionally deprotecting the compound of formula I-7 to obtain the compound of formula I-8; and
8) reacting the compound of formula I-7 or I-8 with a reducing agent to provide the compound of formula I.

In certain embodiments compound of formula I is a compound of formula I-9

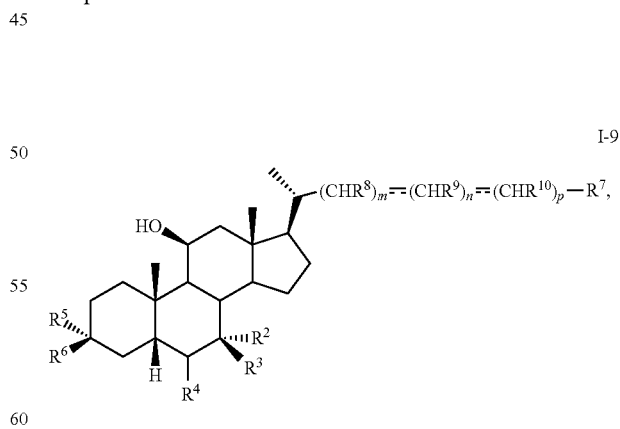

I-9 wherein $R^1$ is OH and $R^2$, $R^3$, $R^4$, $R^5$, $R^6$, $R^7$, $R^8$, $R^9$, and $R^{10}$ are as described above.

In one of the embodiments, the method of preparing a compound of formula I or I-9 comprises alternative steps from compound of formula I-5 (e.g., I-5b) as shown in Scheme A1.

Scheme A1

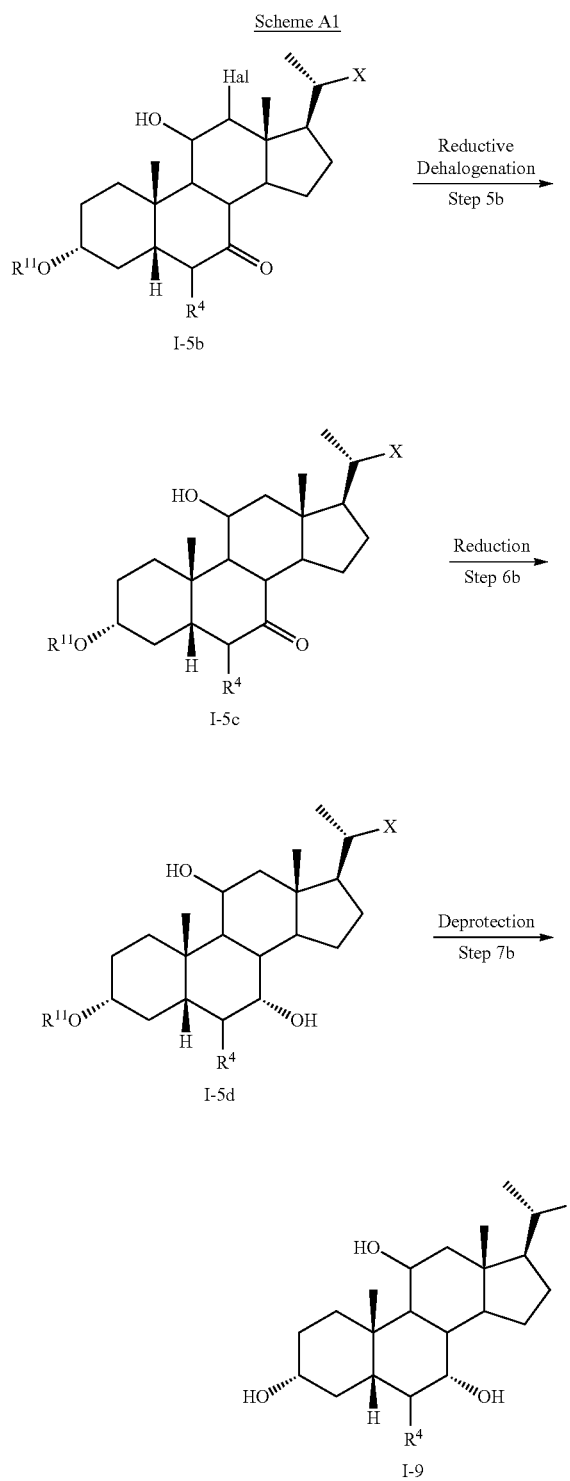

2) reacting the compound of formula I-5c with a reducing agent to provide the compound of formula I-5d (Step 6b; ketone reduction in the presence of protecting groups at C3);
3) deprotecting the compound of formula I-5d to provide the compound of formula I or I-9 (Step 7b).

In some embodiments step 6b or other reductions of C7 ketone are conducted in the presence of protecting groups at C3 via, for example borohydride reduction or catalytic hydrogenation.

In some embodiments step 7b deprotection of X (e.g., $R^7$ is methyl ester) and removal of protecting group $R^{11}$ at C3 may be done selectively and occur in a stepwise fashion, or may occur simultaneously. In one of the embodiments, C3 hydroxy can be protected as, for example, an alkyloxycarbonyl, then both the side chain X protecting group (e.g., $R^7$ is methyl ester) and C3 hydroxy protecting group can be removed simultaneously under basic conditions. In other embodiments, C3 hydroxy can be protected as, for example, a pivolate, then the side chain X protecting group (e.g., $R^7$ is methyl ester) can be removed first keeping the C3 hydroxy protecting group intact. Stepwise deprotection allows for isolation of penultimate intermediates of compound I or I-9 (e.g., 100), thereby providing alternative opportunities for purification (e.g., crystallization) of intermediates (e.g., compounds of formula I-5d) and final products (e.g., compounds of formula I or I-9).

In some embodiments the order of steps 6b and 7b may be reversed, such that the deprotection step as described above may occur prior to the ketone reduction step.

In one of the embodiments, compound of formula I-7a can be prepared from compound I-4 (e.g., wherein $R^2$ and $R^3$ form a carbonyl). In a certain embodiment, compound of formula I-7a can be prepared from compound I-4 (e.g., wherein $R^2$ and $R^3$ form a carbonyl) via a telescopic procedure. In some embodiments, the method of preparing the compound of formula I or I-9 comprises alternative steps from compound of formula I-7 (e.g., I-7a) as shown in Scheme A2.

Scheme A2

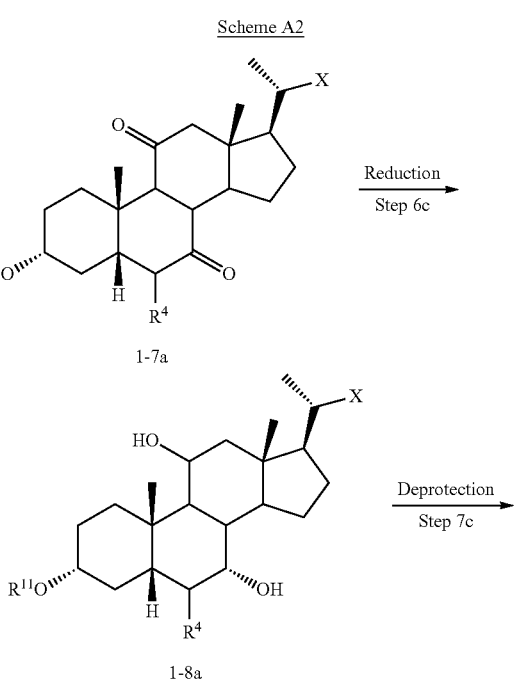

According to Scheme A1, the method of preparing a compound of formula I or I-9 starting from a compound of formula I-5 (e.g., I-5b) comprises the steps of:
1) reacting compound of formula I-5b with a reducing agent to prepare the compound of formula I-5c (Step 5b; reductive dehalogenation (e.g., debromination, deiodination, etc.);

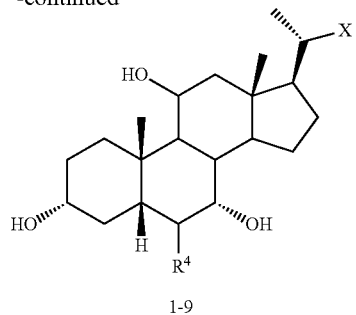

1-9

According to Scheme A2, an alternative process of preparing the compound of formula I or I-9 starting from compound of formula I-7a comprises the steps of:
1) reacting the compound of formula I-7a with a reducing agent to provide the compound of formula I-8a (Step 6c);
2) deprotecting the compound of formula I-8a to obtain the compound of formula I or I-9 (Step 7c).

The synthetic processes of the present disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester, prodrug, or amino acid, sulfate, or glucuronide conjugate thereof.

In one of the embodiments, the compound of formula I-1 is a compound of formula A'

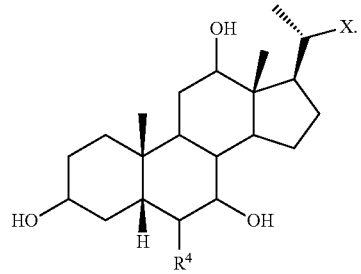

A'

In one of the embodiments, the compound of formula I-1 is compound A

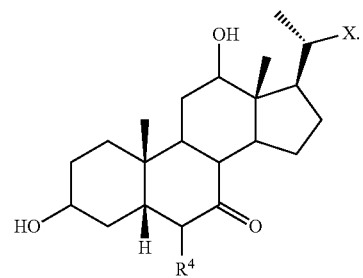

A

In one of the embodiments, the compound of formula I-1 is compound A"

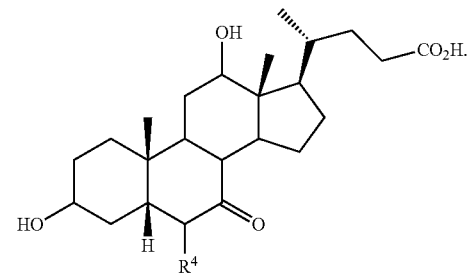

A"

In one of the embodiments, the compound of formula I-1 is compound A1

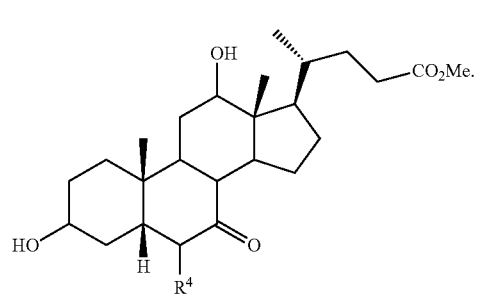

A'''

In one of the embodiments, the compound of formula I-1 is compound 1

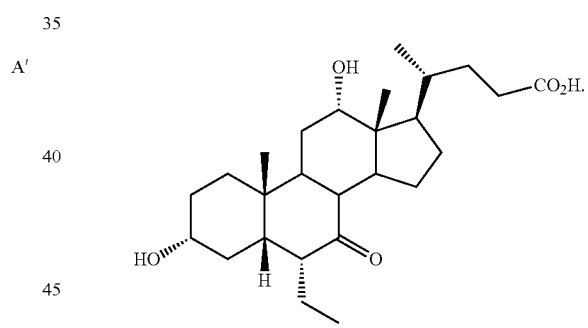

1

In one of the embodiments, the present disclosure relates to a process of making compound of formula C2 as shown in Scheme 1.

Scheme 1

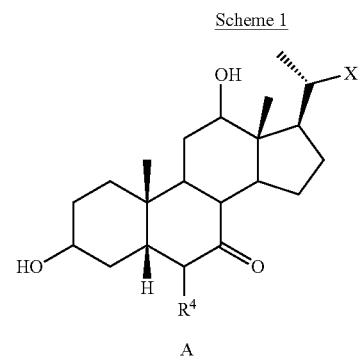

A

Protection
Step 1

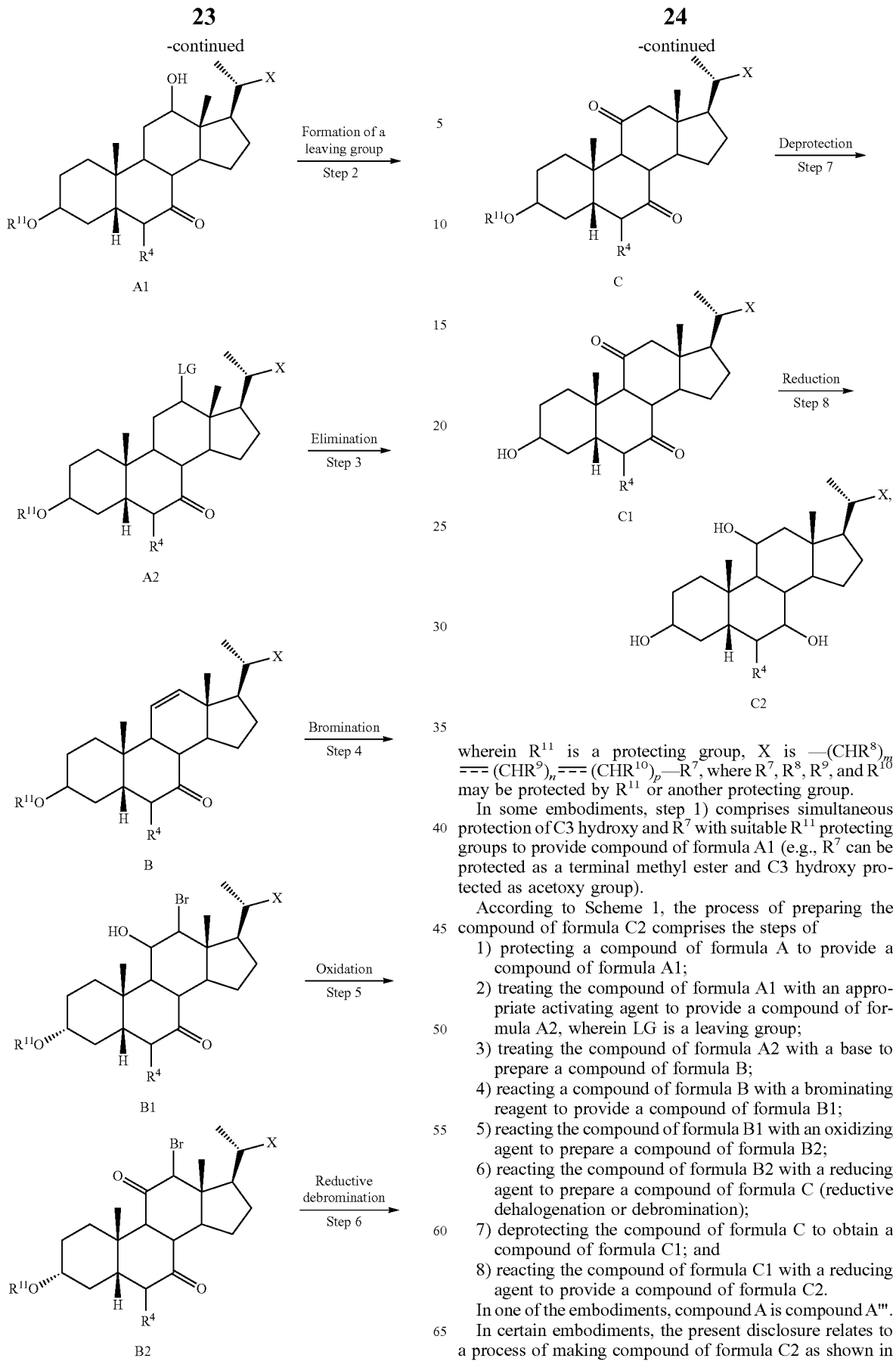

wherein $R^{11}$ is a protecting group, X is $—(CHR^8)_m$ $===(CHR^9)_n===(CHR^{10})_p—R^7$, where $R^7$, $R^8$, $R^9$, and $R^{10}$ may be protected by $R^{11}$ or another protecting group.

In some embodiments, step 1) comprises simultaneous protection of C3 hydroxy and $R^7$ with suitable $R^{11}$ protecting groups to provide compound of formula A1 (e.g., $R^7$ can be protected as a terminal methyl ester and C3 hydroxy protected as acetoxy group).

According to Scheme 1, the process of preparing the compound of formula C2 comprises the steps of 1) protecting a compound of formula A to provide a compound of formula A1;
2) treating the compound of formula A1 with an appropriate activating agent to provide a compound of formula A2, wherein LG is a leaving group;
3) treating the compound of formula A2 with a base to prepare a compound of formula B;
4) reacting a compound of formula B with a brominating reagent to provide a compound of formula B1;
5) reacting the compound of formula B1 with an oxidizing agent to prepare a compound of formula B2;
6) reacting the compound of formula B2 with a reducing agent to prepare a compound of formula C (reductive dehalogenation or debromination);
7) deprotecting the compound of formula C to obtain a compound of formula C1; and
8) reacting the compound of formula C1 with a reducing agent to provide a compound of formula C2.

In one of the embodiments, compound A is compound A'''.

In certain embodiments, the present disclosure relates to a process of making compound of formula C2 as shown in Scheme 1A.

Scheme 1A

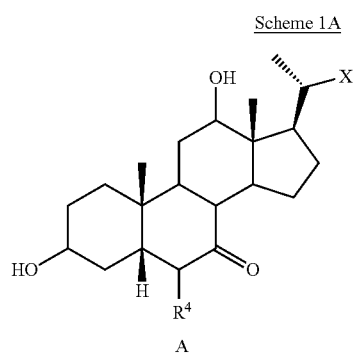
A

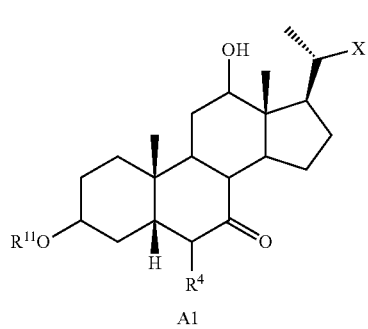
A1

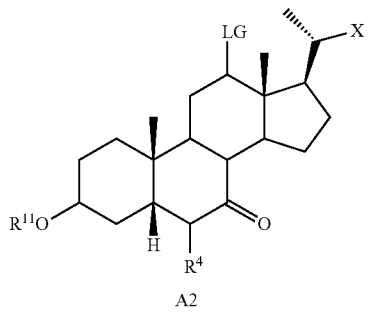
A2

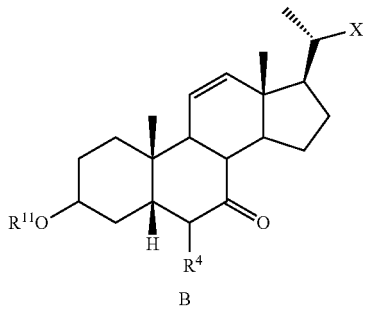
B

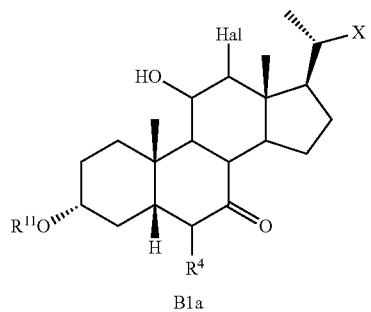
B1a

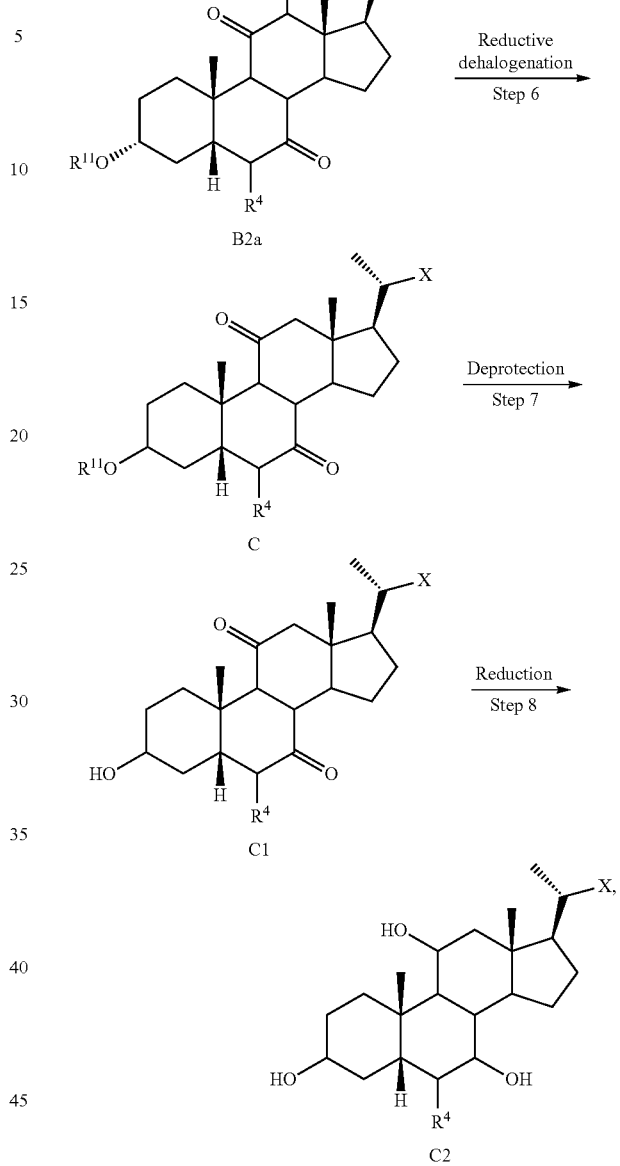

wherein $R^{11}$ is a protecting group, X is —(CHR$^8$)$_m$ ═══ (CHR$^9$)$_n$ ═══ (CHR$^{10}$)$_p$—R$^7$, where R$^7$, R$^8$, R$^9$, R$^{10}$ and R$^{11}$ are as described herein.

According to Scheme 1A, the process of preparing the compound of formula C2 comprises the steps of 1) protecting a compound of formula A to provide a compound of formula A1;
2) treating the compound of formula A1 with an appropriate activating agent to provide a compound of formula A2, wherein LG is a leaving group;
3) treating the compound of formula A2 with a base to prepare a compound of formula B;
4) reacting a compound of formula B with a halogenating (e.g., brominating or iodinating) reagent to provide a compound of formula B1a;
5) reacting the compound of formula B1a with an oxidizing agent to prepare a compound of formula B2a;

6) reacting the compound of formula B2a with a reducing agent to prepare a compound of formula C (reductive dehalogenation e.g., debromination or deiodination);
7) deprotecting the compound of formula C to obtain a compound of formula C1; and
8) reacting the compound of formula C1 with a reducing agent to provide a compound of formula C2.

In some embodiments X is —$(CHR^8)_m$===$(CHR^9)_n$===$(CHR^{10})_p$—$CO_2Me$, where $R^8$, $R^9$, and $R^{10}$ are as described herein. In certain embodiments, compound of formula A is compound of formula A'''.

In some embodiments, the present disclosure relates to a process of making compound of formula A2 as shown in Scheme 1A-1, comprising of the following steps:
1) protecting a compound of formula A to provide a compound of formula A1, and
2) treating the compound of formula A1 with an appropriate activating agent to provide a compound of formula A2, wherein LG is a leaving group.

These two steps can be executed sequentially without work-up or isolation of intermediate compound of formula A1 (i.e., a telescopic, or two-step, one-pot procedure) thereby improving the overall efficiency of manufacturing operations.

Scheme 1A-1

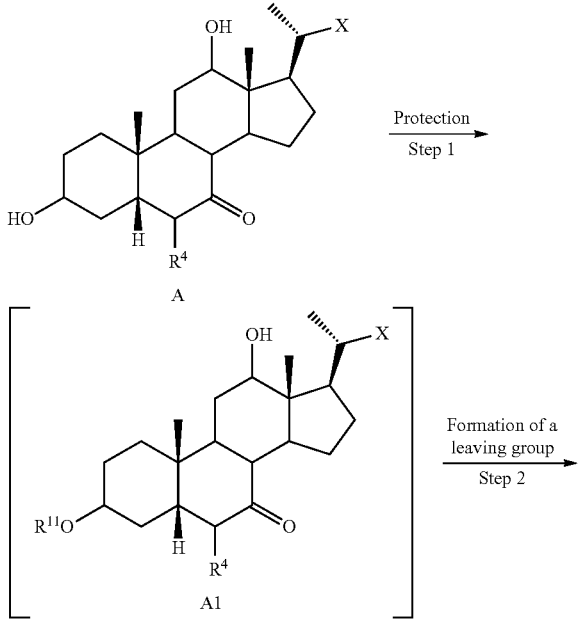

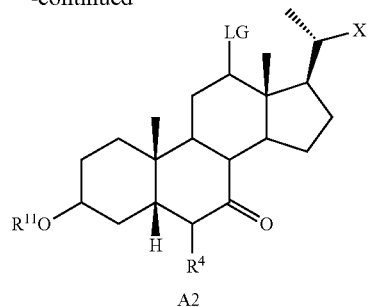

In some embodiments X is —$(CHR^8)_m$===$(CHR^9)_n$===$(CHR^{10})_p$—$CO_2Me$, where $R^8$, $R^9$, and $R^{10}$ are as described herein. In certain embodiments, compound of formula A is compound of formula A'''.

In some embodiments, the compound of formula I-9 or C2 is further transformed into the compound of formula I, wherein $R^7$ is $OSO_3H$, $SO_3H$, $OSO_2NH_2$, $SO_2NH_2$, $OPO_3H_2$, $PO_3H_2$, C(O)NHOH, tetrazolyl, oxadiazolyl, thiadiazolyl, 5-oxo-1,2,4-oxadiazolyl, 5-oxo-1,2,4-thiadiazolyl, oxazolidinedionyl, thiazolidinedionyl, 3-hydroxyisoxazolyl, 3-hydroxyisothiazolyl, or 2,4-difluoro-3-hydroxyphenyl, and $R^1$ is alkoxy or oxo using known synthetic procedures. In some embodiments, the compound of formula I-9 or C2 is further transformed into the compound of formula I, wherein $R^7$ is $OSO_3H$, $SO_3H$, $OSO_2NH_2$, $SO_2NH_2$, $OPO_3H_2$, $PO_3H_2$, $CO_2H$, C(O)NHOH, tetrazolyl, oxadiazolyl, thiadiazolyl, 5-oxo-1,2,4-oxadiazolyl, 5-oxo-1,2,4-thiadiazolyl, oxazolidinedionyl, thiazolidinedionyl, 3-hydroxyisoxazolyl, 3-hydroxyisothiazolyl, pyrimidine, 3,5-difluoro-4-hydroxyphenyl or 2,4-difluoro-3-hydroxyphenyl, all of which can be optionally further substituted, and $R^1$ is alkoxy or oxo using synthetic procedures described in WO 2017/062763, US20160130297, US20160145295, US20160145296, US20160185815, US20160229886, US20160289262, and WO2018/081285 or using other procedure known in the art.

For example, compounds where $R^7$ is tetrazolyl, oxadiazolyl, thiadiazolyl, 5-oxo-1,2,4-oxadiazolyl, 5-oxo-1,2,4-thiadiazolyl, oxazolidinedionyl, thiazolidinedionyl, 3-hydroxyisoxazolyl, 3-hydroxyisothiazolyl, or 2,4-difluoro-3-hydroxyphenyl can be prepared from the corresponding carboxylic acid via a coupling with the required $R^7$-containing boronic acids:

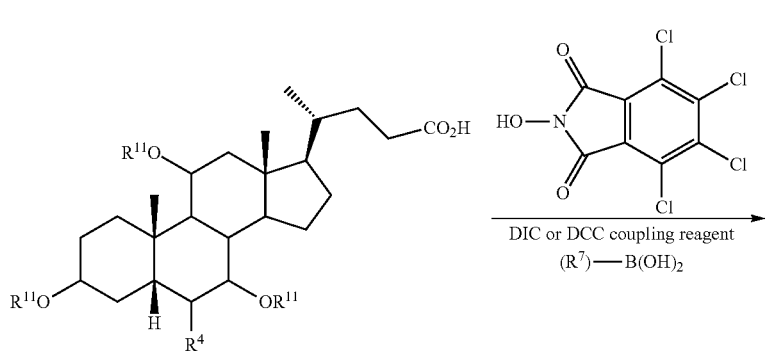

(1)

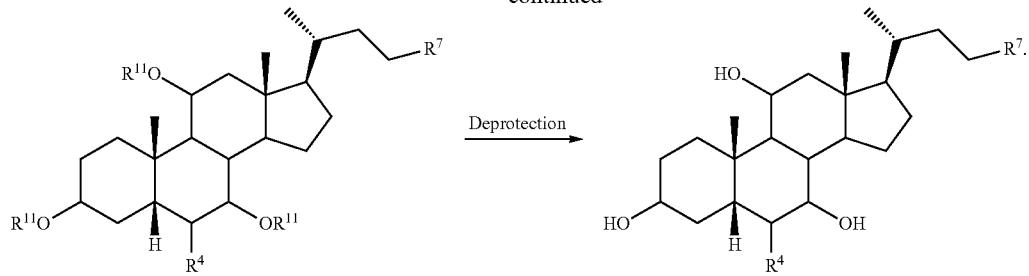

In some embodiments, $R^{11}$ protecting group is selected from $C(O)C_1$-$C_4$ alkyl, $C_1$-$C_6$ alkoxycarbonyl, optionally substituted aryloxycarbonyl, benzoyl, benzyl, pivaloyl, tetrahydropyranyl ether, tetrahydrofuranyl, 2-methoxyethoxymethyl ether, methoxymethyl ether, ethoxyethyl ether, p-methoxybenzyl ether, methylthiomethyl ether, triphenylmethyl, dimethoxytrityl, methoxytrityl, and silyl ether. In one embodiment, the silyl ether is selected from trimethylsilyl ether, triethylsilyl ether, triisopropylsilyl ether, tert-butyldimethylsilyl ether, and tert-butyldiphenylsilyl ether. In one embodiment, the $R^{11}$ protecting group is benzoyl or acetyl. In one embodiment, the $R^{11}$ protecting group is $C(O)C_1$-$C_4$ alkyl. In one embodiment, the $R^{11}$ protecting group is acetyl. In some embodiments $R^{11}$ is H.

Compounds of formula I can be prepared in 6 to 9 steps with overall yield of about 40 to about 60%. In one of the embodiments, the overall yield of compound of formula I, I-9 or C2 is about 50%. Various modifications to the process of Scheme A or Scheme A-I are disclosed in Schemes 1-13. In some of the aspects, the present disclosure relates to a method of preparing the compound of formula B from the compound of formula A1 in one step, the method comprising the steps shown in Scheme 2.

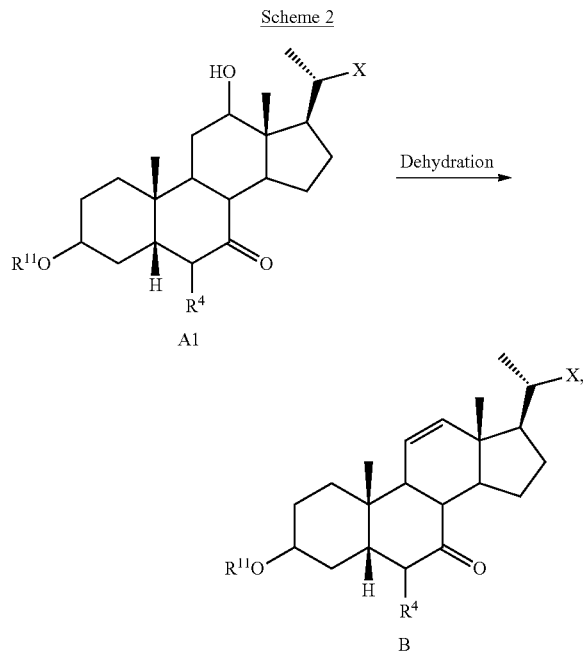

wherein $R^4$, $R^{11}$ and X are as described herein.

In some embodiments, the step of Scheme 2 is performed on a C7-protected compound, as, for example, shown in Scheme 2a.

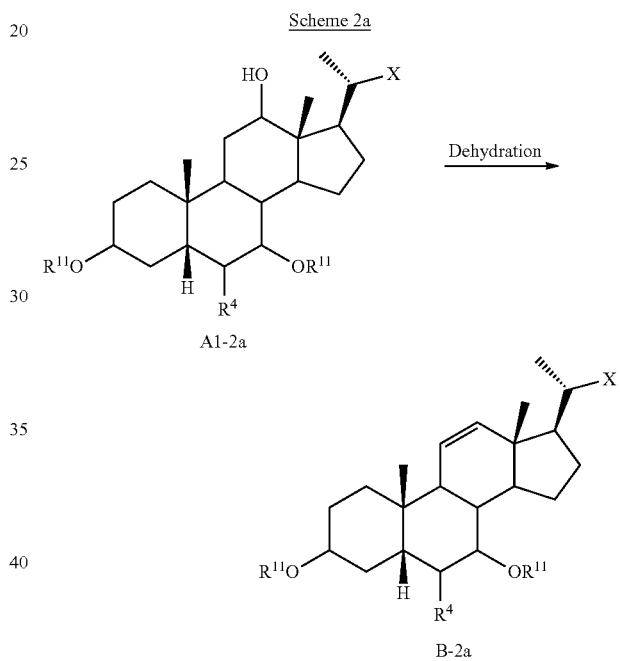

In some embodiments, the compound of formula A1 is treated with a dehydrating reagent (e.g., phosphorus oxychloride ($POCl_3$), $PCl_5$, $P_2O_5$, Burgess reagent, dicyclohexylcarbodiimide (DCC), 2-chloro-1,3-dimethylimidazolinium chloride (DMC), $H_3PO_4$, etc.) in the presence of a base (e.g., pyridine, lutidine, triethylamine, diisopropylethyl amine, LiBr, $Li_2CO_3$, AcOK, trimethylpyridine, etc.) to provide the compound of formula B. In some embodiments, the reaction is carried out at about 40° C., about 45° C., about 50° C., about 55° C., or about 60° C. In some embodiments, the compound of formula B prepared by the dehydration reaction is obtained in about 60%, about 70%, about 75%, about 80%, about 85%, about 90%, about 95% or more than 95% yield. The compound of formula B can be purified (e.g., by chromatography or crystallization) or used for the next step without purification. In one of the embodiments, the compound of formula B is crystallized and optionally recrystallized. In one of the embodiments, the compound of formula B is used without purification.

In some embodiments, the compound of formula A1 is first converted into the compound of formula A2 as shown in step 2 of Scheme 1. In some embodiments, C12-alcohol A1 is treated with an activating reagent (or an electrophile, e.g., mesyl (methanesulfonyl) chloride, tosyl (toluenesulfonyl) chloride, trifluoromethanesulfonic (triflic) anhydride, thionyl chloride, $SO_3$-pyridine, phosphoryl chloride, phosphoryl bromide, nonafluorobutanesulfonyl chloride, or any other reagent providing a suitable leaving group at C12 position) in the presence of a base (e.g., pyridine, triethylamine, diisopropylethylamine (DIPEA), imidazole, etc.) at about 20° C., about 25° C., about 30° C., about 35° C., about 40° C., about 45° C., about 50° C., about 55° C., about 60° C., about 65° C. or up to the reflux temperature of an appropriate reaction solvent (e.g., pyridine, methylene chloride (DCM), etc.). In some embodiments, an additional base can be used as a nucleophilic catalyst (e.g., 4-dimethylaminopyridine (DMAP)).

In some embodiments, about 2 equivalents, about 3 equivalents, about 4 equivalents, about 5 equivalents, about 6 equivalents, about 7 equivalents, about 8 equivalents, about 9 equivalents, or about 10 equivalents of the base are used (molar equivalents, based on molar amount of the compound of formula A1). In some embodiments, about 2 equivalents, about 2.5 equivalents, about 3 equivalents, about 3.5 equivalents, about 4 equivalents, about 4.5 equivalents, about 5 equivalents, about 5.5 equivalents, or about 6 equivalents of the activating reagent (electrophile) are used (molar equivalents, based on molar amount of the compound of formula A1).

In some embodiments, the compound of formula A2 is prepared in about 50%, about 60%, about 70%, about 80%, about 85%, about 90%, about 95% or more than 95% yield. In one of the embodiments, the compound of formula A2 can be prepared in quantitative yield, e.g., about 100%. In one of the embodiments, the compound of formula A2 is used without purification.

In some embodiments, the compound of formula A2 is treated with a suitable base to provide the compound of formula B. In some embodiments, suitable bases include, but are not limited to, metal alkoxides (e.g., potassium tert-butoxide (t-BuOK), sodium amylate, etc.), acetate salts (e.g., potassium acetate (KOAc), lithium acetate (LiOAc), sodium acetate (NaOAc), or cesium acetate (CsOAc)), 1,8-diazabicyclo[5.4.0]undec-7-ene (DBU), imidazole, pyridine, etc.

In some embodiments, elimination reaction of step 3 of Scheme 1, is carried out in a suitable solvent, such as a high-boiling solvent (e.g., hexamethylphosphoramide (HMPA), 1,3-dimethyl-3,4,5,6-tetrahydro-2-pyrimidinone (DMPU), 1,3-dimethyl-2-imidazolidinone (DMI), dimethyl sulfoxide (DMSO), dimethylformamide (DMF), dimethylacetamide (DMA), N-methyl-2-pyrrolidone (NMP), etc.) or a low boiling solvent (e.g., DCM, methyl tert-butyl ether (MTBE), tetrahydrofuran (THF), etc.) at elevated temperatures, for example, at about 80° C., about 90° C., about 100° C., about 110° C., about 120° C. or at reflux temperature of the reaction solvent.

In some embodiments, the compound of formula B is prepared in about 60%, about 70%, about 80%, about 85%, about 90%, about 95% or more than 95% yield. In one of the embodiments, the compound of formula B can be prepared in quantitative yield, e.g., about 100%. In one of the embodiments, the compound of formula B is used without purification. In some of the embodiments, the compound of formula B is purified by chromatography or crystallization. In one of the embodiments, the compound of formula B is crystallized from a suitable organic solvent (e.g., heptanes, n-heptane, hexanes, ethyl acetate, methanol, water). In one of the embodiments, purity of the isolated compound of formula B is about 80%, about 85%, about 90%, about 95% or more than 95% (by weight). In one of the embodiments, purity of the compound of formula B is about 97%. In one of the embodiments, purity of the compound of formula B is more than about 97%.

Some embodiments of the present disclosure relate to methods of converting the compound of formula B into the compound of formula C. In certain embodiments, the compound of formula B is treated with an oxidizing agent to provide the compound of formula C in a single step (step 4a):

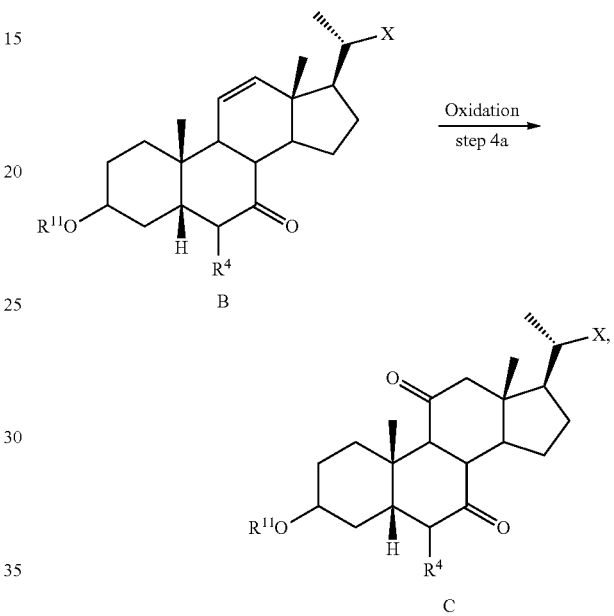

wherein $R^4$, $R^{11}$ and X are as described herein.

In some embodiments, the oxidation step can be performed on C-7 protected compounds, wherein $C_7$ is $OR^{11}$.

In certain embodiments, the compound of formula B is contacted with a metal salt or metal complex (e.g., salts or complexes of ruthenium, rhodium, vanadium, molybdenum, platinum, iron, iridium, etc.), in the presence of an oxidant (e.g., molecular oxygen, hydrogen peroxide, tert-butyl hydroperoxide, etc.) to generate the compound of formula C.

In one of the embodiments, the compound of formula C can be prepared via Wacker-type oxidation. The compound of formula B in a suitable organic solvent (e.g., dimethylformamide, dimethylacetamide, 1,2-diethoxyethane, etc.), optionally containing water, is treated with a catalytic amount of a palladium salt (e.g., $PdCl_2$, $Pd(Quinox)Cl_2$, etc.), optionally in the presence of a copper salt (e.g., CuCl, $CuCl_2$, $Cu(OAc)_2$, etc.) or a silver salt (e.g., AgOAc, $AgSbF_6$, etc.), and an oxidant (e.g., molecular oxygen, tert-butyl hydrogen peroxide, etc.) to provide the compound of formula C.

In one of the embodiments, the compound of formula B is contacted with a metal salt or metal complex (e.g., salts or complexes of ruthenium, rhodium, vanadium, molybdenum, platinum, iron, iridium, etc.) in the presence of an oxidant (e.g., molecular oxygen, hydrogen peroxide, tert-butyl hydroperoxide, etc.) to provide the compound of formula C. In one of the embodiments, the compound of formula B is contacted with a bromide containing salt (e.g., LiBr, NaBr, KBr, CsBr, tetraalkylammonium bromide, etc.) and an oxidant (e.g., $H_2O_2$, Oxone or other salts of peroxysulfate, mCPBA, peracetic acid, sodium periodate, periodic acid, etc.) to provide the compound of formula C. Suitable solvents include, but are not limited to acetone, acetic acid, and mixture thereof. Optionally, solvents used for bromination may contain water.

In one of the embodiments, the compound of formula B is contacted with a hypobromite salt (e.g., LiOBr, NaOBr, KOBr, tetraalkylammonium hypobromite, $Ca(OBr)_2$, etc.), or bromite salt (e.g., $LiO_2Br$, $NaO_2Br$, $KO_2Br$, tetraalkylammonium hypobromite, $Ca(BrO_2)_2$, etc.) in a suitable organic solvent (e.g., acetone, acetic acid, etc.), optionally in the presence of water, to generate the compound of formula C. In some of the embodiments, the present disclosure relates to a method of preparing the compound of formula C as shown in Scheme 1 and Scheme 3.

wherein $R^4$, $R^{11}$ and X are as described herein. According to Scheme 3, the process of preparing the compound of formula C comprises the steps of 4) reacting the compound of formula B with a brominating reagent to provide the compounds of formula B1;
5) reacting the compound of formula B1 with an oxidizing agent to prepare the compound of formula B2; and
6) reacting the compound of formula B2 with a reducing agent to prepare the compound of formula C (reductive debromination).

In certain embodiments, the disclosure relates to a method of making the compound C according to Scheme 3A comprising the following steps:

1) contacting the compound of formula B with a halogenation reagent (e.g., N-bromosuccinimide, N-iodosuccinimide, etc.) in the presence of an alcohol (e.g., methanol, ethanol, isopropanol, etc.) to form an intermediate a vicinal halo (e.g., bromo or iodo) ether of formula B' (step 4b);
2) treating of the vicinal halo (e.g., bromo or iodo) ether B' with a suitable base (e.g., DBU, triethyl amine, metal alkoxide bases, etc.) to generate an alkoxy enol ether B" via elimination of the halogen (step 5b); and
3) treating of the alkoxy enol ether with an acid in the presence of water, compound of formula C is generated by hydrolyzing the alkoxy enol ether B" (step 6b).

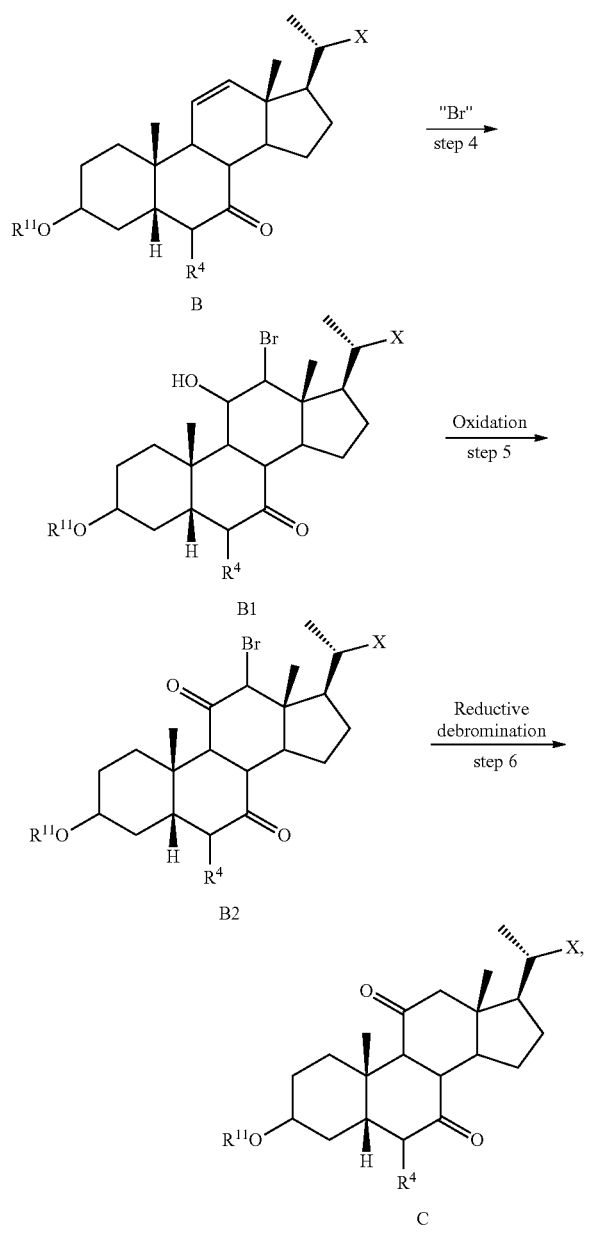

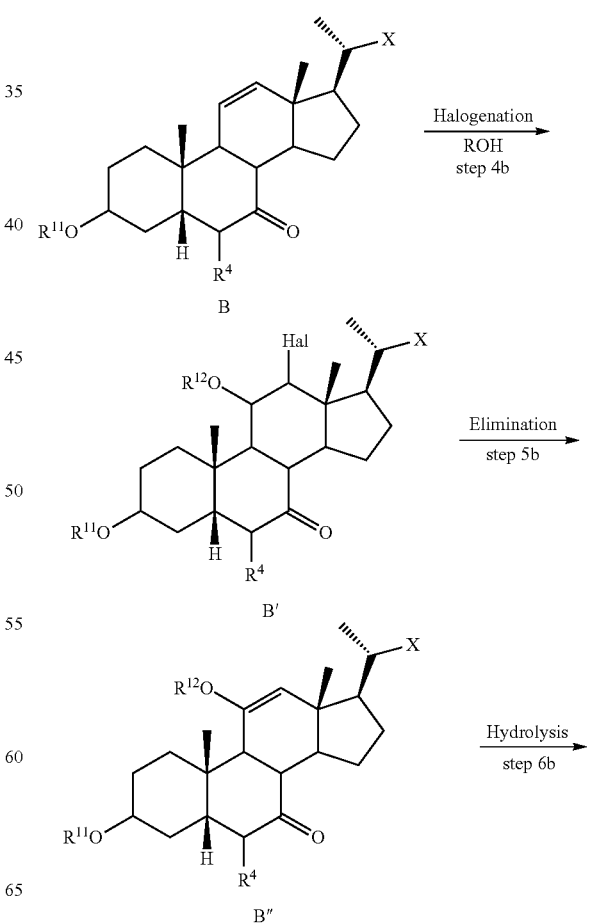

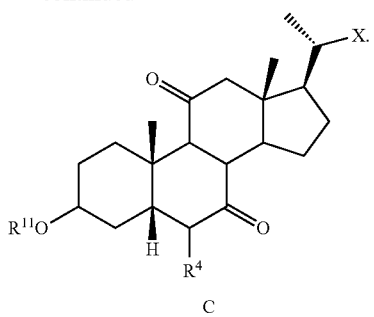

C wherein $R^{12}$ is alkyl and X, $R^4$ and $R^{11}$ are as described herein.

In some embodiments, the present disclosure relates to a method of preparing the compound of formula C as shown in Scheme 3B.

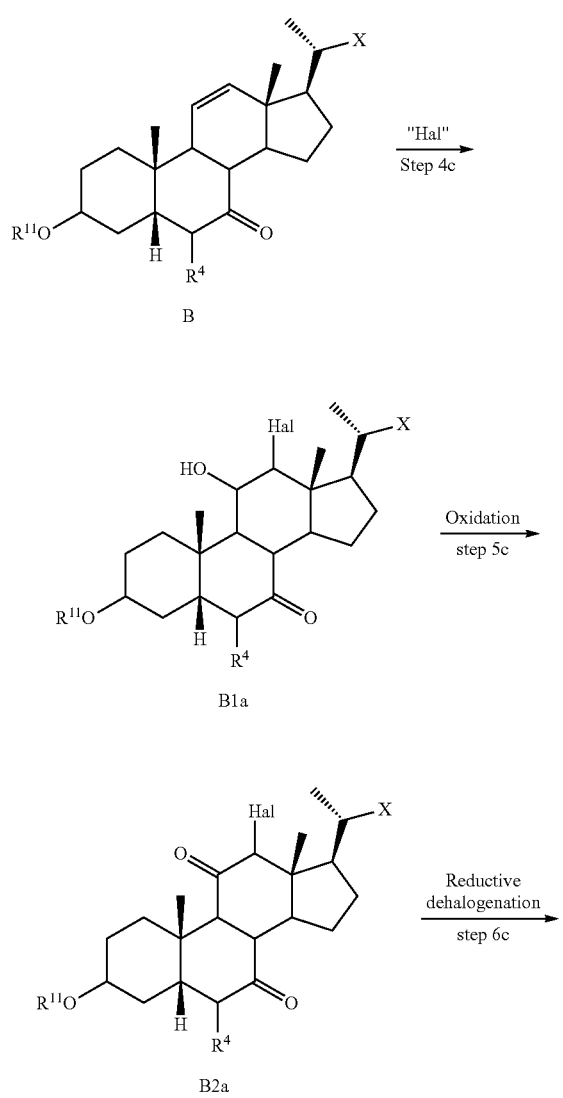

Scheme 3B

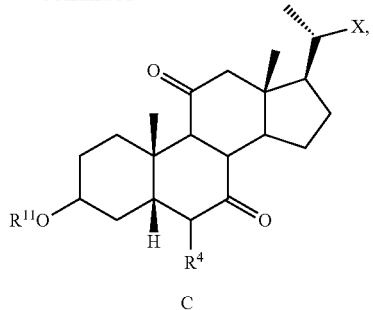

C wherein $R^4$, $R^{11}$ and X are as described herein.

According to Scheme 3B, the process of preparing the compound of formula C comprises the steps of
4) reacting the compound of formula B with a halogenating (e.g., brominating or iodinating) reagent to provide the compounds of formula B1a (step 4c);
5) reacting the compound of formula B1a with an oxidizing agent to prepare the compound of formula B2a (step 5c); and
6) reacting the compound of formula B2a with a reducing agent to prepare the compound of formula C (step 6c; reductive halogenation, e.g., debromination or deiodination).

The present disclosure also relates to the methods described herein which alternatively apply to C7 pretected compounds, i.e. C7 is substituted with $OR^{11}$ instead of oxo group.

Some embodiments of the present disclosure relate to the manipulation of protection and/or deprotection steps for the ease of purification (e.g., by crystallization) of intermediates. In some embodiments, the presence of $R^7$ as methyl ester protected COOH facilitates purification of intermediates including the penultimate intermediate. In some embodiments, retention of the protecting group at C3 facilitates the purification of intermediates including the penultimate compounds.

In certain embodiments, the compound of formula B in a suitable organic solvent (e.g., THF, acetonitrile (ACN), methyl acetate (AcOMe), dichloromethane (DCM), acetone, etc. or mixtures thereof) optionally containing water and/or optionally containing a buffer salt (e.g., potassium phosphate, sodium acetate, sodium bicarbonate, etc.) is treated with a halogenating reagent (halogen donor reagent) to generate the compound of formula B1, B' or B1a. In some embodiments, halogenating reagent is brominating reagent (bromine donor reagent). In some embodiments, halogenating reagent is iodinating reagent (iodine donor reagent).

In certain embodiments, the compound of formula B in a suitable organic solvent (e.g., THF, acetonitrile (ACN), methyl acetate (AcOMe), dichloromethane (DCM), acetone, etc. or mixtures thereof) optionally containing water and/or optionally containing a buffer salt (e.g., potassium phosphate, sodium acetate, sodium bicarbonate, etc.) is treated with a brominating agent (bromine donor reagent) to generate the compound of formula B1.

In certain embodiments, the solvent is a mixed solvent system. In some of the embodiments, the solvent is a THF/water, AcOMe/water, or ACN/water system. In one of the embodiments, the solvent is an acetonitrile-water system. In one of the embodiments, the solvent is a THF-water system. In one of the embodiments, the solvent is a methyl acetate-water system. In certain embodiments, the solvents in a mixed solvent system are mixed in a fixed ratio, including, but not limited to e.g., 5:1, 4.5:1, 4:1, 3.5:1, 3:1, 2.5:1, 2:1, 1.5:1, or 1:1 (organic solvent:water). In a further embodiment, the solvent is a three-solvent system. In one of the embodiments, the solvent system is acetone-THF-water. In certain embodiments, the solvents in a mixed three-solvent system are mixed in a fixed ratio, including but not limited to e.g. 1.5:3:1, 1:3:1.5, or 1:3:1, 1.5:4:1, 1:4:1.5, 1:4:1, 1.5:5:1, 1:5:1.5, 1:5:1 (organic solvent 1:organic solvent 2:water).

In some embodiments, the brominating reagent is an electrophilic brominating reagent. In one of the embodiments the brominating reagent is bromine. The brominating reagents or bromine donor reagents are commercially available or can be easily synthesized by a skilled artisan. The electrophilic brominating reagents include, but are not limited to, phenylselenium bromide, phenylselenium tribromide, pyridinium tribromide, N-bromophthalimide, N-bromosaccharine, acetylhypobromite, N-bromacetamide, tetramethylammonium tribromide, dibromohydantoin (DDH, 1,3-dibromo-5,5-dimethylhydantoin (DBDMH)), tribromoisocyanuric acid, dibromoisocyanuric acid, dibromamine-T (N,N-dibromo-p-toluenesulfonamide), dibromamine-B, N-bromosuccinimide (NBS), dimethylaminopyridine bromide, and bromodichloroisocyanuric acid (BDCCA):

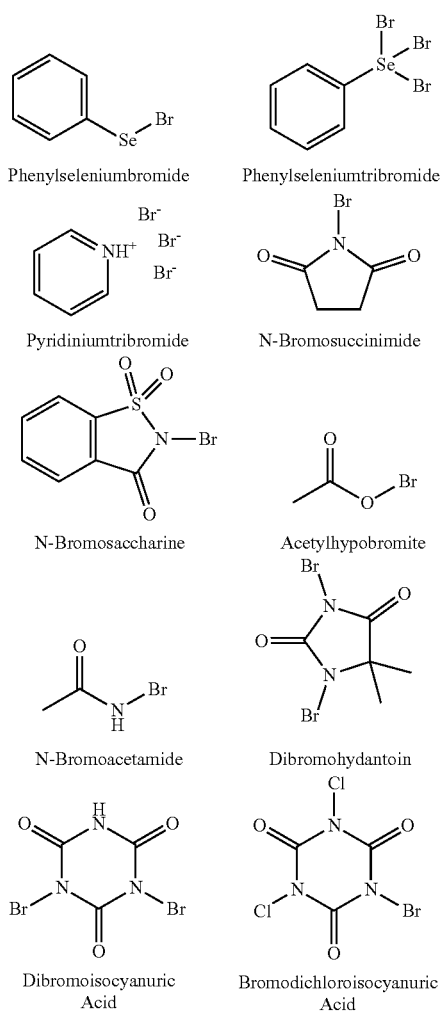

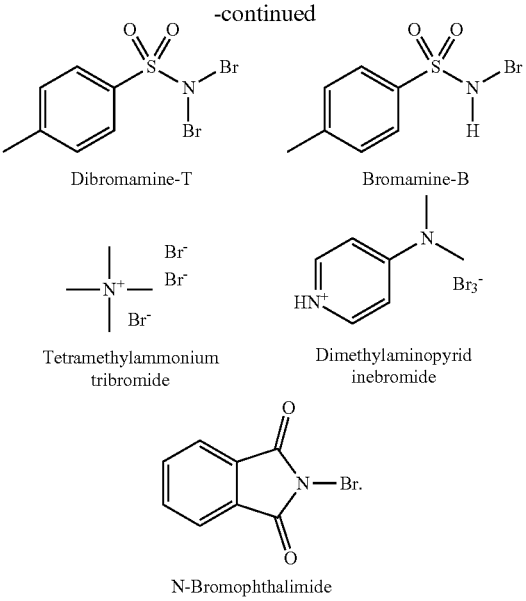

In certain embodiments, the brominating agent (reagent or donor) is dibromohydantoin (1,3-dibromo-5,5-dimethylhydantoin (DBDMH)), N-bromosuccinimide (NBS), N-bromosaccharine, dibromamine-T or bromodichloroisocyanuric acid (BDCCA). In one of the embodiments, the brominating reagent is dibromamine-T. In another embodiment, the brominating reagent is 1,3-dibromo-5,5-dimethylhydantoin (DBDMH). In another embodiment, the brominating reagent is NBS. In one of the embodiments NBS is used in combination with NH$_4$OAc (e.g., catalytic, about 0.1 to about 0.2 equivalents (eq.), including about 0.11, about 0.12, about 0.13, about 0.14, about 0.15, about 0.16, about 0.17, about 0.18, about 0.19, or about 0.2 eq.). In some embodiments, the stoichiometry of the brominating reagent is from about 1.0 to about 2.5 eq., including about 1.05, about 1.1, about 1.15, about 1.2, about 1.25, about 1.3, about 1.35, about 1.4, about 1.45, about 1.5, about 1.55, about 1.6, about 1.65, about 1.7, about 1.75, about 1.8, about 1.85, about 1.9, about 2.0, about 2.05, about 2.1, about 2.15, about 2.2, about 2.25, about 2.3, about 2.35, about 2.4, about 2.45, or about 2.5 eq.

In one aspect of the invention, the brominating reagent is optionally used in the presence of a nucleophilic organocatalyst. The nucleophilic organocatalysts include, but not limited to, dimethylformamide, dimethylacetamide, tetramethylguanidine, dimethylaminopyridine, and N-bromoamidine (e.g. ±-iso-amarine).

In some embodiments, the bromohydration (hydroxybromination) reaction of step 4 is carried out at about −50° C., about −40° C., at about −30° C., at about −20° C., at about −10° C., at about −5° C., at about 0° C., at about 5° C., at about 10° C., at about 15° C., or at about 20° C.

In certain embodiments, the bromohydration reaction of step 4 is carried out at about 5° C. to about 10° C.

In some embodiments, the compound of formula B1, bromohydrin, is obtained in about 50%, in about 55%, about 60%, in about 65%, about 70%, about 75%, about 80%, about 85%, about 90%, about 95% or more than 95% yield. In one of the embodiments, the compound of formula B1 can be purified or used without purification. In one of the embodiments, compound B1 is obtained in about 63% yield using methyl acetate-water solvent system.

In some embodiments, the compound of formula B1 is treated with a reducing agent (e.g., sodium bisulfite, sodium thiosulfate, trimethylphosphite, etc.) to stabilize compound of formula B1 during work-up and isolation. In certain embodiments, the reducing agent is a mild reducing agent. In one of the embodiments, the reducing agent can be substituted with additional oxidant (e.g., NaOCl, tert-butyl hydroperoxide, hydrogen peroxide, peracetic acid, sodium periodate, etc.), and optionally in the presence of an oxidation catalyst (e.g., chromium salts, TEMPO, etc.), to generate the compound of formula B2, without isolation of compound of formula B1. The product can be extracted into a suitable organic solvent (e.g., ethyl acetate, meth tert-butyl ether, dichloromethane, etc.) and concentrated as needed for the next reaction steps.

In some embodiments, the halogenating reagent is an electrophilic halogenating reagent. In some embodiments, the iodinating reagent is an electrophilic iodinating reagent. In one of the embodiments the iodinating reagent is iodine. In another embodiment, the iodinating reagent is N-iodosuccinimide (NIS). The halogenating reagents (e.g., brominating or iodinating reagents) are commercially available or can be easily synthesized by a skilled artisan. The iodinating reagents or iodine donor reagents are commercially available or can be easily synthesized by a skilled artisan. The electrophilic iodinating reagents include, but are not limited to, HOI generated in situ from iodine in the presence of water, iodine in the presence of aqueous cerium sulfate, $NaIO_4$ with sodium bisulfite, N-iodosuccinimide, I—Cl, I—F, etc., with or without an oxidizing agent (e.g., $HIO_3$, $HIO_4$, $H_5IO_6$, $HClO_4$, $HNO_3$, $H_2SO_4$, trifluoroacetic acid, trichloroacetic acid, etc).

In certain embodiments, the iodinating agent (reagent or donor) is N-iodosuccinimide (NIS). In one of the embodiments NIS is used in combination with catalytic or non-catalytic $H_5IO_6$, $HClO_4$, or $H_2SO_4$ (e.g., catalytic, about 0.1 to about 0.3 equivalents (eq.), including about 0.11, about 0.12, about 0.13, about 0.14, about 0.15, about 0.16, about 0.17, about 0.18, about 0.19, about 0.2 eq, about 0.21 eq, about 0.22 eq, about 0.23 eq, about 0.24 eq, about 0.25 eq, about 0.26 eq, about 0.27 eq, about 0.28 eq, about 0.29 eq, about 0.3 eq, or non-catalytic, at or above 1.0 eq). In some embodiments, the stoichiometry of the iodinating reagent is from about 1.0 to about 2.5 eq., including about 1.05, about 1.1, about 1.15, about 1.2, about 1.25, about 1.3, about 1.35, about 1.4, about 1.45, about 1.5, about 1.55, about 1.6, about 1.65, about 1.7, about 1.75, about 1.8, about 1.85, about 1.9, about 2.0, about 2.05, about 2.1, about 2.15, about 2.2, about 2.25, about 2.3, about 2.35, about 2.4, about 2.45, or about 2.5 eq.

In certain embodiments, the compound of formula B in a suitable organic solvent (e.g., THF, acetonitrile (ACN), methyl acetate (AcOMe), dichloromethane (DCM), acetone, methyl tert-butyl ether (MTBE), dioxane etc. or mixtures thereof) optionally containing water and/or optionally containing a buffer salt (e.g., potassium phosphate, sodium acetate, sodium bicarbonate, etc.) is treated with an iodination agent (iodine donor reagent) to generate the compound of formula B1a.

In certain embodiments, the solvent is a mixed solvent system. In some of the embodiments, the solvent is a dioxane/water, MTBE/water, or ACN/water system. In one of the embodiments, the solvent is a dioxane-water system. In one of the embodiments, the solvent is a MTBE-water system containing trifluoroacetic acid. In one of the embodiments, the solvent is a MTBE-water system. In certain embodiments, the solvents in a MTBE-water system are mixed in a fixed ratio, including, but not limited to e.g., 20:1, 19:1, 18:1, 17:1, 16:1, 15:1, 14:1, 13:1, 12:1, 11:1, 10:1, 9:1, 8:1, 7:1, 6:1, 5:1, 4.5:1, 4:1, 3.5:1, 3:1, 2.5:1, 2:1, 1.5:1, or 1:1 (organic solvent:water). In certain embodiments, the solvents in a dioxane-water system are mixed in a fixed ratio, including, but not limited to e.g., 10:1, 9:1, 8:1, 7:1, 6:1, 5:1, 4.5:1, 4:1, 3.5:1, 3:1, 2.5:1, 2:1, 1.5:1, or 1:1 (organic solvent:water).

In some embodiments, the iodohydration (hydroxy-iodination) reaction of step 4 is carried out at about −10° C., about −5° C., at about 0° C., at about 5° C., at about 10° C., at about 15° C., at about 20° C., at about 25° C., at about 30° C., at about 35° C., at about 40° C., at about 45° C., or 50° C.

In certain embodiments, the iodohydration reaction of step 4 is carried out at about 0° C. to about 5° C.

In some embodiments, the compound of formula B1a, (e.g., iodohydrin when Hal is iodo), is obtained in about 50%, in about 55%, about 60%, in about 65%, about 70%, about 75%, about 80%, about 85%, about 90%, about 95% or more than 95% yield. In one of the embodiments, the compound of formula B1a can be purified or used without purification. In one of the embodiments, compound B1a is obtained in about 90% yield using dioxane-water solvent system.

In some embodiments, the compound of formula B1a is treated with a reducing agent (e.g., sodium bisulfite, sodium thiosulfate, trimethylphosphite, etc.) to stabilize compound of formula B1a during work-up and isolation. In certain embodiments, the reducing agent is a mild reducing agent. In one of the embodiments, the reducing agent can be substituted with additional oxidant (e.g., NaOCl, tert-butyl hydroperoxide, hydrogen peroxide, peracetic acid, sodium periodate, etc.), and optionally in the presence of an oxidation catalyst (e.g., ruthenium salts, chromium salts, TEMPO, etc.), to generate the compound of formula B2a, without isolation of compound of formula B1a. The product can be extracted into a suitable organic solvent (e.g., ethyl acetate, meth tert-butyl ether, dichloromethane, etc.) and concentrated as needed for the next reaction steps.

In certain embodiments, a compound of formula B1 in a suitable organic solvent (e.g., methyl tert-butyl ether, THF, dichloromethane, ethyl acetate, acetonitrile, etc.; or a mixture thereof), optionally containing water, is contacted with an oxidant to generate compound of formula B2. The product can be extracted into a suitable organic solvent (e.g., ethyl acetate, meth tert-butyl ether, dichloromethane, etc.) and concentrated as needed for the next reaction steps.

In certain embodiments, a compound of formula B1a (e.g., iodohydrin when Hal is iodo) in a suitable organic solvent (e.g., methyl tert-butyl ether, THF, dichloromethane, ethyl acetate, acetonitrile, etc.; or a mixture thereof), optionally containing water, is contacted with an oxidant to generate compound of formula B2a. The product can be extracted into a suitable organic solvent (e.g., ethyl acetate, meth tert-butyl ether, dichloromethane, etc.) and concentrated as needed for the next reaction steps.

In some embodiments, the oxidizing agents include, but are not limited to, chromic acid or chromium salts (e.g., $Na_2Cr_2O_7$), manganese salts (e.g., $KMnO_4$), silver salts (e.g., $Ag_2CO_3$), iron salts (e.g., $K_2FeO_4$), cerium salts (e.g., $Ce(SO_4)_2$), ruthenium salts (e.g., $Na_2RuO_4$), and N-bromo derivatives (e.g., N-bromosuccinimide, dimethyl dibromohydantoin, N-bromoacetamide, etc.) in stoichiometric excess, or in catalytic amounts in combination with a co-oxidant (e.g., ammonium nitrate, hydrogen peroxide, tert-butyl hydroperoxide, peracetic acid, NaOCl, $Ca(OCl)_2$, etc.). In some embodiments, the oxidizing agent can be employed in the absence of metal salts. In certain embodiments, the oxidant can be employed during the bromination step to directly convert the intermediate compound of formula B1 to a compound of formula B2.

In some embodiments, the oxidizing agents include, but are not limited to, chromic acid or chromium salts (e.g., $Na_2Cr_2O_7$), manganese salts (e.g., $KMnO_4$), silver salts (e.g., $Ag_2CO_3$), iron salts (e.g., $K_2FeO_4$), cerium salts (e.g., $Ce(SO_4)_2$), ruthenium salts (e.g., $Na_2RuO_4$), and N-halo derivatives (e.g., N-iodosuccinimide N-bromosuccinimide, dimethyl dibromohydantoin, N-bromoacetamide, etc.) in stoichiometric excess, or in catalytic amounts in combination with a co-oxidant (e.g., ammonium nitrate, hydrogen peroxide, tert-butyl hydroperoxide, peracetic acid, NaOCl, $Ca(OCl)_2$, etc.). In some embodiments, the oxidizing agent can be employed in the absence of metal salts. In certain embodiments, the oxidant can be employed during the halogenaion, e.g., iodination step to directly convert the intermediate compound of formula B1a to a compound of formula B2a.

The compound of formula B2, bromoketone, is obtained in about 80%, in about 85%, about 90%, in about 95%, or more than 95% yield. In one of the embodiments, the compound of formula B2 is prepared in quantitative yield, e.g., about 100%. In one of the embodiments, the compound of formula B2 can be purified or used without purification.

In some embodiments, compound of formula B2 in a suitable organic solvent (i.e., acetic acid, methanol, THF, etc.), optionally containing water, is contacted with a reducing agent to generate compound of formula C.

In some embodiments, the compound of formula B2a, haloketone (e.g, bromoketone or iodoketone), is obtained in about 80%, in about 85%, about 90%, in about 95%, or more than 95% yield. In one of the embodiments, the compound of formula B2a is prepared in quantitative yield, e.g., about 100%. In one of the embodiments, the compound of formula B2a can be purified or used without purification.

In some embodiments, compound of formula B2a in a suitable organic solvent (i.e., acetic acid, methanol, THF, etc.), optionally containing water, is contacted with a reducing agent to generate compound of formula C.

The suitable reducing agents include, but are not limited to organosilanes (e.g., triethylsilane, hexamethyldisilane, etc.), trialkyl phosphines (e.g., triethyl phosphine, tributyl phosphine, etc.), triphenyl phosphine, 1,3-dialkyl-2-phenyl-benzimidazolines (e.g., 1,3-dimethyl-2-phenylbenzimidazoline), iodide salts (e.g., LiI, NaI, KI, CsI, etc.) in the presence of a Lewis acid (e.g., $BF_3$), hydroiodic acid, zinc-copper couple, zero valent metals (e.g., $Li^0$, $Na^0$, $K^0$, $Ca^0$, $Al^0$, $Fe^0$, $Zn^0$, etc.) and their corresponding lower-valency metal salts (e.g., low valent salts of chromium, tin, samarium, manganese, titanium such as $CrCl_2$, $SnCl_2$, $SmI_2$, $Mn(OAc)_3$, $TiCl_3$, respectively), aniline or substituted anilines (e.g., $PhNH_2$, PhNHMe, etc.), and hydrogen in the presence of a catalyst (e.g., palladium, platinum, ruthenium, iron, nickel, etc.). In one of the embodiments, debromination is performed using Zn (dust) in the presence of acetate salt (e.g., AcONa) in a suitable solvent (e.g., AcOH) and elevated temperature (e.g., reflux). The diketone compound of formula C is obtained in about 70%, in about 75%, in about 80%, in about 85%, about 90%, in about 95%, or more than 95% yield. In one of the embodiments, the compound of formula C is prepared in quantitative yield, e.g., about 100%. In one of the embodiments, the compound of formula C can be purified or used without purification.

One of the embodiments of the present disclosure relates to a method of making compound of formula B2' comprising the steps shown in Scheme 4.

Scheme 4:

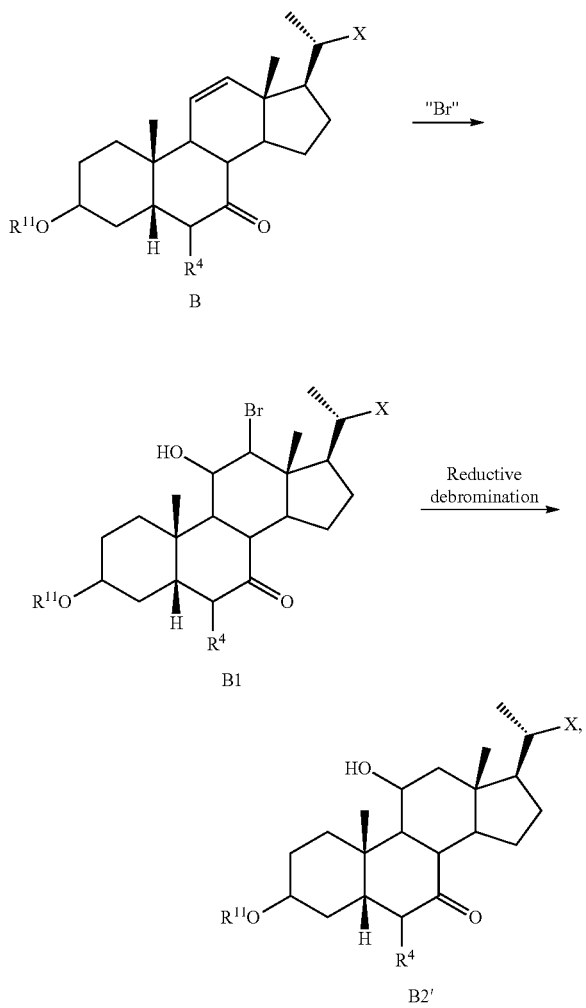

wherein $R^4$, $R^{11}$, and X are as described herein.

In one of the embodiments, the present disclosure relates to a method of making compound of formula B2' comprising the steps shown in Scheme 4A.

Scheme 4A:

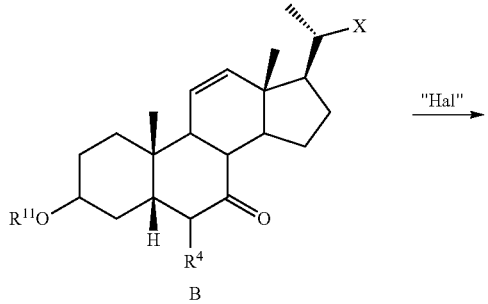

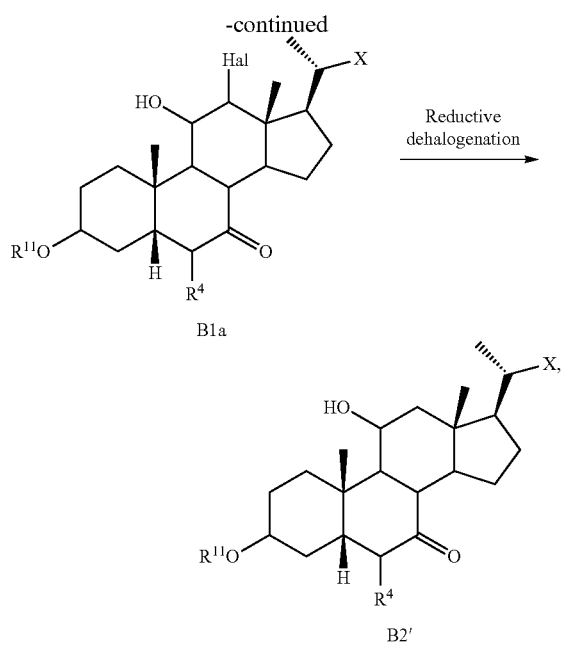

B1a

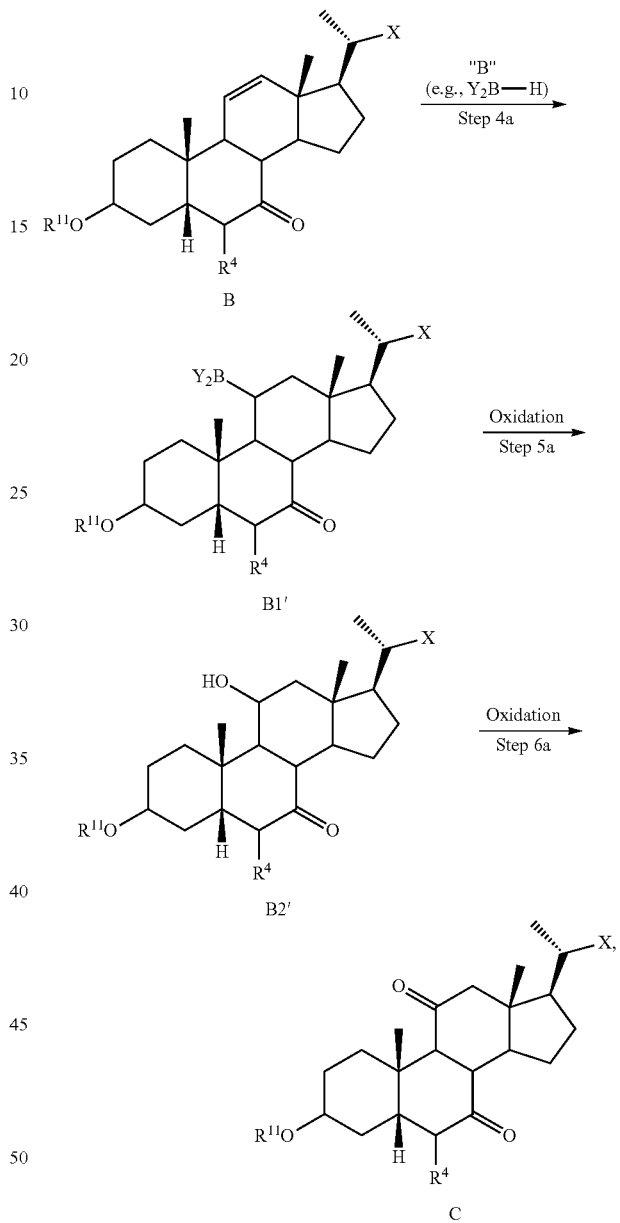

wherein $R^4$, $R^{11}$, and X are as described herein. Halogenated (e.g., brominated or iodinated) compound of formula B1a (halohydrin, e.g., bromohydrin or iodohydrin) in a suitable organic solvent (e.g., ethanol, acetic acid, etc. or mixture thereof) can be treated with a catalyst or metal reagent (e.g., Raney®-Nickel (Raney Ni or Ra—Ni) or zero valent zinc or magnesium), or optionally in the presence of hydrogen and a catalyst (e.g., Pd, Pt, Rh, Ni, and salts thereof, etc.), to generate a compound of formula B2'.

Halogenated compound of formula B1 or B1a (halohydrin or iodohydrin or bromohydrin) in a suitable organic solvent (e.g., ethanol, acetic acid, etc. or mixture thereof) can be treated with a catalyst or metal reagent (e.g., Raney®-Nickel, Raney Ni, Ra—Ni), or optionally in the presence of hydrogen and a catalyst (e.g., Pd, Pt, Rh, Ni, and salts thereof, etc.), to generate a compound of formula B2 or B2a. Brominated compound of formula B1 (bromohydrin) in a suitable organic solvent (e.g., ethanol, acetic acid, etc. or mixture thereof) can be treated with a catalyst or metal reagent (e.g., Raney®-Nickel, Raney Ni, Ra—Ni), or optionally in the presence of hydrogen and a catalyst (e.g., Pd, Pt, Rh, Ni, and salts thereof, etc.), to generate a compound of formula B2. In certain embodiments, reductive dehalogenation can be performed under neutral, basic or acidic conditions. In certain embodiments, the metal reagent can be used alone in stoichiometric amounts, or in catalytic amounts in the presence of hydrogen. In other embodiments, the reaction can be conducted under catalytic transfer hydrogenation using hydrogen donors (1,3-cyclohexadiene, 1,7-octadiene, cyclohexene, ammonium formate, potassium formate, formic acid, ethanol, i-propanol, etc.). In one of the embodiments, hydrogenation and catalytic transfer hydrogenation is performed under continuous flow conditions. The compound of formula B2' is obtained in about 70%, in about 75%, in about 80%, in about 85%, about 90%, in about 95%, or more than 95% yield. In one of the embodiments, the compound of formula B2' is prepared in quantitative yield, e.g., about 100%. In one of the embodiments, the compound of formula B2' can be purified or used without purification.

In one of the embodiments, the present disclosure relates to a method of making compound of formula C comprising the steps shown in Scheme 5.

Scheme 5:

wherein $R^4$, $R^{11}$, and X are as described herein and $BY_2$— is a boron moiety, where Y can be, for example, an alkyl group, halogen, hydrogen, amine, or alcohol.

The method of making of compound of formula C in Scheme 5 comprises the steps of:
 4a) reacting a compound of formula B with a borane reagent to prepare a compound of formula B1';
 5a) reacting the compound of formula B1' with an oxidizing reagent to provide a compound of formula B2'; and
 6a) reacting the compound of formula B2' with oxidizing reagent to prepare the compound of formula C.

In certain embodiments of the present disclosure, compound of formula B in an aprotic organic solvent (e.g., THF, dichloromethane, 1,2-diethoxyethane, heptane, etc.) is contacted with a borane reagent to form a compound of formula B1'. Upon completion of the reaction, the mixture is contacted with an oxidant to form a compound of formula B2' bearing an alcohol at C-11. The mixture can undergo work up via solvent extraction into a suitable organic solvent (e.g., ethyl acetate, dichloromethane, methyl tert-butyl ether, etc.), and the resulting solution is concentrated as needed, or solvent exchanged to a more appropriate solvent. A solution of compound of formula B2' is then contacted with an oxidant to generate compound of formula C.

The borane reagents ("B") include, but are not limited to $BH_3$ and complexes there of (e.g., $BH_3$-THF, $BH_3$-DMS, $BH_3$—$NH_3$, etc), monoalkylboranes of structure alkyl$BH_2$ (e.g., mono-thexyl borane, mono-isopinocampheyl borane, etc.), dialkylboranes of structure dialkylBH (e.g., disiamylborane, dithexylborane, dicyclopentylborane, 9-BBN, etc.), mono-chloroborane and complexes thereof (e.g., $ClBH_2$-THF, $ClBH_2$-DMS, etc.), dichloroborane and complexes thereof (e.g., $Cl_2BH$-THF, $Cl_2BH$-DMS, etc.), and catecholborane.

The oxidizing agents, for oxidizing the compound of formula B1', include, but are not limited to, hydrogen peroxide, tert-butyl hydroperoxide, Oxone, and molecular oxygen.

The oxidizing agents, for oxidizing the compound of formula B2' include, but are not limited to, chromic acid or chromium salts (e.g., $Na_2Cr_2O_7$), manganese salts (e.g., $KMnO_4$), silver salts (e.g., $Ag_2CO_3$), iron salts (e.g., $K_2FeO_4$), cerium salts (e.g., $Ce(SO_4)_2$), ruthenium salts (e.g., $Na_2RuO_4$), etc. in stoichiometric excess, or in catalytic amounts in combination with a co-oxidant (e.g., ammonium nitrate, hydrogen peroxide, tert-butyl hydroperoxide, peracetic acid, NaOCl, $Ca(OCl)_2$, $NaIO_4$, $H_5IO_6$, etc.). In some embodiments, the oxidizing agent can be employed in the absence of metal salts. In some embodiments, an oxidation catalyst, for example TEMPO, may be employed.

In some embodiments, the present disclosure relates to a method of preparing the compound of formula C2 according to the process of Scheme 5, wherein $R^4$, $R^{11}$, and X are as described herein.

Scheme 6:

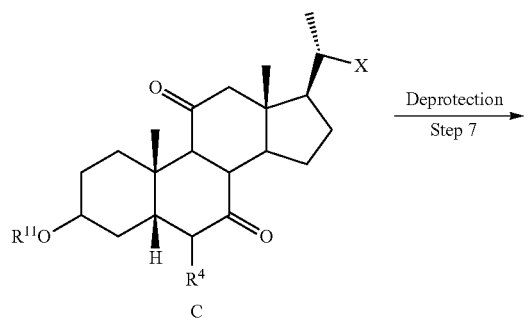

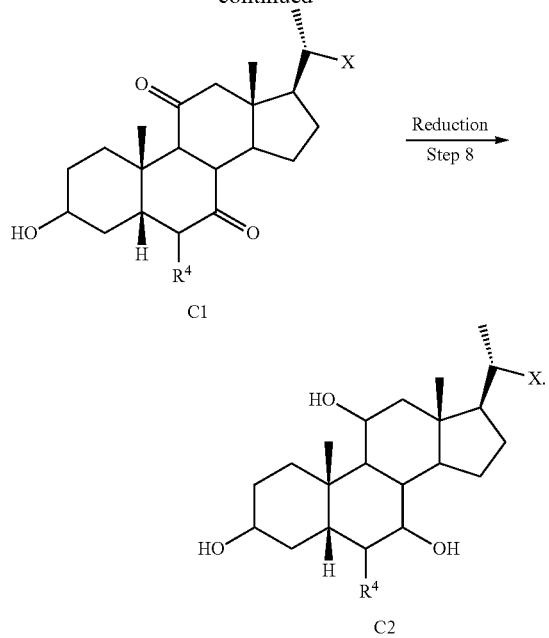

According to Scheme 6, the process of preparing the compound of formula C2 comprises the step of:
7) deprotecting compound of formula C to provide the compound of formula C1 or a pharmaceutically acceptable salt thereof; and
8) reacting the compound of formula C1 with a reducing reagent to prepare a compound of formula C2.

In some embodiments, the reducing reagents in step 8 include but are not limited to $NaBH_4$, $NaCNBH_3$, $LiBH_4$, $(i-Bu_2AlH)_2$, L-selectride, K-selectride. In one embodiment, the reducing reagent is $NaBH_4$ or $LiBH_4$. Reducing agents can be used in combination with added reagents such as, but not limited to $CeCl_3$, $CoCl_2$, and other Lewis acids, which can be used to enhance a ketone reduction, including, but are not limited to zinc(II), calcium(II), magnesium(II), aluminum(III) salts.

In some embodiments, at least 2 molar equivalents of the reducing agent are used. In some embodiments, from about 2 equivalents to about 3 equivalents of the reducing agent are used. In another embodiment, the molar ratio (or molar equivalent) is about 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 equivalents.

The reduction is performed in a suitable solvent. In one embodiment, the reduction is performed in water. In one embodiment, the reduction is performed in an alcoholic solvent. In one embodiment, the alcoholic solvent is methanol. In one embodiment, the alcoholic solvent is isopropanol. In one embodiment, the alcoholic solvent is ethanol. In some embodiments, reduction is performed in the presence of a base. In one embodiment, the base is sodium hydroxide. In one embodiment, the base is sodium hydroxide and the solvent is water.

In one embodiment, the reduction in step 8 is conducted in a time period between about 2 hours and about 50 hours, e.g., about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 25 hours, about 30 hours, about 35 hours, about 40 hours, about 45 hours, or about 50 hours.

In one embodiment, the reduction in step 8 is performed at a temperature from between about 15° C. and about 100° C., as well as any temperature increment in between, e.g., at about 20° C., at about 25° C., at about 30° C., at about 40° C., at about 50° C., at about 60° C., at about 70° C., at about 80° C., at about 90° C., or at about 100° C.

In one embodiment, the reduction is performed at a temperature from between about −10° C. and about 15° C., e.g., about −10° C., about −5° C., about 0° C., about 3° C., about 5° C., about 7° C., about 10° C. or about 15° C., as well as any temperature increment in between. In one embodiment, the reduction is performed at about 5° C.

Deprotection reagents for step 7 depend on the chosen protecting groups and can be selected from standard reagents known by those skilled in the art (including the reagents discussed herein).

In certain embodiments, the process of Scheme 1 provides a compound of formula II:

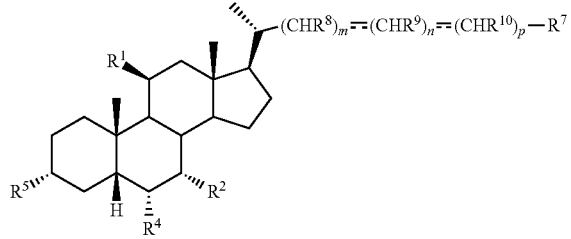

II or a pharmaceutically acceptable salt, solvate, or amino acid, sulfate or glucuronide conjugate or prodrug thereof.

In certain embodiments, the process of Scheme 1 provides a compound of formula III:

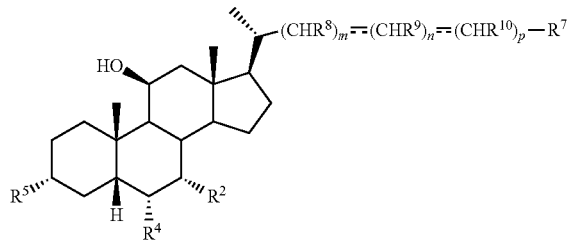

III or a pharmaceutically acceptable salt, solvate, or amino acid, sulfate or glucuronide conjugate or prodrug thereof.

In some embodiments, the present disclosure relates to a method of making a compound of formula IIIa:

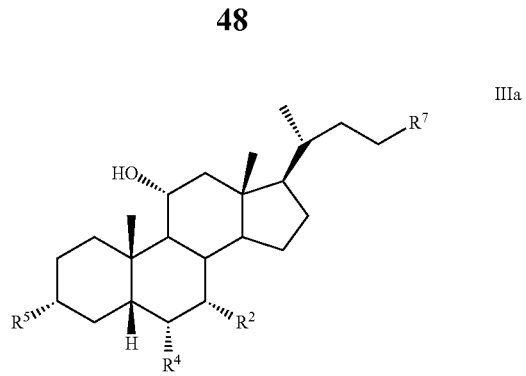

IIIa or a pharmaceutically acceptable salt, solvate, or amino acid, sulfate or glucuronide conjugate, or prodrug thereof.

In some embodiments, the present disclosure relates to a method of making a compound of formula IIIb:

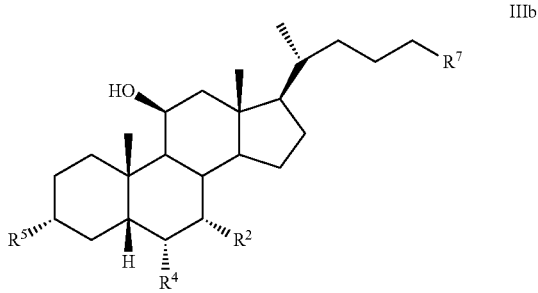

IIIb or a pharmaceutically acceptable salt, solvate, or amino acid, sulfate or glucuronide conjugate, or prodrug thereof.

In certain embodiments, the process of Scheme 1 provides a compound of formula 100:

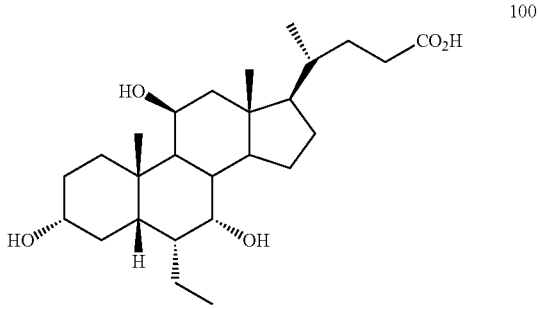 [SMILES: CC[C@H]1[C@@H](O)C2C3CC[C@H]([C@H](C)CCC(=O)O)[C@@]3(C)C[C@H](O)C2[C@@]2(C)CC[C@@H](O)C[C@@H]12]

100 or a pharmaceutically acceptable salt, solvate, or amino acid, sulfate or glucuronide conjugate, or prodrug thereof.

In one of the aspects, the present disclosure relates to a method of preparing a compound of formula Ia:

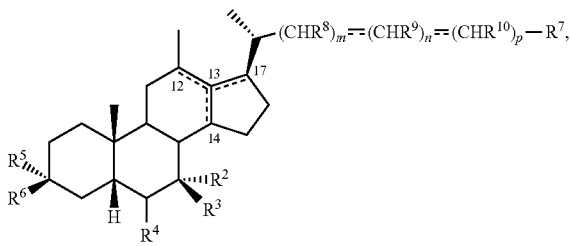

or a pharmaceutically acceptable salt, solvate, or amino acid, sulfate or glucuronide conjugate thereof, wherein:

dashed bond (—) represents either double or single bond, where a double bond exists between C12-C13, or C13-C14, or C13-C17;

$R^2$ and $R^3$ are each independently H, OH, $OSO_3H$, $OCOCH_3$, $OPO_3H_2$, halogen, or alkyl optionally substituted with one or more halogen or OH, or $R^2$ and $R^3$ taken together with the carbon atom to which they are attached form a carbonyl;

$R^4$ is H, halogen, alkyl optionally substituted with one or more halogen or OH, alkenyl, or alkynyl;

$R^5$ and $R^6$ are each independently H, OH, $OSO_3H$, $OCOCH_3$, $OPO_3H_2$, halogen, or alkyl optionally substituted with one or more halogen or OH, or $R^5$ and $R^6$ taken together with the carbon atom to which they are attached form a carbonyl;

$R^7$ is OH, $OSO_3H$, $SO_3H$, $OSO_2NH_2$, $SO_2NH_2$, $OPO_3H_2$, $PO_3H_2$, $CO_2H$, $C(O)NHOH$, $NH(CH_2)_2SO_3H$, $NHCH_2CO_2H$ or optionally substituted tetrazolyl, oxadiazolyl, thiadiazolyl, 5-oxo-1,2,4-oxadiazolyl, 5-oxo-1,2,4-thiadiazolyl, oxazolidine-dionyl, thiazolidine-dionyl, 3-hydroxyisoxazolyl, 3-hydroxyisothiazolyl, pyrimidine, 3,5-difluoro-4-hydroxyphenyl or 2,4-difluoro-3-hydroxyphenyl;

$R^8$, $R^9$, and $R^{10}$ are each independently H, OH, halogen, or alkyl optionally substituted with one or more halogen or OH, or $R^8$ and $R^9$ taken together with the carbon atoms to which they are attached form a 3- to 6-membered carbocyclic or heterocyclic ring comprising 1 or 2 heteroatoms selected from N, O, and S, or $R^9$ and $R^{10}$ taken together with the carbon atoms to which they are attached form a 3- to 6-membered carbocyclic or heterocyclic ring comprising 1 or 2 heteroatoms selected from N, O, and S;

m is 0, 1, or 2;
n is 0 or 1; and
p is 0 or 1.

In certain aspects, the compound of formula Ia is a compound of formula Ib:

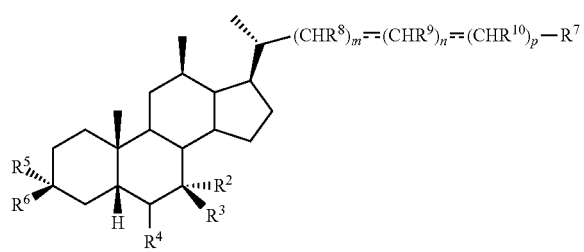

or a pharmaceutically acceptable salt, solvate, or amino acid, sulfate or glucuronide conjugate thereof, wherein:

$R^2$ and $R^3$ are each independently H, OH, halogen, or alkyl optionally substituted with one or more halogen or OH, or $R^2$ and $R^3$ taken together with the carbon atom to which they are attached from a carbonyl;

$R^4$ is H, halogen, alkyl optionally substituted with one or more halogen or OH, alkenyl, or alkynyl;

$R^5$ and $R^6$ are each independently H, OH, $OSO_3H$, $OCOCH_3$, $OPO_3H_2$, or halogen, or $R^5$ and $R^6$ taken together with the carbon atom to which they are attached form a carbonyl;

$R^7$ is OH, $OSO_3H$, $SO_3H$, $OSO_2NH_2$, $SO_2NH_2$, $OPO_3H_2$, $PO_3H_2$, $CO_2H$, $C(O)NHOH$, $NH(CH_2)_2SO_3H$, $NHCH_2CO_2H$ or optionally substituted tetrazolyl, oxadiazolyl, thiadiazolyl, 5-oxo-1,2,4-oxadiazolyl, 5-oxo-1,2,4-thiadiazolyl, oxazolidine-dionyl, thiazolidine-dionyl, 3-hydroxyisoxazolyl, 3-hydroxyisothiazolyl, pyrimidine, 3,5-difluoro-4-hydroxyphenyl or 2,4-difluoro-3-hydroxyphenyl;

$R^8$, $R^9$, and $R^{10}$ are each independently H, OH, halogen, or alkyl optionally substituted with one or more halogen or OH, or $R^8$ and $R^9$ taken together with the carbon atoms to which they are attached form a 3- to 6-membered carbocyclic or heterocyclic ring comprising 1 or 2 heteroatoms selected from N, O, and S, or $R^9$ and $R^{10}$ taken together with the carbon atoms to which they are attached form a 3- to 6-membered carbocyclic or heterocyclic ring comprising 1 or 2 heteroatoms selected from N, O, and S;

m is 0, 1, or 2;
n is 0 or 1; and
p is 0 or 1.

In some embodiments a compound of formula Ia or Ib is compound of formula D5

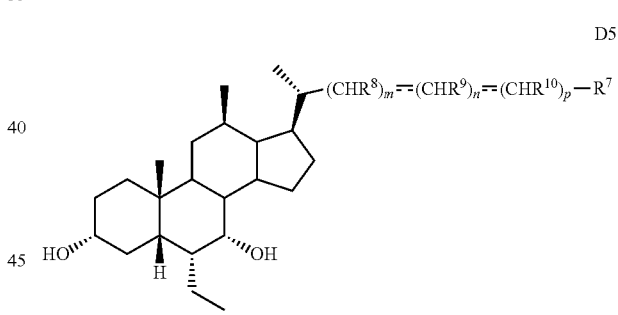

or pharmaceutically acceptable salt, hydrate, solvate or amino acid, sulfate or glucuronide conjugate, or prodrug thereof, wherein:

$R^7$ is OH, $OSO_3H$, $SO_3H$, $OSO_2NH_2$, $SO_2NH_2$, $OPO_3H_2$, $PO_3H_2$, $CO_2H$, $C(O)NHOH$, $NH(CH_2)_2SO_3H$, $NHCH_2CO_2H$ or optionally substituted tetrazolyl, oxadiazolyl, thiadiazolyl, 5-oxo-1,2,4-oxadiazolyl, 5-oxo-1,2,4-thiadiazolyl, oxazolidine-dionyl, thiazolidine-dionyl, 3-hydroxyisoxazolyl, 3-hydroxyisothiazolyl, pyrimidine, 3,5-difluoro-4-hydroxyphenyl or 2,4-difluoro-3-hydroxyphenyl;

$R^8$, $R^9$, and $R^{10}$ are each independently H, OH, halogen, or alkyl optionally substituted with one or more halogen or OH, or $R^8$ and $R^9$ taken together with the carbon atoms to which they are attached form a 3- to 6-membered carbocyclic or heterocyclic ring comprising 1 or 2 heteroatoms selected from N, O, and S, or $R^9$ and $R^{10}$ taken together with the carbon atoms to which they are attached form a 3- to 6-membered carbocyclic or heterocyclic ring comprising 1 or 2 heteroatoms selected from N, O, and S;

m is 0, 1, or 2;
n is 0 or 1; and
p is 0 or 1.

In some embodiments, the present disclosure relates to a method of making the compound of formula Ia (or Ib) having a structure of formula D5; the method comprising steps 1-8 as shown in Scheme 7. The compound of formula Ia (or Ib) can be prepared according to a synthetic scheme analogous to Scheme 7.

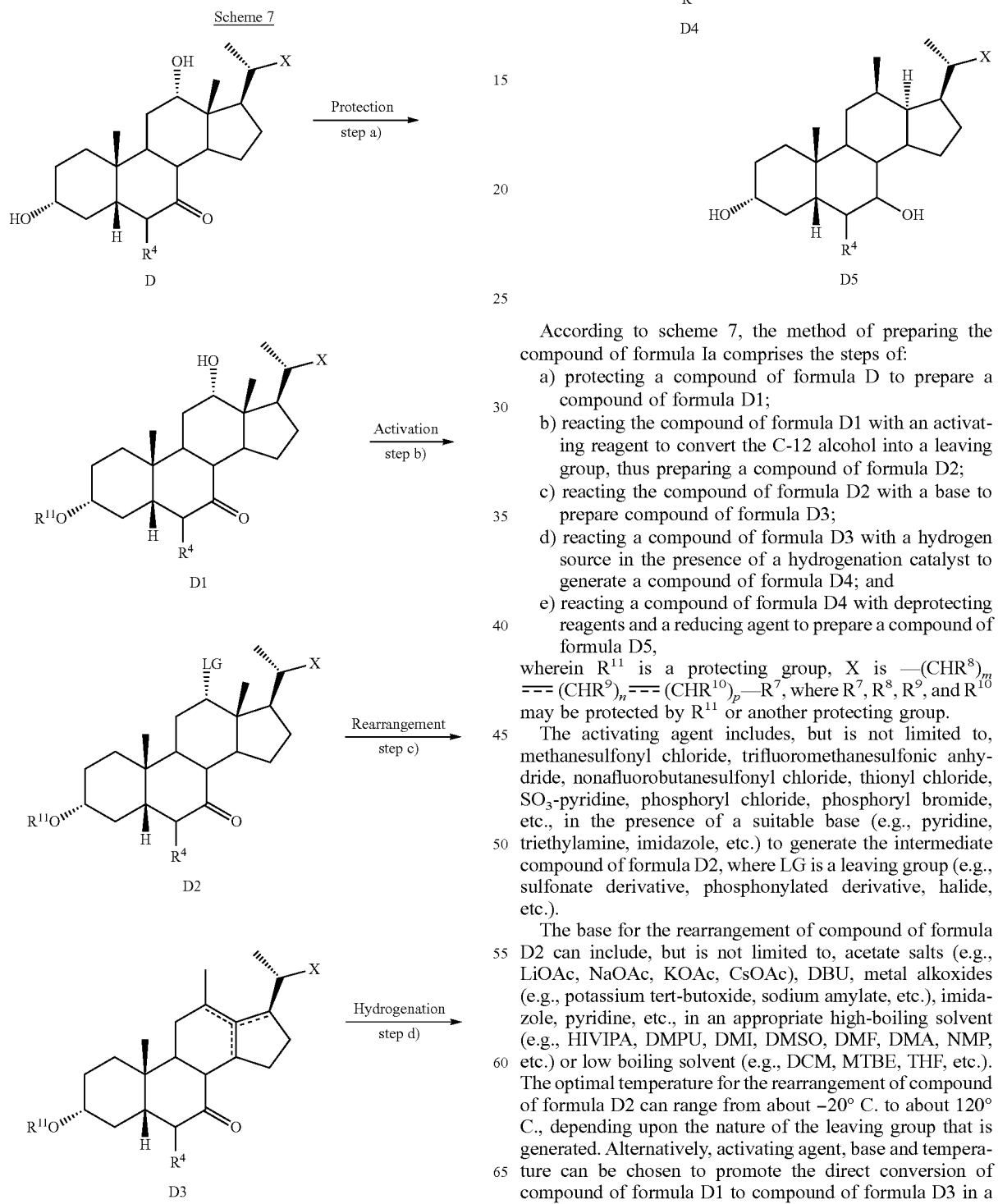

According to scheme 7, the method of preparing the compound of formula Ia comprises the steps of:
a) protecting a compound of formula D to prepare a compound of formula D1;
b) reacting the compound of formula D1 with an activating reagent to convert the C-12 alcohol into a leaving group, thus preparing a compound of formula D2;
c) reacting the compound of formula D2 with a base to prepare compound of formula D3;
d) reacting a compound of formula D3 with a hydrogen source in the presence of a hydrogenation catalyst to generate a compound of formula D4; and
e) reacting a compound of formula D4 with deprotecting reagents and a reducing agent to prepare a compound of formula D5,
wherein $R^{11}$ is a protecting group, X is $-(CHR^8)_m$ $=(CHR^9)_n$ $=(CHR^{10})_p-R^7$, where $R^7, R^8, R^9$, and $R^{10}$ may be protected by $R^{11}$ or another protecting group.

The activating agent includes, but is not limited to, methanesulfonyl chloride, trifluoromethanesulfonic anhydride, nonafluorobutanesulfonyl chloride, thionyl chloride, $SO_3$-pyridine, phosphoryl chloride, phosphoryl bromide, etc., in the presence of a suitable base (e.g., pyridine, triethylamine, imidazole, etc.) to generate the intermediate compound of formula D2, where LG is a leaving group (e.g., sulfonate derivative, phosphonylated derivative, halide, etc.).

The base for the rearrangement of compound of formula D2 can include, but is not limited to, acetate salts (e.g., LiOAc, NaOAc, KOAc, CsOAc), DBU, metal alkoxides (e.g., potassium tert-butoxide, sodium amylate, etc.), imidazole, pyridine, etc., in an appropriate high-boiling solvent (e.g., HMPA, DMPU, DMI, DMSO, DMF, DMA, NMP, etc.) or low boiling solvent (e.g., DCM, MTBE, THF, etc.). The optimal temperature for the rearrangement of compound of formula D2 can range from about −20° C. to about 120° C., depending upon the nature of the leaving group that is generated. Alternatively, activating agent, base and temperature can be chosen to promote the direct conversion of compound of formula D1 to compound of formula D3 in a single step without isolation of compound of formula D2.

The hydrogen source and catalyst for the hydrogenation of compound of formula D3 can include, but is not limited to the combinations of hydrogen, formic acid, ammonium formate, hydrazine, etc., in the presence of catalytic palladium, platinum, nickel, etc. on solid support (e.g., carbon, silica gel, alumina, SMOPEX® (mercaptoethylacrylate grafted polyolefin fiber), diatomaceous earth, etc.), optionally in a salt or organic solvate form.

Deprotection reagents can be chosen from standard reagents known by those skilled in the art, and are dependent on the chosen protecting groups. For example, for an acyl or carbonate protecting group at C-3 and ester protecting group of the sidechain acid, a metal hydroxide (e.g., LiOH, NaOH, KOH, CsOH, etc.) can be used to remove the C-3 acyl function while removing the sidechain ester functionality. In the subsequent step, the intermediate can be reduced with a reducing agent which may include, but is not limited to, sodium borohydride, sodium triacetoxyborohydride, sodium cyanoborohydride, etc., optionally in the presence of aqueous sodium hydroxide. Alternatively, the reduction step may be conducted prior to deprotection, and reducing agents may include, in addition to the aforementioned borohydride reagents, borane complexes and its mono- and disubstituted derivatives (e.g., BH$_3$THF, thexylborane, disiamylborane, catecholborane, etc.), followed by treatment with an appropriate deprotection reagent to generate compound of formula D5.

In one of the embodiments the compound of formula Ia is compound D3 or the deprotected analog thereof.

In one of the embodiment, the compound of formula Ia is compound 44.

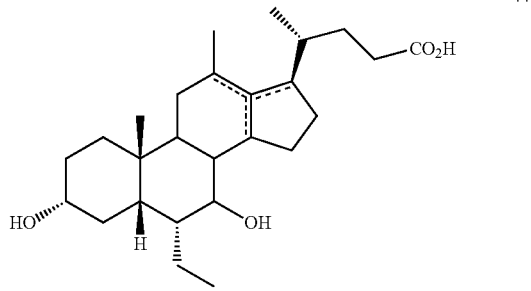

44 or a pharmaceutically acceptable salt, solvate, or amino acid, sulfate or glucuronide conjugate thereof.

In one of the embodiment, the compound of formula 44 is compound 44a.

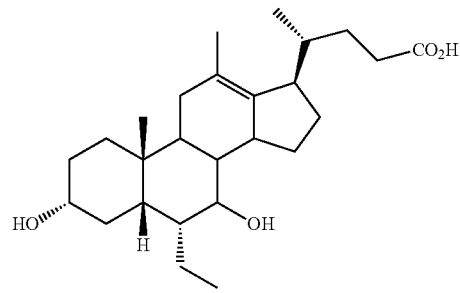

44a or a pharmaceutically acceptable salt, solvate, or amino acid, sulfate or glucuronide conjugate thereof.

In one embodiment, compound of formula Ia is compound D5 or a pharmaceutically acceptable salt, solvate, or amino acid, sulfate or glucuronide conjugate thereof.

In one of the embodiment, compound of formula Ib is compound 45.

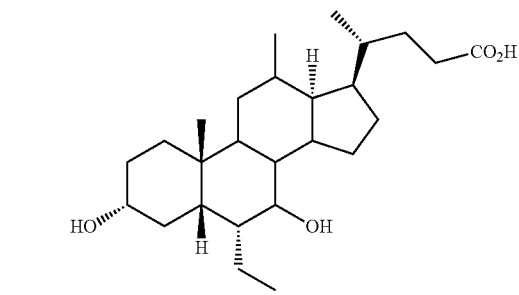

45 or a pharmaceutically acceptable salt, solvate, or amino acid, sulfate or glucuronide conjugate thereof.

In some of the aspects, the present disclosure relates to a method of preparing the compound of formula I, the method comprising the steps as shown in Scheme 8.

Scheme 8

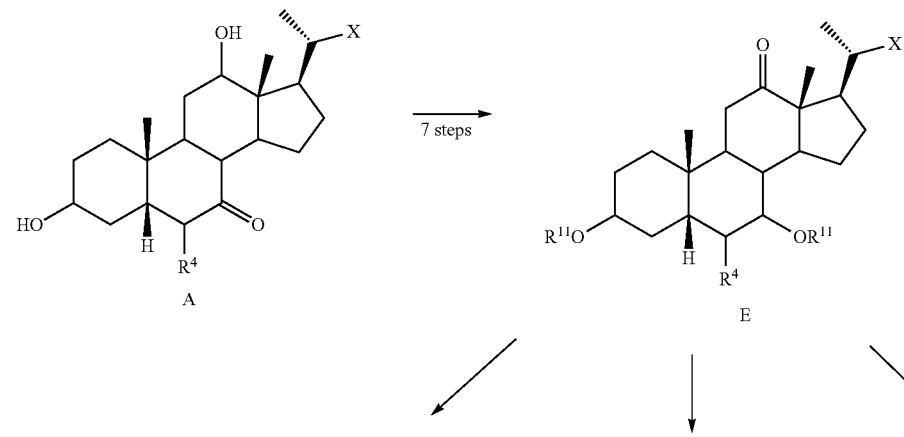

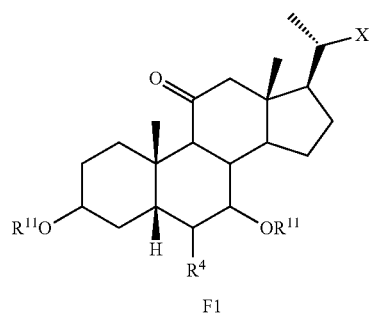

F1

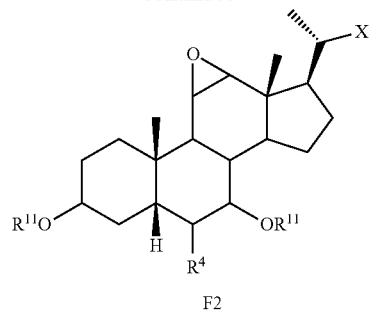

F2

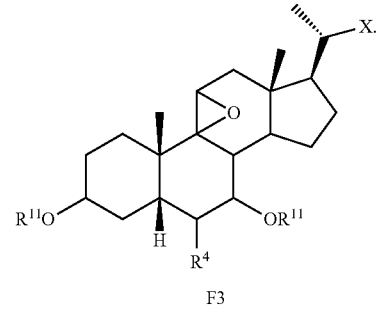

F3

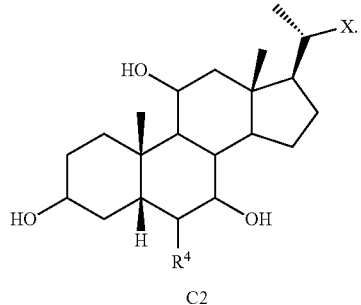

C2

In one of the embodiments the compound of formula E is prepared from the compound of formula A in 7 steps based on the procedure previously disclosed in Pellicciari et al., J. Med Chem. 59 (2016) 9201-9214.

In some of the embodiments, a compound of formula E undergoes 12-keto transposition to provide a compound of formula F1. In one of the embodiments a compound of formula F1 is prepared according to Scheme 9.

Scheme 9

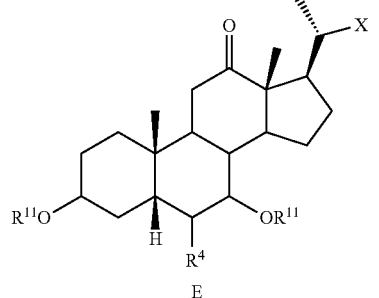

E

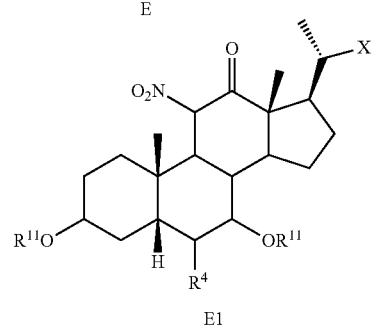

E1

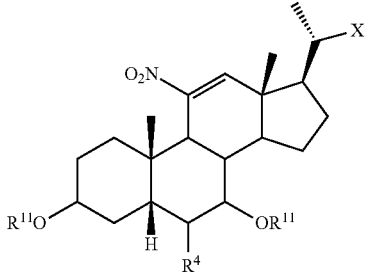

E2

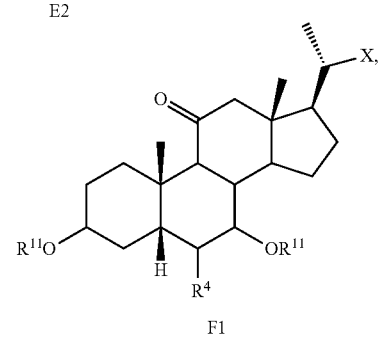

F1 wherein $R^4$, $R^{11}$, and X are as described herein.

According to Scheme 9, the process of preparing a compound of formula F1 comprises the step of:
a) reacting the compound of formula E with a nitrating reagent to prepare a compound of formula E1;
b) reducing compound of formula E1 in acidic media to provide a compound or formula E2;
c) converting compound of formula E2 into compound of formula F1 with oxidative and reductive methods.

In some of the aspects, a compound of formula E1 is prepared by reaction with nitrating agents (e.g. n-butyl nitrate, nitrocyclohexadienones, thionyl nitrate, etc.) in the presence of an acid (e.g. HNO$_3$, acetic acid, HF, etc.) or a base (e.g. t-butoxide, etc.). In some embodiments, the reaction is carried out at about 25° C., about 35° C., about 45° C., or about 55° C.

Some embodiments of the present disclosure relate to methods of converting a compound of formula E1 to E2 by using reducing agents (e.g., NaBH$_4$, NaCNBH$_3$, LiBH$_4$, i-Bu$_2$AlH, etc.) in basic or acidic media. In some embodiments, the reaction is carried out at about 0° C., about 25° C., about 35° C., about 45° C., or about 55° C. or up to reflux temperature of an appropriate solvent (e.g. methylene chloride, methanol, etc.).

In certain embodiments, a compound of formula E2 is converted into compound of formula F1 by Nef reaction using, reagents that include but are not limited to, oxone, TiCl$_3$, DBU, KMnO$_4$/KOH, and KH/Me$_3$SiCl. Alternatively, compound of formula E1 can be converted into nitroalkene of formula E2 by reduction with reducing agents (e.g. NaBH$_4$, NaCNBH$_3$, LiBH$_4$, etc.) in the presence of cerium trichloride (Stork G. et al. Tet. Lett. 25 (1984) 5367). Compound of formula F1 is converted into compound of formula C2 as shown in Scheme 8 and described herein (via deprotection and reduction, also shown in Schemes 1-6 and described herein).

In one of the embodiments a compound of formula F1 is prepared according to Scheme 10.

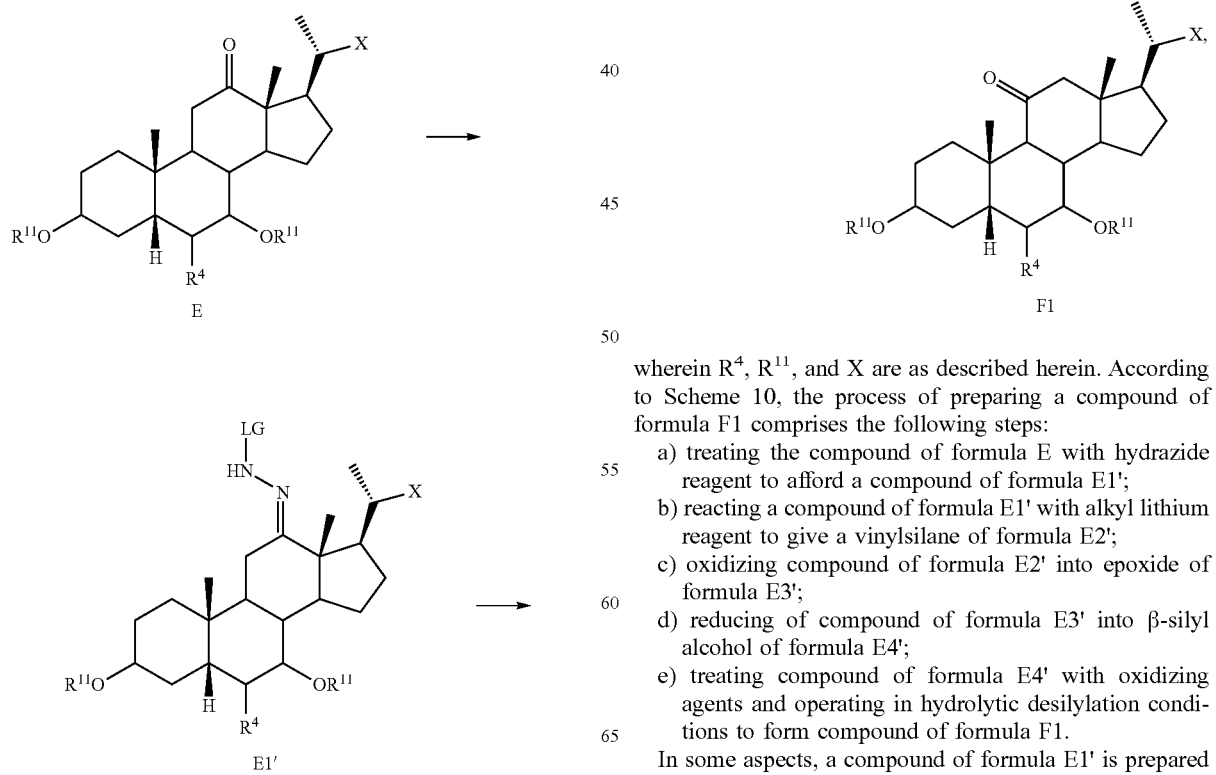

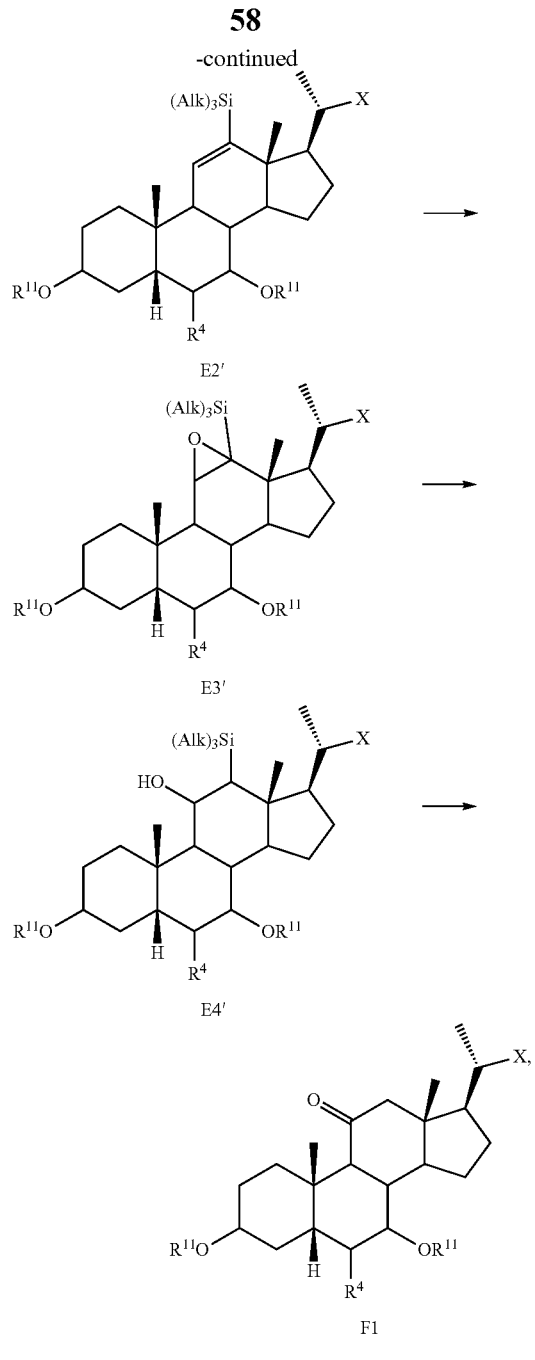

wherein $R^4$, $R^{11}$, and X are as described herein. According to Scheme 10, the process of preparing a compound of formula F1 comprises the following steps:
a) treating the compound of formula E with hydrazide reagent to afford a compound of formula E1';
b) reacting a compound of formula E1' with alkyl lithium reagent to give a vinylsilane of formula E2';
c) oxidizing compound of formula E2' into epoxide of formula E3';
d) reducing of compound of formula E3' into β-silyl alcohol of formula E4';
e) treating compound of formula E4' with oxidizing agents and operating in hydrolytic desilylation conditions to form compound of formula F1.

In some aspects, a compound of formula E1' is prepared from compound E by reaction with hydrazide reagents (e.g., benzenesulfonyl hydrazide, nicotinic hydrazide, propanoic acid hydrazide, p-toluensulfonyl hydrazide, formic hydrazide, 3-hydroxybenzoic hydrazide, p-toluic hydrazide m-anisic hydrazide, etc.) in acidic media (e.g., acetic acid, formic acid, etc.). In some embodiments, the reaction can be conducted in alcohols (e.g., methanol, ethanol, isopropanol, etc.) in the presence of catalytic amounts of acid (HCl, p-toluensulfonic acid, etc.) In some embodiments, the compound of formula E1' is obtained in about 60%, about 70%, about 75%, about 80%, about 85%, about 90%, about 95% or more than 95% yield. The compound of formula E1' can be purified (e.g., by chromatography or crystallization) or used for the next step without purification. In one of the embodiments, the compound of formula E' is crystallized and optionally recrystallized. In one of the embodiments, the compound of formula E' is used without purification.

Some embodiments disclosed in the present application relate to methods of converting a compound of formula E1' to E2' using alkyl lithium reagents (e.g. n-butyllithium, lithium diisopropyl amide, ethyllithium, t-butyllithium, etc.), a base (e.g. trimethylamine, tetramethylendiamine, pyridine, diethylamine, lutidine, etc.) and silylating agents (e.g. chlorotrimethylsilane, methyldichlorosilane, methyldiethoxysilane, methyldimethoxysilane, trichlorosilane, triethoxysilane, trimethoxysilane, etc.) in neat conditions or in an appropriate solvent (e.g. tetrahydrofuran, methyl tetrahydrofuran, diethyl ether) at low temperature (about $-78°$ C., about $-65°$ C., about $-55°$ C., about $-45°$ C., about $-35°$ C., about $-25°$ C., about $-15°$ C., or about $0°$ C.).

In certain embodiments, a compound of formula E2' is converted into a compound of formula E3' using oxidizing reagents including but not limited to m-chloroperbenzoic acid, peracetic acid, $H_2O_2$, oxone, tert-butylhydroperoxide, etc. in an appropriate solvent (e.g. dichloromethane, ethyl acetate, acetonitrile, acetone, water/acetonitrile, toluene, etc.).

In some embodiments, a compound E2' is reacted with reducing agents (e.g. $LiAlH_4$, $LiBH_4$, $NaBH_4$, $Na(BH_3CN)$, lithium aluminum hexahydride, etc.) to furnish compound of formula E4'.

In some embodiments, oxidation of the β-silyl alcohol of formula E4' with chromium reagents (e.g., sodium dichromate, potassium dichromate, chromium trioxide) in strongly acidic media with in situ generation of chromic acid generates compound of formula F1. Compound of formula F1 is converted into compound of formula C2 as shown in Scheme 8 and described herein (via deprotection and reduction, also shown in Schemes 1-6 and described herein).

In one of the embodiments a compound of formula F1 is prepared according to Scheme 11.

Scheme 11

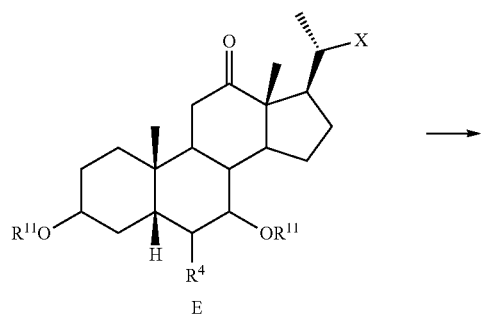

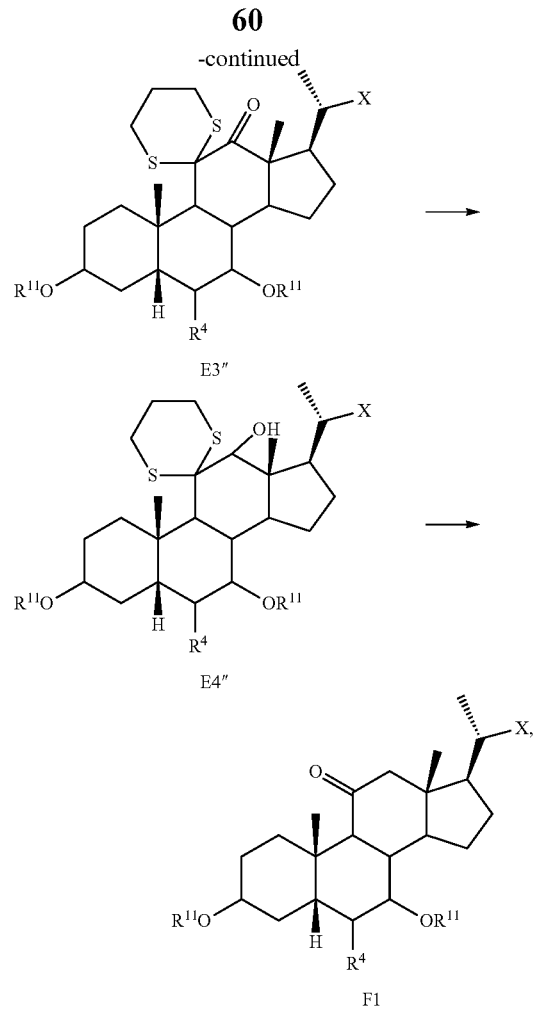

wherein $R^4$, $R^{11}$, and X are as described herein.

According to Scheme 11, the method for preparing a compound of formula F1 is based on the following steps:
 a) treating the compound of formula E with thiolation agents to form a compound of formula E3";
 b) reducing a compound of formula E3" to a compound of formula E4";
 c) converting E4" into the corresponding $C_{12}$ acetate and hydrolyzing to afford compound of formula F1; In certain embodiments, a compound of formula E3" is prepared from a compound of formula E by reaction with thiolation agents including, but not limited to, 1,3-propanedithiol di-p-toluene sulfonate in the presence of a base (e.g. potassium acetate, sodium acetate, sodium hydride, t-butoxide, etc.).

In another embodiment, a compound of formula E3" is reduced by means of reducing agents including, but not limited to, $LiAlH_4$, $NaBH_4$, $NaCNBH_3$, $LiBH_4$, $i$-$Bu_2AlH$, etc.) to afford a compound of formula E4". In some embodiments, the reaction is carried out at about $0°$ C., about $25°$ C., about $35°$ C., about $45°$ C., or about $55°$ C. or up to reflux temperature of an appropriate solvent (e.g. methylene chloride, methanol, etc.).

In some aspects, a compound of formula E4" is converted into a compound of formula F1 by means of hydrolysis with reducing agents (e.g., $Ca/NH_3$, $Li/NH_3$, $Na/NH_3$, Li/EDA, etc.). Compound of formula F1 is converted into compound of formula C2 as shown in Scheme 8 and described herein (via deprotection and reduction, also shown in Schemes 1-6 and described herein).

In some of the embodiments, a compound of formula E4'''' undergoes 11,12-epoxidation/opening transformation to provide a compound of formula H. In one of the embodiments a compound of formula H is prepared according to Scheme 12.

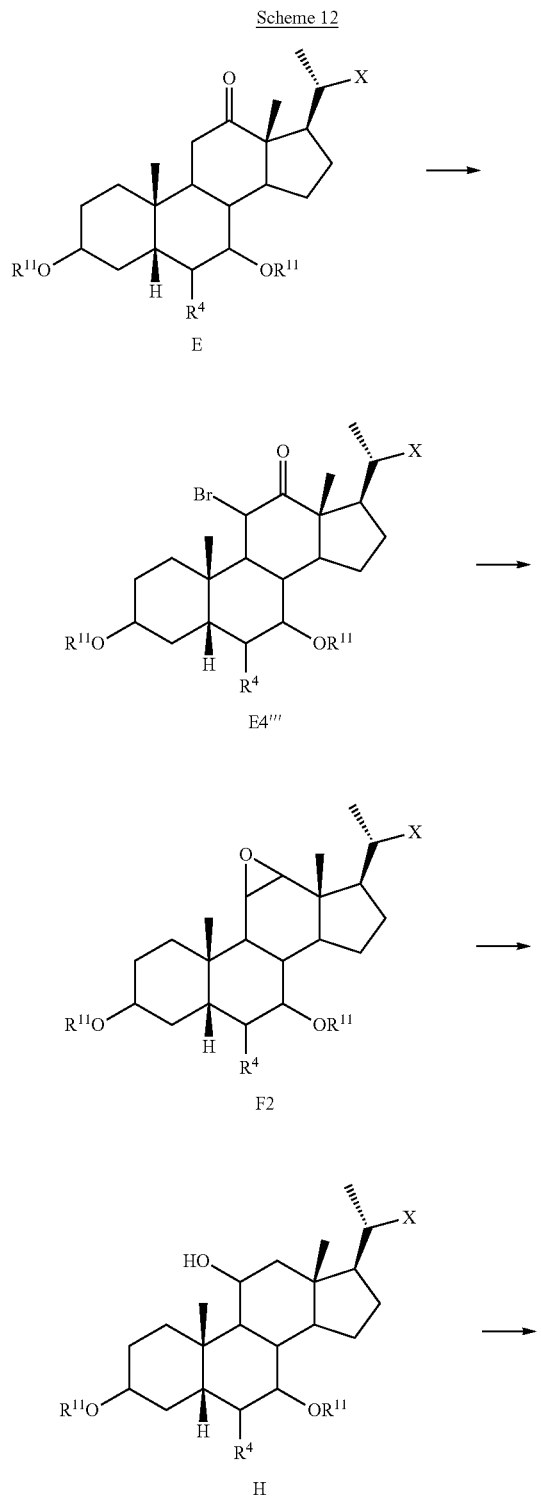

Scheme 12

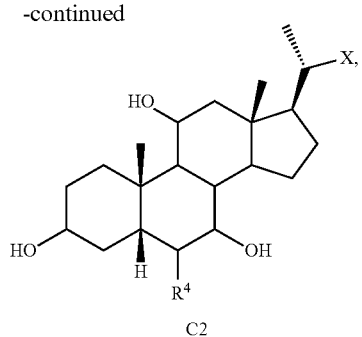

C2 wherein $R^4$, $R^{11}$, and X are as described herein.

According to Scheme 12, the process of preparing a compound of formula C2 comprises the following steps:
a) brominating the compound of formula E to prepare a compound of formula E4''';
b) reducing a compound of formula E4''' in basic media to provide a compound of formula F2;
c) reductive epoxide ring opening to form a compound of formula H;
d) deprotection to provide compound of formula C2.

In one of the embodiments the compound of formula F2 is prepared from the compound of formula E in 3 steps based on the procedure previously disclosed in Pellicciari et al., J. Med Chem. 59 (2016) 9201-9214. Alternatively, a compound of formula F2 is prepared using oxidizing reagents (m-chloroperbenzoic acid, peracetic acid, $H_2O_2$, oxone, tert-butylhydroperoxide, etc.) in an appropriate solvent (e.g. dichloromethane, ethyl acetate, acetonitrile, acetone, water/acetonitrile, toluene, etc.). Compound of formula H is converted into compound of formula C2 as shown and described herein).

In certain embodiments, a compound of formula H is prepared from a compound of formula F2 by hydrogenolysis in a suitable organic solvent (e.g., ethanol, acetic acid, tetrahydrofuran, pyridine, water, etc. or mixture thereof) with a catalyst or metal reagent (e.g., Raney®-Nickel, Raney Ni, Ra—Ni), or optionally in the presence of hydrogen and a catalyst (e.g., Pd, Pt, Rh, Ni, and salts thereof, etc.). In certain embodiments, metal reagent can be used alone in stoichiometric amounts, or in catalytic amounts in the presence of hydrogen. In other embodiments, the reaction can be conducted under catalytic transfer hydrogenation using hydrogen donors (1,3-cyclohexadiene, 1,7-octadiene, cyclohexene, ammonium formate, potassium formate, formic acid, ethanol, i-propanol, etc.). In one of the embodiments, hydrogenation and catalytic transfer hydrogenation is performed under continuous flow conditions.

In another embodiments, compound of formula F2 is reacted with dissolving metals (e.g. lithium, sodium, potassium, etc.) in an appropriate solvents (e.g. ethylenediamine, ammonia, ethanol, methanol, etc.) at room temperature, about 30° C., about 40° C., or about 50° C. or with metal hydrides (e.g. $NaBH_4$, $NaCNBH_3$, $LiBH_4$, NaH, tributyltin hydride, i-$Bu_2AlH$) coupled with Lewis acids (e.g. $AlBr_3$, $AlCl_3$, $BCl_3$, $BF_3$, $C_4H_8BF_3O_4$, $CH_4BF_3O$, $BF_3 \cdot C_2H_6O$, $C_4H_8BF_3O$, $SnCl_4$, $AlCl_{12}Ti_3$, $Cl_4Ti$, $Bi(OTf)_3$, $MgClO_4$, ZnI, etc.) in organic solvents (dichloromethane, tetrahydrofuran, diethyl ether, dimethoxyethane, dimethoxymethane, methanol, ethanol, water, etc. or mixtures).

In some of the embodiments, a compound of formula E undergoes 9,11-epoxidation/opening transformation to provide a compound of formula C2. In one of the embodiments a compound of formula C2 is prepared according to Scheme 13.

Scheme 13

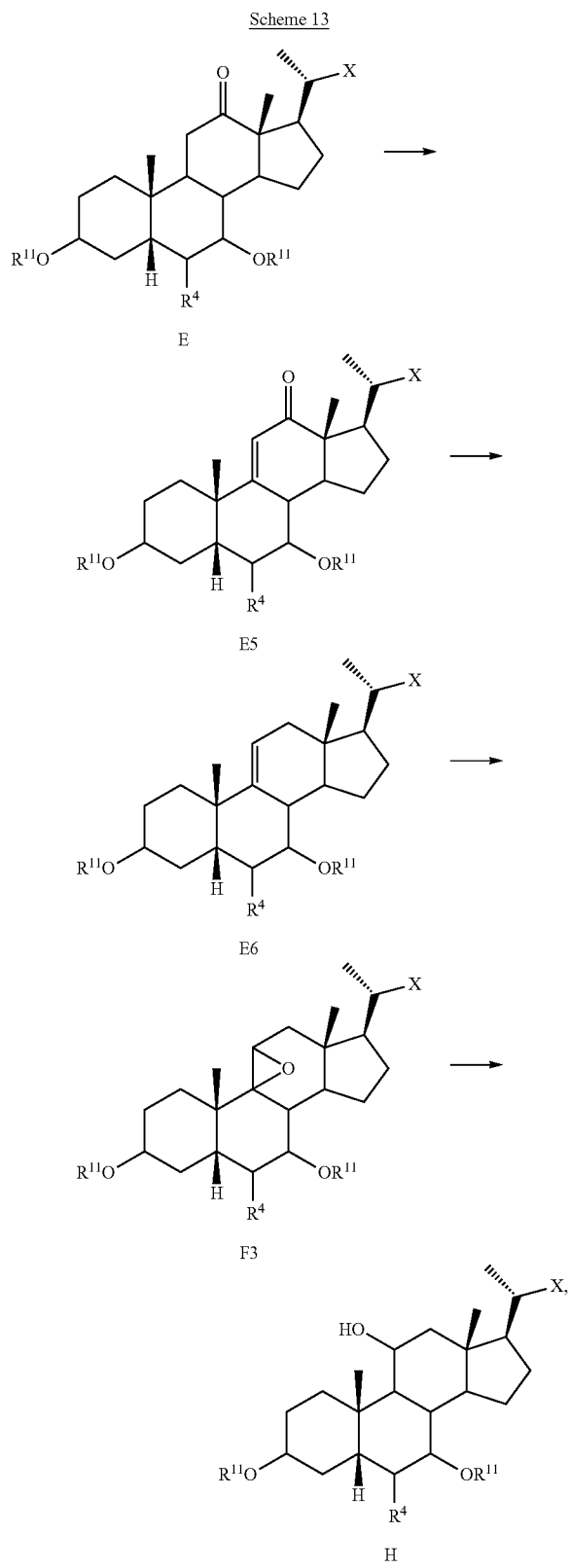

wherein $R^4$, $R^{11}$, and X are as described herein.

According to Scheme 13, the process of preparing a compound of formula C2 comprises the following steps:
  a) oxidizing the compound of formula E to prepare a compound of formula E5;
  b) reducing a compound of formula E5 to a compound of formula E6;
  c) epoxidizing a compound of formula E6 into a compound of formula F3;
  d) reducing of a compound of formula F3 to a compound of formula H;
  e) deprotecting a compound of formula H to prepare a compound of formula C2.

In one of the embodiments the compound of formula E5 is prepared from a compound of formula E based on the procedure previously disclosed by Fieser et al., J. Am. Chem. Soc. 73 (1951) 4133.

In certain embodiments, a compound of formula E5 is reacted with reducing reagents (e.g. $NaBH_4$, $NaCNBH_3$, $LiBH_4$, NaH, tributyltin hydride, i-$Bu_2AlH$, t-butylaminoborane, triethylsilane) coupled with Lewis acids ($AlBr_3$, $AlCl_3$, $Bi(OTf)_3$, $MgClO_4$, ZnI, $BCl_3$, $BF_3$, $C_4H_8BF_3O_4$, $CH_4BF_3O$, $BF_3 \cdot C_2H_6O$, $C_4H_8BF_3O$, $SnCl_4$, $AlCl_{12}Ti_3$, $TiCl_4$) in organic solvents (dichloromethane, tetrahydrofuran, diethyl ether, dimethoxyethane, dimethoxymethane, methanol, ethanol, water, etc. or mixtures). In some embodiments, the compound of formula E6 is obtained in about 70%, about 75%, about 80%, about 85%, about 90%, about 95% or more than 95% yield. The compound of formula E6 can be purified (e.g., by chromatography or crystallization) or used for the next step without purification.

In some embodiments, the compound of formula E6 is synthesized according to the procedure previously disclosed in Hicks et al., J. Biol. Chem. (1945) 633-640.

In other embodiments, the reaction of compound of formula E6 is oxidized by means of peroxides (e.g. m-chloroperbenzoic acid, peracetic acid, $H_2O_2$, oxone, t-butylhydroperoxide, t-butylperoxybenozate, manganese dioxide, etc.) in an appropriate solvent (e.g. dichloromethane, ethyl acetate, acetonitrile, acetone, water/acetonitrile, toluene, etc.).

In one of the embodiments, epoxide of formula F3 is submitted to hydrogenolysis in a suitable organic solvent (e.g., ethanol, acetic acid, tetrahydrofuran, pyridine, water etc. or mixture thereof) with a catalyst or metal reagent (e.g., Raney®-Nickel, Raney Ni, Ra—Ni), or optionally in the presence of hydrogen and a catalyst (e.g., Pd, Pt, Rh, Ni, and salts thereof, etc.). In certain embodiments, metal reagents can be used alone in stoichiometric amounts, or in catalytic amounts in the presence of hydrogen. In other embodiments, the reaction can be conducted under catalytic transfer hydrogenation using hydrogen donors (e.g. 1,3-cyclohexadiene, 1,7-octadiene, cyclohexene, ammonium formate, potassium formate, formic acid, ethanol, i-propanol, etc.). In one of the embodiments, hydrogenation and catalytic transfer hydrogenation is performed under continuous flow conditions.

In another embodiments, compound of formula F3 is reacted with dissolving metals (lithium, sodium, potassium, etc.) in an appropriate solvents (ethylenediamine, ammonia, ethanol, methanol, etc.) at room temperature, about 30° C., about 40° C., or about 50° C. or with metal hydrides (e.g. $NaBH_4$, $NaCNBH_3$, $LiBH_4$, NaH, tributyltin hydride (i-$Bu_2AlH$)_2) coupled with Lewis acids (e.g. $AlBr_3$, $AlCl_3$, $BCl_3$, $BF_3$, $C_4H_8BF_3O_4$, $CH_4BF_3O$, $BF_3 \cdot C_2H_6O$, $C_4H_8BF_3O$, $SnCl_4$, $AlCl_{12}Ti_3$, $TiCl_4$, $Bi(OTf)_3$, $MgClO_4$, ZnI, etc.) in organic solvents (dichloromethane, tetrahydrofuran, diethyl ether, dimethoxyethane, dimethoxymethane, methanol, ethanol, water, etc. or mixtures).

In some of the aspects, the present disclosure relates to a method of preparing the compound of formula F1 as shown in Scheme 14.

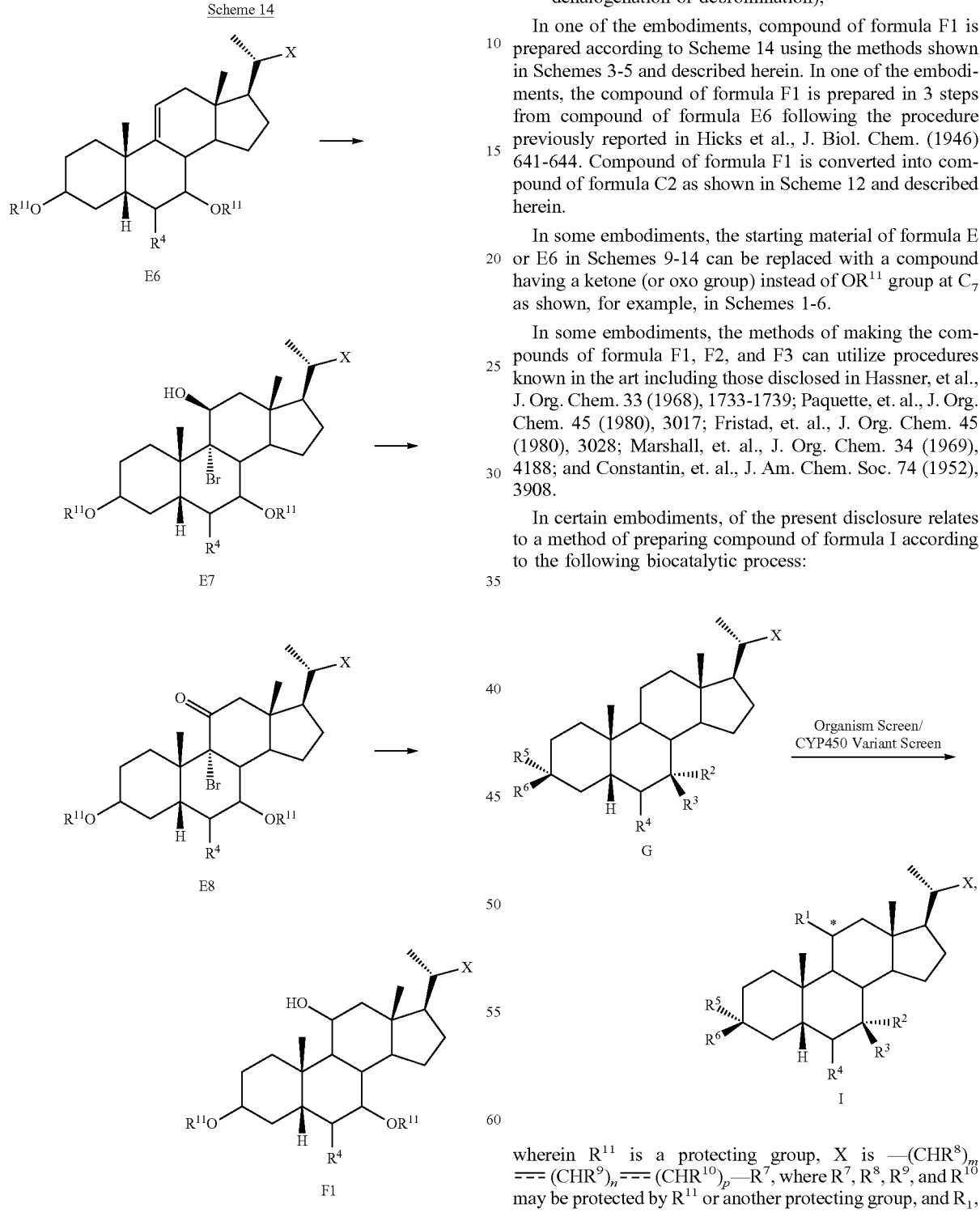

According to Scheme 14, the synthesis compound of formula F1 comprises the steps of a) reacting a compound of formula E6 with a brominating reagent to provide a compound of formula E7;

b) reacting the compound of formula E7 with an oxidizing agent to prepare a compound of formula E8;

c) reacting the compound of formula E8 with a reducing agent to prepare a compound of formula F1 (reductive dehalogenation or debromination);

In one of the embodiments, compound of formula F1 is prepared according to Scheme 14 using the methods shown in Schemes 3-5 and described herein. In one of the embodiments, the compound of formula F1 is prepared in 3 steps from compound of formula E6 following the procedure previously reported in Hicks et al., J. Biol. Chem. (1946) 641-644. Compound of formula F1 is converted into compound of formula C2 as shown in Scheme 12 and described herein.

In some embodiments, the starting material of formula E or E6 in Schemes 9-14 can be replaced with a compound having a ketone (or oxo group) instead of $OR^{11}$ group at $C_7$ as shown, for example, in Schemes 1-6.

In some embodiments, the methods of making the compounds of formula F1, F2, and F3 can utilize procedures known in the art including those disclosed in Hassner, et al., J. Org. Chem. 33 (1968), 1733-1739; Paquette, et. al., J. Org. Chem. 45 (1980), 3017; Fristad, et. al., J. Org. Chem. 45 (1980), 3028; Marshall, et. al., J. Org. Chem. 34 (1969), 4188; and Constantin, et. al., J. Am. Chem. Soc. 74 (1952), 3908.

In certain embodiments, of the present disclosure relates to a method of preparing compound of formula I according to the following biocatalytic process:

wherein $R^{11}$ is a protecting group, X is $-(CHR^8)_m$ $===(CHR^9)_n===(CHR^{10})_p-R^7$, where $R^7$, $R^8$, $R^9$, and $R^{10}$ may be protected by $R^{11}$ or another protecting group, and $R_1$, $R_2$, $R_3$, $R_4$, $R_5$, $R_6$ are as described herein.

In one of the embodiments, the biocatalytic method provides compound 100 (from obeticholic acid (OCA)):

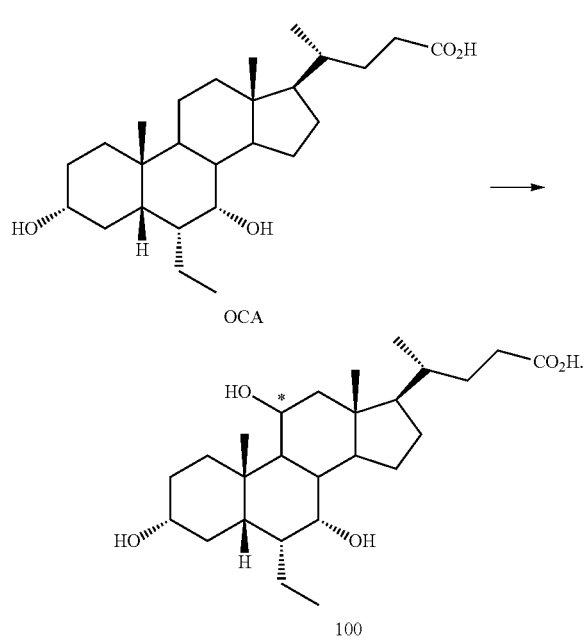

OCA

100

A wide variety of microbial organisms are capable of catabolizing xenobiotics. Organisms which are capable of biooxidation can be drawn from both mesophiles or extremeophiles, including but not limited to either wild type or genetically modified prokaryotes and eukaryotes. In some cases, the organisms are classified in the same genus but differ in type strain based on isolation source or growth conditions. Examples of microbial organisms include but are not limited to the following: bacteria, yeast, fungi, algea, and molds. Fermentation can take place during any phase of the microbial lifecycle including the lag phase, exponential phase, or stationary phase, using either aerobic and anaerobic conditions. The suitable organisms include, but are not limited to *Streptomyces diastatochromogenes, Streptomyces griseus, Streptomyces sp, Streptomyces rimosus, Streptomyces albidoflavus, Streptomyces avermitilis, Streptomyces fradiae, Streptomyces griseolus, Streptomyces platensis, Streptomyces violascens, Streptomyces ochraceiscleroticus, Methylobacterium extorquens, Methylophaga thalassica, Rhizopus stolonifer, Absidia coerulea, Beauveria bassiana, Cunninghamella elegans, Rhizopus oryzae, Gliocladium roseum, Verticillium lecanii, Fusarium oxysporum, Curvularia lunata, Mortierella isabellina, Cunninghamella blakesleeana, Mortierella ramanniana, Mucor rouxii, Rhodococcus sp., Streptomyces griseus, Gluconobacter oxydans, Sporobolomyces salmonicolor, Saccharyomyces cerevisiae, Candida parapsilosis, Rhodococcus erythropolis, Rhodotorula glutinis, Kluyveromyces lactis, Debrayomyces hansenii, Pichia angusta, Kluyveromyces polysporus, Pichia guiliermondii, Saccharyomyces cerevisie S288c, Lactobacillus brevis, Ruegeria pomeroyi (Silicibacter pomeroyi), Leucanostoc mesenteroides, Burkholderia thailandensis, Bradyrhizobium sp., Rhodopseudomonas palustris, Nakamurella multipartite, Sphingomonas wittichii, Rhodopiruellula baltica, Rhodococcus opacus, Helicostylum piriforme, Agrobacterium sp., Streptomyces lincolnensis, Bacillus megaterium, Pseudomonas sp., Penicillium chrysogenum, Nonomuraea recticatena, Verticillium theobromas, Cunninghamella echinulate, Syncephalastrum racemosum, Absidia pseudocylindrospora, Petromyces alliaceus, Aspergillus ochraceus, Aspergillus oryzae, Mucor plumbeus, Cyathus striatus, Absidia corymbifera, Gliocladium viride, Geotrichum candidum, Kluyveromyces marxianus, Cladophialophora psammophila, Cladophialophora immunda, Pseudeurotium zonatum, Cunninghamella echinulate, Cladosporium sphaerospermum, Streptomyces* sp., *Azoarcus toluvorans, Pseudomonas chlororaphis, Phanerochaete chrysosporium, Pseudomonas putida* mt-2, *Cupriavidus necator, Cupriavidus basilensis, Novosphingobium subterraneum, Novosphingobium aromaticivorans, Rhodococcus rhodochrous, Novosphingobium stygium, Burkholderia* sp., *Pseudoxanthomonas spadix, Mycobacterium gilvum, Delftia acidovorans, Paracoccus denitrificans, Mycobacterium neoaurum, Streptomyces rimosus, Streptomyces ambofaciens, Pleurotis sapidus, Emericella nidulans, Fusarium solani, Comamonas testeroni, Fusarium graminearum, Fusarium longipes, Fusarium cerealis, Fusarium sporotrichiodes, Fusarium equiseti, Fusarium cerealis, Fusarium incarnatum, Nonomuraca dietziae, Methyloccus capsulatus, Rhizopus stolonifera, Mucor flavus, Streptomyces lilacinus, Xanthobacter* sp., *Rhizopus* microspores, *Sporidiobolus johnsonii, Bradyrhizobium japonicum, Ogataea methanolica, Bacillus benzeovorans, Cupriavidus necator, Mycobacterium parafortuitum, Actinoplanes* sp., *Paracoccus pantotrophus, Streptomyces rochii, Mycoplasma hpofaciens, Aspergillus niger* 402, *Agrocybe aegerita, Agrocybe aegerita, Caldariomyces fumago, Mycobacterium* sp., *Rhodococcus* sp., *Rhodococcus rhodochrous, Rhizopus oryzae, Phanerochaete chrysosporium, Fusarium ciliatum, Escherichia coli, Mucor griseocyanus, Rhodopirellula baltica.*

In one of the embodiments, the microorganisms are grown in about 50 ml conical centrifuge tubes containing about 10 ml of the required growth medium. In some embodiments, the growth media can be Nutrient Broth (e.g., 15 g Peptone, 3 g Yeast extract, 6 g NaCl, 1 g Glucose); Gym *Streptomyces* media (e.g., 4 g Glucose, 4 g Yeast extract, 10 g Malt extract); Malt extract peptone (e.g., 30 g Malt extract, 3 g Peptone); or Potato dextrose media (e.g., 30 g Potato extract, 10 g Glucose). Following inoculation of media from microbial glycerol stocks, the cultures are incubated for 7 days at about 28° C. with shaking. After that, about 1 ml of each microbial culture was transferred into the wells of deep 96 well plates. The plates are incubated at about 28° C. with agitation for 48 hours before addition of OCA dissolved in DMSO (to the final concentration of about 2 mg/ml). The plates are incubated for a further 36 hours before addition of about 1 ml of 100% acetonitrile, after which the plates are incubated at room temperature before centrifugation at 9,000×g for 15 mins. About 200 μL of supernatant are transferred to a clean 96 well plate before analysis by UHPLC (ultra-high performance liquid chromatography). In one of the embodiments, the biotransformation process can utilize the method(s) reported in Ishida, et al., Chem. Pharm. Bull. 46 (1998), 12-16 for natural product 3α, 7α, 11α-trihydroxy-5β-cholan-24-oic acid (11α-OH CDCA).

In one of the embodiments, the present disclosure provides compounds of formula I I, Ia, Ib, I-9, II, III, IIIa, IIIb, C2, or D5, wherein $R^4$ is in the α-position. In one embodiment, the present disclosure provides compounds of formula I, Ia, Ib, I-9, II, III, IIIa, IIIb, C2, or D5, wherein $R^4$ is $C_1$-$C_4$ alkyl. In one of the embodiments, the present disclosure provides compounds of formula I, Ia, Ib, I-9, II, III, IIIa, IIIb, C2, or D5, wherein $R^4$ is methyl, ethyl, or propyl. In one embodiment, $R^4$ is ethyl. In another embodiment, $R^4$ is alpha-ethyl. In one of the embodiments, the present disclosure provides compounds of formula I, Ia, Ib, I-9, II, III, IIIa, IIIb, C2, or D5, wherein $R^4$ is H or halogen. In one of the embodiments, the present disclosure provides compounds of formula I, Ia, Ib, I-9, II, III, IIIa, IIIb, C2, or D5, wherein $R^4$ is $C_1$-$C_6$ alkyl optionally substituted with one or more halogen or OH. In one of the embodiments, the present disclosure provides compounds of formula I, Ia, Ib, I-9, II, III, IIIa, IIIb, C2, or D5, wherein $R^4$ is $C_2$-$C_6$ alkenyl or $C_2$-$C_6$ alkynyl.

In one of the embodiments, the present disclosure provides compounds of formula I, Ia, Ib, I-9, II, III, IIIa, IIIb, C2, or D5, wherein $R^7$ is OH, $OSO_3H$, $SO_3H$, $OSO_2NH_2$, $SO_2NH_2$, $OPO_3H_2$, $PO_3H_2$, $CO_2H$, or C(O)NHOH.

In one of the embodiments, the present disclosure provides compounds of formula I, Ia, Ib, I-9, II, III, IIIa, IIIb, C2, or D5, wherein $R^7$ is OH, $OSO_3H$, $OSO_2NH_2$, $OPO_3H_2$, or $CO_2H$.

In one of the embodiments, the present disclosure provides compounds of formula I, Ia, Ib, I-9, II, III, IIIa, IIIb, C2, or D5, wherein $R^7$ is OH.

In one of the embodiments, the present disclosure provides compounds of formula I, Ia, Ib, I-9, II, III, IIIa, IIIb, C2, or D5, wherein $R^7$ is $CO_2H$.

In one of the embodiments, the present disclosure provides compounds of formula I, Ia, Ib, I-9, II, III, IIIa, IIIb, C2, or D5, wherein $R^7$ is $OSO_3H$.

In one of the embodiments, the present disclosure provides compounds of formula I, Ia, Ib, I-9, II, III, IIIa, IIIb, C2, or D5, wherein $R^7$ is $SO_3H$.

In one of the embodiments, the present disclosure provides compounds of formula I, Ia, Ib, I-9, II, III, IIIa, IIIb, C2, or D5, wherein $R^7$ is $OSO_2NH_2$ or $SO_2NH_2$.

In one of the embodiments, the present disclosure provides compounds of formula I, Ia, Ib, I-9, II, III, IIIa, IIIb, C2, or D5, wherein $R^7$ is $OPO_3H_2$, $PO_3H_2$, or C(O)NHOH.

In one of the embodiments, the present disclosure provides compounds of formula I, Ia, Ib, I-9, II, III, IIIa, IIIb, C2, or D5, wherein $R^7$ is tetrazolyl, oxadiazolyl, thiadiazolyl, 5-oxo-1,2,4-oxadiazolyl, 5-oxo-1,2,4-thiadiazolyl, oxazolidine-dionyl, thiazolidine-dionyl, 3-hydroxyisoxazolyl, 3-hydroxyisothiazolyl, or 2,4-difluoro-3-hydroxyphenyl.

In one of the embodiments, the present disclosure provides compounds of formula I, Ia, Ib, I-9, II, III, IIIa, IIIb, C2, or D5, wherein $R^7$ is OH, $OSO_3H$, $OSO_2NH_2$, $OPO_3H_2$, $CO_2H$, tetrazolyl, oxadiazolyl, thiadiazolyl, 5-oxo-1,2,4-oxadiazolyl, 5-oxo-1,2,4-thiadiazolyl, oxazolidine-dionyl, thiazolidine-dionyl, 3-hydroxyisoxazolyl, 3-hydroxyisothiazolyl, or 2,4-difluoro-3-hydroxyphenyl.

In one of the embodiments, the present disclosure provides compounds of formula I, wherein $R^5$ is $OSO_3H$, $OCOCH_3$, or $OPO_3H_2$.

In one of the embodiments, the present disclosure provides compounds of formula I, wherein $R^5$ and $R^6$ taken together with the carbon atom to which they are attached form a carbonyl.

In one of the embodiments, the present disclosure provides compounds of formula I, Ia, Ib, I-9, II, III, C2, or D5, wherein m is 0.

In one of the embodiments, the present disclosure provides compounds of formula I, Ia, Ib, I-9, II, III, C2, or D5, wherein m is 1.

In one of the embodiments, the present disclosure provides compounds of formula I, Ia, Ib, I-9, II, III, C2, or D5, wherein m is 2.

In one of the embodiments, the present disclosure provides compounds of formula I, Ia, Ib, I-9, II, III, C2, or D5, wherein n is 1.

In one of the embodiments, the present disclosure provides compounds of I, Ia, Ib, I-9, II, III, C2, or D5, wherein p is 0.

In one of the embodiments, the present disclosure provides compounds of formula I, Ia, Ib, I-9, II, III, C2, or D5, wherein $R^1$ is in the β-position (beta-position).

In one embodiment, the compound prepared by the methods of the present disclosure is compound 100:

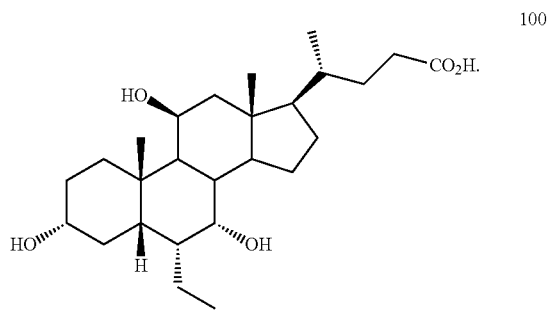 [SMILES: CC[C@H]1[C@@H](O)C2C3CC[C@H]([C@H](C)CCC(=O)O)[C@@]3(C)C[C@H](O)C2[C@@]2(C)CC[C@@H](O)C[C@@H]12]

In one aspect, the method of the present application produces a substantially pure compound of formula I, or a pharmaceutically acceptable salt thereof. The term "purity" as used herein refers to the amount of compound of formula I based on analytic methods commonly used in the art (e.g., HPLC). In some embodiments, the compound of formula I has a purity of greater than about 90%. In one embodiment, the compound of formula I has a purity of greater than about 95%. In one embodiment, the compound of formula I has a purity of greater than about 98%. For example, the purity of the synthesized compound of Formula I is about 96.0%, about 97.0%, about 98.0%, about 99.0%, or about 100%. For example, the purity of the synthesized compound of formula I is 98.5%, 99.0%, or 99.5%. In one embodiment, the purity is determined by HPLC.

The present application provides methods for the synthesis of highly pure compounds of formula I which are safe and which can produce compounds of formula I on a large scale. In one embodiment, the method of the present application produces compounds of formula I in high yield (>98%) and with limited number of impurities.

The compounds of the disclosure have asymmetric centers and can be isolated in optically active or racemic forms. It is well known in the art how to prepare optically active forms, such as by resolution of racemic forms or by synthesis from optically active starting materials. Many geometric isomers of olefins, and the like can also be present in the compounds described herein, and all such stable isomers are contemplated in the present disclosure. Cis and trans geometric isomers of the compounds of the disclosure and can be isolated as a mixture of isomers or as separate isomeric forms. All chiral, diastereomeric, racemic, and geometric isomeric forms of a structure are intended, unless specific stereochemistry or isomeric form is specifically indicated. All processes used to prepare compounds of the present disclosure and intermediates made therein are considered to be part of the present disclosure. All tautomers of shown or described compounds are also considered to be part of the present disclosure. Furthermore, the disclosure also includes metabolites of the compounds described herein.

The disclosure also comprehends isotopically-labeled compounds of the disclosure, or pharmaceutically acceptable salts, solvates, or amino acid conjugates thereof, which are identical to those recited in formulae of the application and following, but for the fact that one or more atoms are replaced by an atom having an atomic mass or mass number different from the atomic mass or mass number most commonly found in nature. Examples of isotopes that can be incorporated into compounds of the disclosure, or pharmaceutically acceptable salts, solvates, or amino acid conjugates thereof include isotopes of hydrogen, carbon, nitrogen, fluorine, such as $^2H$, $^3H$, $^{11}C$, $^{13}C$, $^{14}C$, and $^{18}F$.

Deuterated, i.e., $^2H$, tritiated, i.e., $^3H$, and carbon-14, i.e., $^{14}C$, isotopes may be used for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be used in some circumstances. Isotopically labeled compounds of the disclosure, or pharmaceutically acceptable salts, solvates, or amino acid conjugates thereof can generally be prepared by carrying out the procedures disclosed in the Schemes and/or in the Examples, by substituting a readily available isotopically labeled reagent for a non-isotopically labeled reagent. However, one skilled in the art will recognize that not all isotopes can be included by substitution of the non-isotopically labeled reagent. In one embodiment, compounds of the disclosure, or pharmaceutically acceptable salts, solvates, or amino acid conjugates thereof are not isotopically labeled. In one embodiment, deuterated compounds of the disclosure are useful for bioanalytical assays. In another embodiment, compounds of the disclosure, or pharmaceutically acceptable salts, solvates, or amino acid conjugates thereof are radiolabeled.

Pharmaceutical Compositions

A "pharmaceutical composition" is a formulation containing one or more compounds of the disclosure in a form suitable for administration to a subject. In one embodiment, the pharmaceutical composition is in bulk or in unit dosage form. It can be advantageous to formulate compositions in dosage unit form for ease of administration and uniformity of dosage. Dosage unit form as used herein refers to physically discrete units suited as unitary dosages for the subject to be treated; each unit containing a predetermined quantity of active reagent calculated to produce the desired therapeutic effect in association with the required pharmaceutical carrier. The specification for the dosage unit forms are dictated by and directly dependent on the unique characteristics of the active reagent and the particular therapeutic effect to be achieved, and the limitations inherent in the art of compounding such an active agent for the treatment of individuals.

Possible formulations include those suitable for oral, sublingual, buccal, parenteral (e.g., subcutaneous, intramuscular, or intravenous), rectal, topical including transdermal, intranasal and inhalation administration. Most suitable means of administration for a particular patient will depend on the nature and severity of the disease being treated or the nature of the therapy being used and on the nature of the active compound, but where possible, oral administration may be used for the prevention and treatment of FXR mediated diseases and conditions. Formulations suitable for oral administration may be provided as discrete units, such as tablets, capsules, cachets, lozenges, each containing a predetermined amount of the active compound; as powders or granules; as solutions or suspensions in aqueous or non-aqueous liquids; or as oil-in-water or water-in-oil emulsions. Formulations suitable for sublingual or buccal administration include lozenges comprising the active compound and, typically a flavored base, such as sugar and acacia or tragacanth and pastilles comprising the active compound in an inert base, such as gelatin and glycerin or sucrose acacia.

Formulations suitable for parenteral administration typically comprise sterile aqueous solutions containing a predetermined concentration of the active compound; the solution may be isotonic with the blood of the intended recipient. Additional formulations suitable for parenteral administration include formulations containing physiologically suitable co-solvents and/or complexing agents such as surfactants and cyclodextrins. Oil-in-water emulsions are also suitable formulations for parenteral formulations. Although such solutions may be administered intravenously, they may also be administered by subcutaneous or intramuscular injection.

Formulations suitable for rectal administration may be provided as unit-dose suppositories comprising the active ingredient in one or more solid carriers forming the suppository base, for example, cocoa butter.

Formulations suitable for topical or intranasal application include ointments, creams, lotions, pastes, gels, sprays, aerosols, and oils. Suitable carriers for such formulations include petroleum jelly, lanolin, polyethylene glycols, alcohols, and combinations thereof.

Formulations of the disclosure may be prepared by any suitable method, typically by uniformly and intimately admixing the active compound with liquids or finely divided solid carriers or both, in the required proportions and then, if necessary, shaping the resulting mixture into the desired shape.

For example, a tablet may be prepared by compressing an intimate mixture comprising a powder or granules of the active ingredient and one or more optional ingredients, such as a binder, lubricant, inert diluent, or surface-active dispersing agent, or by molding an intimate mixture of powdered active ingredient and inert liquid diluent. Suitable formulations for administration by inhalation include fine particle dusts or mists which may be generated by means of various types of metered dose pressurized aerosols, nebulizers, or insufflators.

For pulmonary administration via the mouth, the particle size of the powder or droplets is typically in the range of 0.5-10 µm, or may be about 1-5 µm, to ensure delivery into the bronchial tree. For nasal administration, a particle size in the range of 10-500 µm may be used to ensure retention in the nasal cavity.

Metered dose inhalers are pressurized aerosol dispensers, typically containing a suspension or solution formulation of the active ingredient in a liquefied propellant. During use, these devices discharge the formulation through a valve adapted to deliver a metered volume, typically from 10 to 150 µm, to produce a fine particle spray containing the active ingredient. Suitable propellants include certain chlorofluorocarbon compounds, for example, dichlorodifluoromethane, trichlorofluoromethane, dichlorotetrafluoroethane, and mixtures thereof. The formulation may additionally contain one or more co-solvents, for example, ethanol surfactants, such as oleic acid or sorbitan trioleate, anti-oxidants, and suitable flavoring agents.

Nebulizers are commercially available devices that transform solutions or suspensions of the active ingredient into a therapeutic aerosol mist either by means of acceleration of a compressed gas typically air or oxygen, through a narrow venturi orifice, or by means of ultrasonic agitation. Suitable formulations for use in nebulizers consist of the active ingredient in a liquid carrier and comprise up to 40% w/w of the formulation, preferably less than 20% w/w. The carrier is typically water or a dilute aqueous alcoholic solution, preferably made isotonic with body fluids by the addition of, for example, sodium chloride. Optional additives include preservatives if the formulation is not prepared sterile, for example, methyl hydroxy-benzoate, anti-oxidants, flavoring agents, volatile oils, buffering agents, and surfactants.

Suitable formulations for administration by insufflation include finely comminuted powders which may be delivered by means of an insufflator or taken into the nasal cavity in the manner of a snuff. In the insufflator, the powder is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100% w/w of the formulation.

In a further embodiment, the present disclosure provides a pharmaceutical composition comprising, as active ingredient, a compound of the disclosure together, and/or in admixture, with at least one pharmaceutical carrier or diluent. These pharmaceutical compositions may be used in the prevention or treatment of the foregoing diseases or conditions.

The carrier is pharmaceutically acceptable and must be compatible with, i.e. not have a deleterious effect upon, the other ingredients in the composition. The carrier may be a solid or liquid and is preferably formulated as a unit dose formulation, for example, a tablet which may contain from 0.05 to 95% by weight of the active ingredient. If desired, other physiologically active ingredients may also be incorporated in the pharmaceutical compositions of the disclosure.

In addition to the ingredients specifically mentioned above, the formulations of the present disclosure may include other agents known to those skilled in the art of pharmacy, having regard for the type of formulation in issue. For example, formulations suitable for oral administration may include flavoring agents and formulations suitable for intranasal administration may include perfumes.

In one of the embodiments, the present disclosure provides a pharmaceutical composition comprising the compounds of formula I and a pharmaceutically acceptable carrier or excipient.

Methods of Treatment

The compounds of the disclosure (e.g., compounds of formula I, Ia, Ib, I-9, II, III, IIIa, IIIb, C2, D5, 44, 44a, 45, and 100) are useful for therapy in subjects such as mammals, including humans. In particular, the compounds of the disclosure are useful in a method of treating or preventing a disease or condition in a subject comprising administering to the subject in need thereof an effective amount of a compound of the disclosure or a pharmaceutically acceptable salt, solvate, or amino acid conjugate thereof. In one embodiment, the disease or condition is FXR-mediated (e.g., FXR plays a role in the initiation or progress of the disease or condition). In one embodiment, the disease or condition is mediated by decreased FXR activity. In one embodiment, the disease or condition is selected from cardiovascular disease, chronic liver disease, lipid disorder, gastrointestinal disease, renal disease, metabolic disease, cancer, and neurological disease.

In one embodiment, the disclosure relates to a method of treating or preventing cardiovascular disease in a subject, comprising administering to the subject in need thereof an effective amount of a compound of the disclosure or a pharmaceutically acceptable salt, solvate, or amino acid conjugate thereof. In one embodiment, the disclosure relates to a method of treating cardiovascular disease. In one embodiment, cardiovascular disease selected from atherosclerosis, arteriosclerosis, dyslipidemia, hypercholesteremia, hyperlipidemia, hyperlipoproteinemia, and hypertriglyceridemia.

The term "hyperlipidemia" refers to the presence of an abnormally elevated level of lipids in the blood. Hyperlipidemia can appear in at least three forms: (1) hypercholesterolemia, i.e., an elevated cholesterol level; (2) hypertriglyceridemia, i.e., an elevated triglyceride level; and (3) combined hyperlipidemia, i.e., a combination of hypercholesterolemia and hypertriglyceridemia.

The term "dyslipidemia" refers to abnormal levels of lipoproteins in blood plasma including both depressed and/or elevated levels of lipoproteins (e.g., elevated levels of LDL, VLDL and depressed levels of HDL).

In one embodiment, the disclosure relates to a method selected from reducing cholesterol levels or modulating cholesterol metabolism, catabolism, absorption of dietary cholesterol, and reverse cholesterol transport in a subject, comprising administering to the subject in need thereof an effective amount of a compound of the disclosure or a pharmaceutically acceptable salt, solvate, or amino acid conjugate or prodrug thereof.

In another embodiment, the disclosure relates to a method of treating or preventing a disease affecting cholesterol, triglyceride, or bile acid levels in a subject, comprising administering to the subject in need thereof an effective amount of a compound of the disclosure or a pharmaceutically acceptable salt, solvate, or amino acid conjugate thereof.

In one embodiment, the disclosure relates to a method of lowering triglycerides in a subject, comprising administering to the subject in need thereof an effective amount of a compound of the disclosure or a pharmaceutically acceptable salt, solvate, or amino acid conjugate thereof.

In one embodiment, the disclosure relates to a method of treating or preventing a disease state associated with an elevated cholesterol level in a subject, comprising administering to the subject in need thereof an effective amount of a compound of the disclosure or a pharmaceutically acceptable salt, solvate, or amino acid conjugate thereof. In one embodiment, the disclosure relates to a method of treating a disease state associated with an elevated cholesterol level in a subject. In one embodiment, the disclosure relates to a method of preventing a disease state associated with an elevated cholesterol level in a subject. In one embodiment, the disease state is selected from coronary artery disease, angina pectoris, carotid artery disease, strokes, cerebral arteriosclerosis, and xanthoma.

In one embodiment, the disclosure relates to a method of treating or preventing a lipid disorder in a subject, comprising administering to the subject in need thereof an effective amount of a compound of the disclosure or a pharmaceutically acceptable salt, solvate, or amino acid conjugate thereof. In one embodiment, the disclosure relates to a method of treating a lipid disorder. In one embodiment, the disclosure relates to a method of preventing a lipid disorder.

Lipid disorders are the term for abnormalities of cholesterol and triglycerides. Lipid abnormalities are associated with an increased risk for vascular disease, and especially heart attacks and strokes. Abnormalities in lipid disorders are a combination of genetic predisposition as well as the nature of dietary intake. Many lipid disorders are associated with being overweight. Lipid disorders may also be associated with other diseases including diabetes, the metabolic syndrome (sometimes called the insulin resistance syndrome), underactive thyroid or the result of certain medications (such as those used for anti-rejection regimens in people who have had transplants).

In one embodiment, the disclosure relates to a method of treating or preventing one or more symptoms of disease affecting lipid metabolism (i.e., lipodystrophy) in a subject, comprising administering to the subject in need thereof an effective amount of a compound of the disclosure or a pharmaceutically acceptable salt, solvate, or amino acid conjugate thereof. In one embodiment, the disclosure relates to a method of treating one or more symptoms of a disease affecting lipid metabolism. In one embodiment, the disclosure relates to a method of preventing one or more symptoms of a disease affecting lipid metabolism.

In one embodiment, the disclosure relates to a method of decreasing lipid accumulation in a subject, comprising administering to the subject in need thereof an effective amount of a compound of the disclosure or a pharmaceutically acceptable salt, solvate, or amino acid conjugate thereof.

In one embodiment, the disclosure relates to a method of treating or preventing liver disease in a subject, comprising administering to the subject in need thereof an effective amount of a compound of the disclosure or a pharmaceutically acceptable salt, solvate, or amino acid conjugate thereof. In one embodiment, the disclosure relates to a method of treating chronic liver disease. In one embodiment, the disclosure relates to a method of preventing chronic liver disease. In one embodiment, the FXR mediated liver disease is selected from a cholestatic liver disease such as primary biliary cirrhosis (PBC) also known as primary biliary cholangitis (PBC), primary sclerosing cholangitis (PSC), chronic liver disease, nonalcoholic fatty liver disease (NAFLD), nonalcoholic steatohepatitis (NASH), hepatitis C infection, alcoholic liver disease, liver damage due to progressive fibrosis, and liver fibrosis. Other examples of FXR mediated diseases also include portal hypertension, bile acid diarrhea, hyperlipidemia, high LDL-cholesterol, high HDL cholesterol, high triglycerides, and cardiovascular disease. Other liver diseases include cerebrotendinous xanthomatosis (CTX), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, and alpha 1-antitrypsin deficiency.

In one embodiment, the disclosure relates to a method of treating or preventing one or more symptoms of cholestasis, including complications of cholestasis in a subject, comprising administering to the subject in need thereof an effective amount of a compound of the disclosure or a pharmaceutically acceptable salt, solvate, or amino acid conjugate or prodrug thereof. In one embodiment, the disclosure relates to a method of treating one or more symptoms of cholestasis. In one embodiment, the disclosure relates to preventing one or more symptoms of cholestasis.

Cholestasis is typically caused by factors within the liver (intrahepatic) or outside the liver (extrahepatic) and leads to the accumulation of bile salts, bile pigment bilirubin, and lipids in the blood stream instead of being eliminated normally. Intrahepatic cholestasis is characterized by widespread blockage of small ducts or by disorders, such as hepatitis, that impair the body's ability to eliminate bile. Intrahepatic cholestasis may also be caused by alcoholic liver disease, primary biliary cirrhosis, cancer that has spread (metastasized) from another part of the body, primary sclerosing cholangitis, gallstones, biliary colic, and acute cholecystitis. It can also occur as a complication of surgery, serious injury, cystic fibrosis, infection, or intravenous feeding or be drug induced. Cholestasis may also occur as a complication of pregnancy and often develops during the second and third trimesters. Extrahepatic cholestasis is most often caused by choledocholithiasis (Bile Duct Stones), benign biliary strictures (non-cancerous narrowing of the common duct), cholangiocarcinoma (ductal carcinoma), and pancreatic carcinoma. Extrahepatic cholestasis can occur as a side effect of many medications.

A compound of the disclosure may be used for treating or preventing one or more symptoms of intrahepatic or extrahepatic cholestasis, including without limitation, biliary atresia, obstetric cholestasis, neonatal cholestasis, drug induced cholestasis, cholestasis arising from Hepatitis C infection, chronic cholestatic liver disease such as primary biliary cirrhosis (PBC), and primary sclerosing cholangitis (PSC).

In one embodiment, the disclosure relates to a method of enhancing liver regeneration in a subject, comprising administering to the subject in need thereof an effective amount of a compound of the disclosure or a pharmaceutically acceptable salt, solvate, or amino acid conjugate or prodrug thereof. In one embodiment, the method is enhancing liver regeneration for liver transplantation.

In one embodiment, the disclosure relates to a method of treating or preventing fibrosis in a subject, comprising administering to the subject in need thereof an effective amount of a compound of the disclosure or a pharmaceutically acceptable salt, solvate, or amino acid conjugate or prodrug thereof. In one embodiment, the disclosure relates to a method of treating fibrosis. In one embodiment, the disclosure relates to a method of preventing fibrosis.

Accordingly, as used herein, the term fibrosis refers to all recognized fibrotic disorders, including fibrosis due to pathological conditions or diseases, fibrosis due to physical trauma ("traumatic fibrosis"), fibrosis due to radiation damage, and fibrosis due to exposure to chemotherapeutics. As used herein, the term "organ fibrosis" includes but is not limited to liver fibrosis, fibrosis of the kidneys, fibrosis of lung, and fibrosis of the intestine. "Traumatic fibrosis" includes but is not limited to fibrosis secondary to surgery (surgical scarring), accidental physical trauma, burns, and hypertrophic scarring.

As used herein, "liver fibrosis" includes liver fibrosis due to any cause, including but not limited to virally-induced liver fibrosis such as that due to hepatitis B or C virus; exposure to alcohol (alcoholic liver disease), certain pharmaceutical compounds including but not limited to methotrexate, some chemotherapeutic agents, and chronic ingestion of arsenicals or vitamin A in megadoses, oxidative stress, cancer radiation therapy or certain industrial chemicals including but not limited to carbon tetrachloride and dimethylnitrosamine; and diseases such as primary biliary cirrhosis, primary sclerosing cholangitis, fatty liver, obesity, non-alcoholic steatohepatitis, cystic fibrosis, hemochromatosis, auto-immune hepatitis, and steatohepatitis. Current therapy in liver fibrosis is primarily directed at removing the causal agent, e.g., removing excess iron (e.g., in the case of hemochromatosis), decreasing viral load (e.g., in the case of chronic viral hepatitis), or eliminating or decreasing exposure to toxins (e.g., in the case of alcoholic liver disease). Anti-inflammatory drugs such as corticosteroids and colchicine are also known for use in treating inflammation that can lead to liver fibrosis. As is known in the art, liver fibrosis may be clinically classified into five stages of severity (S0, S1, S2, S3, and S4), usually based on histological examination of a biopsy specimen. S0 indicates no fibrosis, whereas S4 indicates cirrhosis. While various criteria for staging the severity of liver fibrosis exist, in general early stages of fibrosis are identified by discrete, localized areas of scarring in one portal (zone) of the liver, whereas later stages of fibrosis are identified by bridging fibrosis (scarring that crosses zones of the liver).

In one embodiment, the disclosure relates to a method of treating or preventing organ fibrosis in a subject, comprising administering to the subject in need thereof an effective amount of a compound of the disclosure or a pharmaceutically acceptable salt, solvate, or amino acid conjugate thereof. In one embodiment, the fibrosis is liver fibrosis.

In one embodiment, the disclosure relates to a method of treating or preventing gastrointestinal disease in a subject, comprising administering to the subject in need thereof an effective amount of a compound of the disclosure or a pharmaceutically acceptable salt, solvate, or amino acid conjugate or prodrug thereof. In one embodiment, the disclosure relates to a method of treating gastrointestinal disease. In one embodiment, the disclosure relates to a method of preventing gastrointestinal disease. In one embodiment, the gastrointestinal disease is selected from inflammatory bowel disease (IBD), irritable bowel syndrome (IBS), bacterial overgrowth, malabsorption, post-radiation colitis, and microscopic colitis. In one embodiment, the inflammatory bowel disease is selected from Crohn's disease and ulcerative colitis.

In one embodiment, the disclosure relates to a method of treating or preventing renal disease in a subject, comprising administering to the subject in need thereof an effective amount of a compound of the disclosure or a pharmaceutically acceptable salt, solvate, or amino acid conjugate thereof. In one embodiment, the disclosure relates to a method of treating renal disease. In one embodiment, the disclosure relates to a method of preventing renal disease. In one embodiment, the renal disease is selected from diabetic nephropathy, focal segmental glomerulosclerosis (FSGS), hypertensive nephrosclerosis, chronic glomerulonephritis, chronic transplant glomerulopathy, chronic interstitial nephritis, and polycystic kidney disease.

In one embodiment, the disclosure relates to a method of treating or preventing metabolic disease in a subject, comprising administering to the subject in need thereof an effective amount of a compound of the disclosure or a pharmaceutically acceptable salt, solvate, or amino acid conjugate thereof. In one embodiment, the disclosure relates to a method of treating renal disease. In one embodiment, the disclosure relates to a method of preventing renal disease. In one embodiment, the metabolic disease is selected from insulin resistance, hyperglycemia, diabetes mellitus, diabesity, and obesity. In one embodiment, the diabetes mellitus is type I diabetes. In one embodiment, the diabetes mellitus is type II diabetes.

Diabetes mellitus, commonly called diabetes, refers to a disease or condition that is generally characterized by metabolic defects in production and utilization of glucose which result in the failure to maintain appropriate blood sugar levels in the body.

In the case of type II diabetes, the disease is characterized by insulin resistance, in which insulin loses its ability to exert its biological effects across a broad range of concentrations. This resistance to insulin responsiveness results in insufficient insulin activation of glucose uptake, oxidation and storage in muscle and inadequate insulin repression of lipolysis in adipose tissue and of glucose production and secretion in liver. The resulting condition is elevated blood glucose, which is called "hyperglycemia". Uncontrolled hyperglycemia is associated with increased and premature mortality due to an increased risk for microvascular and macrovascular diseases, including retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys), hypertension, cerebrovascular disease, and coronary heart disease. Therefore, control of glucose homeostasis is a critically important approach for the treatment of diabetes.

Insulin resistance has been hypothesized to unify the clustering of hypertension, glucose intolerance, hyperinsulinemia, increased levels of triglyceride and decreased HDL cholesterol, and central and overall obesity. The association of insulin resistance with glucose intolerance, an increase in plasma triglyceride and a decrease in high-density lipoprotein cholesterol concentrations, hypertension, hyperuricemia, smaller denser low-density lipoprotein particles, and higher circulating levels of plasminogen activator inhibitor-1, has been referred to as "Syndrome X". Accordingly, methods of treating or preventing any disorders related to insulin resistance including the cluster of disease states, conditions or disorders that make up "Syndrome X" are provided. In one embodiment, the disclosure relates to a method of treating or preventing metabolic syndrome in a subject, comprising administering to the subject in need thereof an effective amount of a compound of the disclosure or a pharmaceutically acceptable salt, solvate, or amino acid conjugate thereof. In one embodiment, the disclosure relates to a method of treating metabolic syndrome. In another embodiment, the disclosure relates to a method of preventing metabolic syndrome.

In one embodiment, the disclosure relates to a method of treating or preventing cancer in a subject, comprising administering to the subject in need thereof an effective amount of a compound of the disclosure or a pharmaceutically acceptable salt, solvate, or amino acid conjugate thereof. In one embodiment, the disclosure relates to a method of treating cancer. In one embodiment, the disclosure relates to a method of preventing cancer. In one embodiment, the cancer is selected from hepatocellular carcinoma, colorectal cancer, gastric cancer, renal cancer, prostate cancer, adrenal cancer, pancreatic cancer, breast cancer, bladder cancer, salivary gland cancer, ovarian cancer, uterine body cancer, and lung cancer. In one embodiment, the cancer is hepatocellular carcinoma. In one embodiment, the cancer is colorectal cancer. In one embodiment, the cancer is gastric cancer. In one embodiment, the cancer is renal cancer. In one embodiment, the cancer is prostate cancer. In one embodiment, the cancer is adrenal cancer. In one embodiment, the cancer is pancreatic cancer. In one embodiment, the cancer is breast cancer. In one embodiment, the cancer is bladder cancer. In one embodiment, the cancer is salivary gland cancer. In one embodiment, the cancer is ovarian cancer. In one embodiment, the cancer is uterine body cancer. In one embodiment, the cancer is lung cancer.

In another embodiment, at least one of an agent selected from Sorafenib, Sunitinib, Erlotinib, or Imatinib is coadministered with the compound of the disclosure to treat cancer. In one embodiment, at least one of an agent selected from Abarelix, Aldesleukin, Allopurinol, Altretamine, Amifostine, Anastozole, Bevacizumab, Capecitabine, Carboplatin, Cisplatin, Docetaxel, Doxorubicin, Erlotinib, Exemestane, 5-Fluorouracil, Fulvestrant, Gemcitabine, Goserelin Acetate, Irinotecan, Lapatinib Ditosylate, Letozole, Leucovorin, Levamisole, Oxaliplatin, Paclitaxel, Panitumumab, Pemetrexed Disodium, Profimer Sodium, Tamoxifen, Topotecan, and Trastuzumab is co-administered with the compound of the disclosure to treat cancer.

Appropriate treatment for cancers depends on the type of cell from which the tumor derived, the stage and severity of the malignancy, and the genetic abnormality that contributes to the tumor.

Cancer staging systems describe the extent of cancer progression. In general, the staging systems describe how far the tumor has spread and puts patients with similar prognosis and treatment in the same staging group. In general, there are poorer prognoses for tumors that have become invasive or metastasized.

In one type of staging system, cases are grouped into four stages, denoted by Roman numerals I to IV. In stage I, cancers are often localized and are usually curable. Stage II and IIIA cancers are usually more advanced and may have invaded the surrounding tissues and spread to lymph nodes. Stage IV cancers include metastatic cancers that have spread to sites outside of lymph nodes.

Another staging system is TNM staging which stands for the categories: Tumor, Nodes, and Metastases. In this system, malignancies are described according to the severity of the individual categories. For example, T classifies the extent of a primary tumor from 0 to 4 with 0 representing a malignancy that does not have invasive activity and 4 representing a malignancy that has invaded other organs by extension from the original site. N classifies the extent of lymph node involvement with 0 representing a malignancy with no lymph node involvement and 4 representing a malignancy with extensive lymph node involvement. M classifies the extent of metastasis from 0 to 1 with 0 representing a malignancy with no metastases and 1 representing a malignancy with metastases.

These staging systems or variations of these staging systems or other suitable staging systems may be used to describe a tumor such as hepatocellular carcinoma. Few options only are available for the treatment of hepatocellular cancer depending on the stage and features of the cancer. Treatments include surgery, treatment with Sorafenib, and targeted therapies. In general, surgery is the first line of treatment for early stage localized hepatocellular cancer. Additional systemic treatments may be used to treat invasive and metastatic tumors.

In one embodiment, the disclosure relates to a method of treating or preventing gallstones in a subject, comprising administering to the subject in need thereof an effective amount of a compound of the disclosure or a pharmaceutically acceptable salt, solvate, or amino acid conjugate thereof. In one embodiment, the disclosure relates to a method of treating gallstones. In one embodiment, the disclosure relates to a method of preventing gallstones.

A gallstone is a crystalline concretion formed within the gallbladder by accretion of bile components. These calculi are formed in the gallbladder but may distally pass into other parts of the biliary tract such as the cystic duct, common bile duct, pancreatic duct, or the ampulla of Vater. Rarely, in cases of severe inflammation, gallstones may erode through the gallbladder into adherent bowel potentially causing an obstruction termed gallstone ileus. Presence of gallstones in the gallbladder may lead to acute cholecystitis, an inflammatory condition characterized by retention of bile in the gallbladder and often secondary infection by intestinal microorganisms, predominantly *Escherichia coli*, and *Bacteroides* species.

Presence of gallstones in other parts of the biliary tract can cause obstruction of the bile ducts, which can lead to serious conditions such as ascending cholangitis or pancreatitis. In one embodiment, the disclosure relates to a method of treating or preventing cholesterol gallstone disease in a subject, comprising administering to the subject in need thereof an effective amount of a compound of the disclosure or a pharmaceutically acceptable salt, solvate, or amino acid conjugate thereof. In one embodiment, the disclosure relates to a method of treating cholesterol gallstone disease. In one embodiment, the disclosure relates to a method of preventing cholesterol gallstone disease.

In one embodiment, the disclosure relates to a method of treating or preventing neurological disease in a subject, comprising administering to the subject in need thereof an effective amount of a compound of the disclosure or a pharmaceutically acceptable salt, solvate, or amino acid conjugate thereof. In one embodiment, the disclosure relates to a method of treating neurological disease. In one embodiment, the disclosure relates to a method of preventing neurological disease. In one embodiment, the neurological disease is stroke.

In one embodiment, the disclosure relates to a method as described herein and further wherein, the compound is administered by a route selected from oral, parenteral, intramuscular, intranasal, sublingual, intratracheal, inhalation, ocular, vaginal, rectal, and intracerebroventricular. In one embodiment, the route is oral.

In one embodiment, the compound utilized in one or more of the methods described herein is an FXR agonist. In one embodiment, the compound is a selective FXR agonist. In another embodiment, the compound does not activate TGR5. In one embodiment, the compound does not activate other nuclear receptors involved in metabolic pathways (e.g., as measured by an AlphaScreen assay). In one embodiment, such other nuclear receptors involved in metabolic pathways are selected from LXRβ, PXR, CAR, PPARα, PPARδ, PPARγ, RAR, RARα, VDR, TR, PR, RXR, GR, and ER. In one embodiment, the compound induces apoptosis.

In one embodiment, the disclosure relates to a method of regulating the expression level of one or more genes involved in bile acid homeostasis.

In one embodiment, the disclosure relates to a method of down regulating the expression level of one or more genes selected from CYP7α1 and SREBP-IC in a cell by administering to the cell a compound of the disclosure. In one embodiment, the disclosure relates to a method of up regulating the expression level of one or more genes selected from OSTα, OSTβ, BSEP, SHP, UGT2B4, MRP2, FGF-19, PPARγ, PLTP, APOCII, and PEPCK in a cell by administering to the cell a compound of the disclosure.

The disclosure also relates to the manufacture of a medicament for treating or preventing a disease or condition (e.g., a disease or condition mediated by FXR), wherein the medicament comprises a compound of the disclosure or a pharmaceutically acceptable salt, solvate, or amino acid conjugate thereof. In one embodiment, the disclosure relates to the manufacture of a medicament for treating or preventing any one of the diseases or conditions described herein above, wherein the medicament comprises a compound of the disclosure or a pharmaceutically acceptable salt, solvate, or amino acid conjugate thereof.

The disclosure also relates to a composition for use in a method for treating or preventing a disease or condition (e.g., a disease or condition mediated by FXR), wherein the composition comprises a compound of the disclosure or a pharmaceutically acceptable salt, solvate, or amino acid conjugate thereof. In one embodiment, the disclosure relates to a composition for use in a method for treating or preventing any one of the diseases or conditions described herein above, wherein the composition comprises a compound of the disclosure or a pharmaceutically acceptable salt, solvate, or amino acid conjugate thereof.

The methods of the disclosure comprise the step of administering an effective amount of a compound of the disclosure. As used herein, the term an "effective amount" refers to an amount of a compound of the disclosure which is sufficient to achieve the stated effect. Accordingly, an effective amount of a compound of the disclosure used in a method for the prevention or treatment of FXR mediated diseases or conditions will be an amount sufficient to prevent or treat the FXR mediated disease or condition.

Similarly, an effective amount of a compound of the disclosure for use in a method for the prevention or treatment of a cholestatic liver disease or increasing bile flow will be an amount sufficient to increase bile flow to the intestine. The amount of the compound of the disclosure which is required to achieve the desired biological effect will depend on a number of factors such as the use for which it is intended, the means of administration, and the recipient, and will be ultimately at the discretion of the attendant physician or veterinarian. In general, a typical daily dose for the treatment of a FXR mediated disease and condition, for instance, may be expected to lie in the range of from about 0.01 mg/kg to about 100 mg/kg. This dose may be administered as a single unit dose or as several separate unit doses or as a continuous infusion. Similar dosages would be applicable for the treatment of other diseases, conditions and therapies including the prevention and treatment of cholestatic liver diseases.

In one of the embodiments, the present disclosure proves a method of treating or preventing a disease or condition in a subject in need thereof comprising administering an effective amount of the compound of formula I or a pharmaceutically acceptable salt, solvate, or amino acid conjugate thereof, and wherein the disease or condition is mediated by FXR.

In one of the embodiments, the present disclosure proves a method of treating or preventing a disease or condition in a subject in need thereof comprising administering an effective amount of the compound of formula I, wherein the disease is selected from cardiovascular disease, chronic liver disease, lipid disorder, gastrointestinal disease, renal disease, metabolic disease, cancer, and neurological disease.

In one of the embodiments, the present disclosure proves a method of treating or preventing a disease or condition in a subject in need thereof comprising administering an effective amount of the compound of formula I, wherein the disease is cardiovascular disease selected from atherosclerosis, arteriosclerosis, dyslipidemia, hypercholesteremia, hyperlipidemia, hyperlipoproteinemia, and hypertriglyceridemia.

In one of the embodiments, the present disclosure proves a method of treating or preventing a disease or condition in a subject in need thereof comprising administering an effective amount of the compound of formula I, wherein the disease is liver disease selected from a cholestatic liver disease such as primary biliary cirrhosis (PBC) also known as primary biliary cholangitis (PBC), primary sclerosing cholangitis (PSC), chronic liver disease, nonalcoholic fatty liver disease (NAFLD), nonalcoholic steatohepatitis (NASH), hepatitis C infection, alcoholic liver disease, liver damage due to progressive fibrosis, and liver fibrosis. Other examples of FXR mediated diseases also include portal hypertension, bile acid diarrhea, hyperlipidemia, high LDL-cholesterol, high HDL cholesterol, high triglycerides, and cardiovascular disease. Other liver diseases include cerebrotendinous xanthomatosis (CTX), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, and alpha 1-antitrypsin deficiency.

In one of the embodiments, the present disclosure proves a method of treating or preventing a disease or condition in a subject in need thereof comprising administering an effective amount of the compound of formula I, wherein the disease is gastrointestinal disease selected from inflammatory bowel disease (IBD), irritable bowel syndrome (IBS), bacterial overgrowth, malabsorption, post-radiation colitis, and microscopic colitis.

In one of the embodiments, the present disclosure proves a method of treating or preventing a disease or condition in a subject in need thereof comprising administering an effective amount of the compound of formula I, wherein the inflammatory bowel disease is Crohn's disease or ulcerative colitis.

In one of the embodiments, the present disclosure proves a method of treating or preventing a disease or condition in a subject in need thereof comprising administering an effective amount of the compound of formula I, wherein the disease is renal disease selected from diabetic nephropathy, focal segmental glomerulosclerosis (FSGS), hypertensive nephrosclerosis, chronic glomerulonephritis, chronic transplant glomerulopathy, chronic interstitial nephritis, and polycystic kidney disease.

In one of the embodiments, the present disclosure proves a method of treating or preventing a disease or condition in a subject in need thereof comprising administering an effective amount of the compound of formula I, wherein the disease is metabolic disease selected from insulin resistance, hyperglycemia, diabetes mellitus, diabesity, and obesity.

In one of the embodiments, the present disclosure proves a method of treating or preventing a disease or condition in a subject in need thereof comprising administering an effective amount of the compound of formula I, wherein the disease is cancer selected from hepatocellular carcinoma, colorectal cancer, gastric cancer, renal cancer, prostate cancer, adrenal cancer, pancreatic cancer, breast cancer, bladder cancer, salivary gland cancer, ovarian cancer, uterine body cancer, and lung cancer.

EXAMPLES

The following examples are intended to illustrate certain embodiments of the present invention, but do not exemplify the full scope of the invention.

Example 1. Synthesis of Compound 100
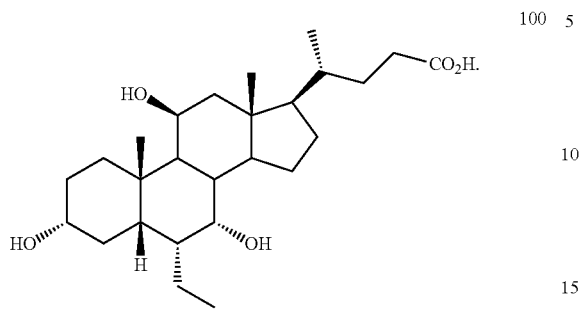
Exemplary Route 1:
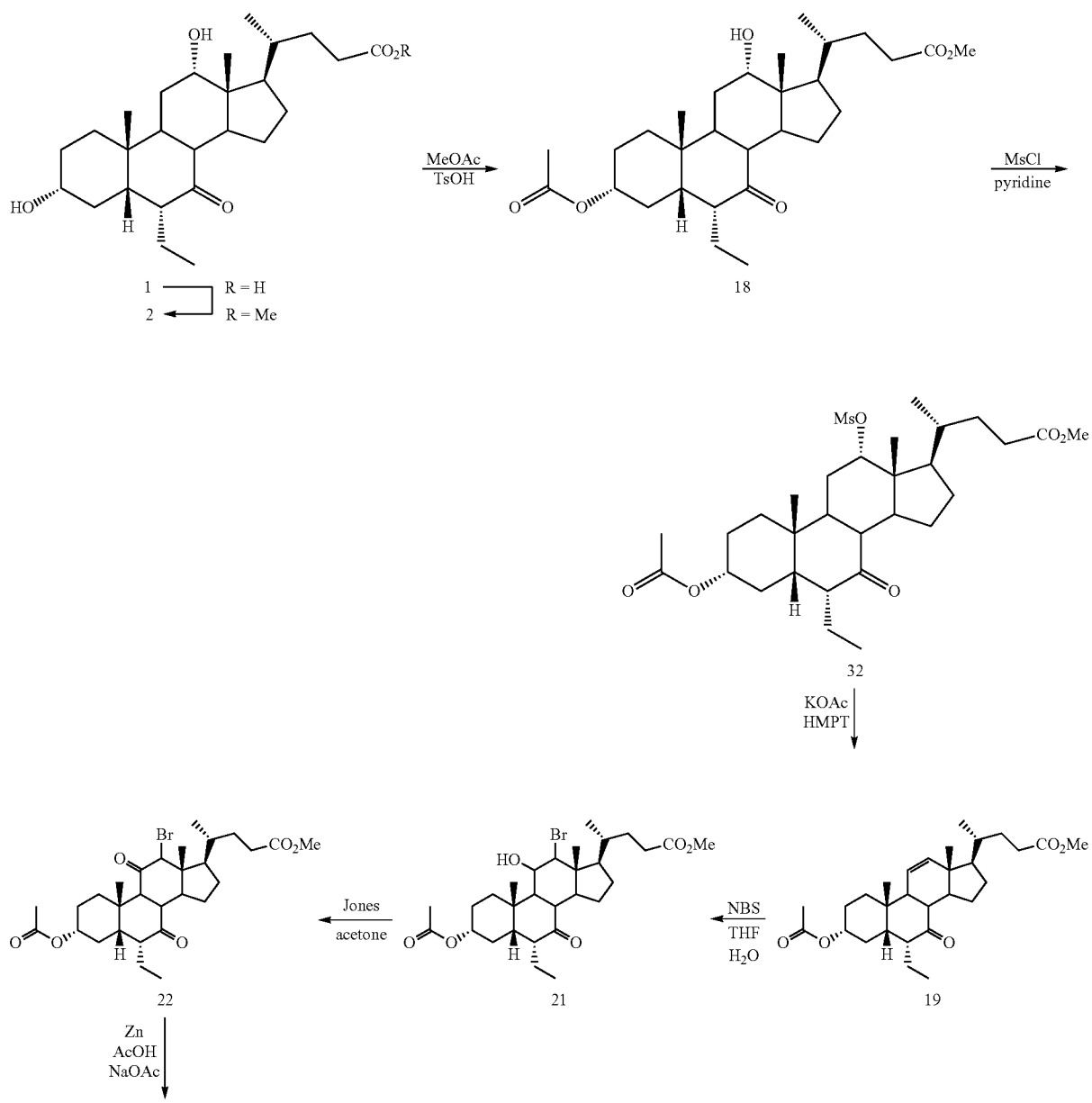

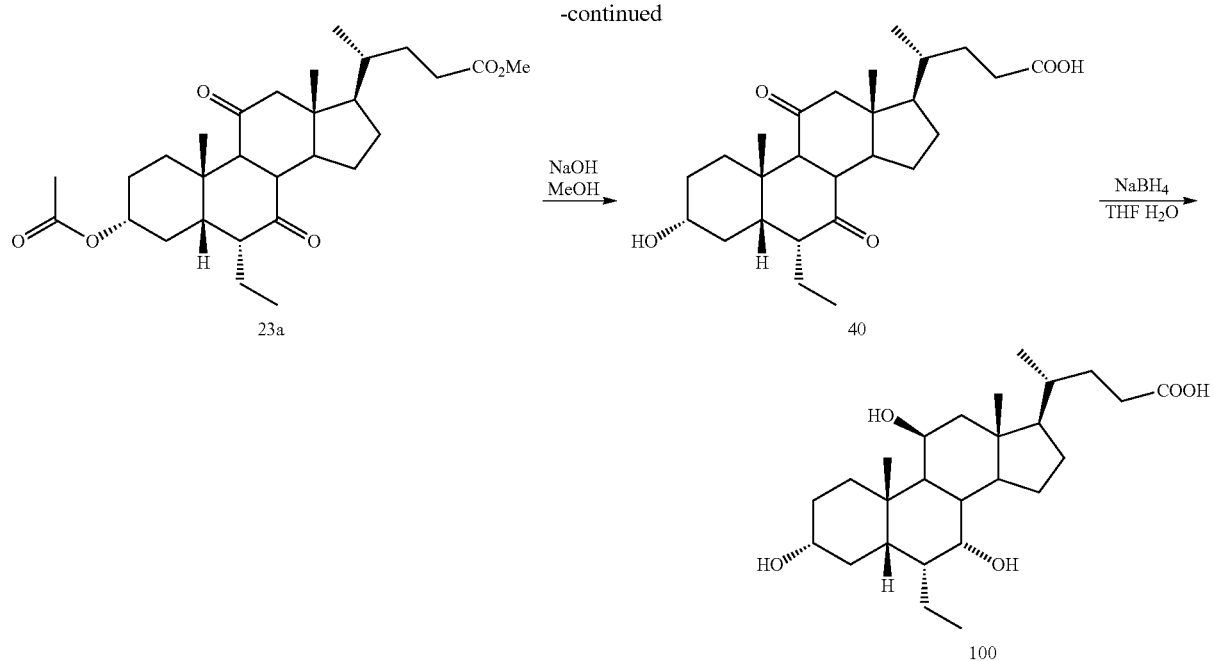
Exemplary Route 2:
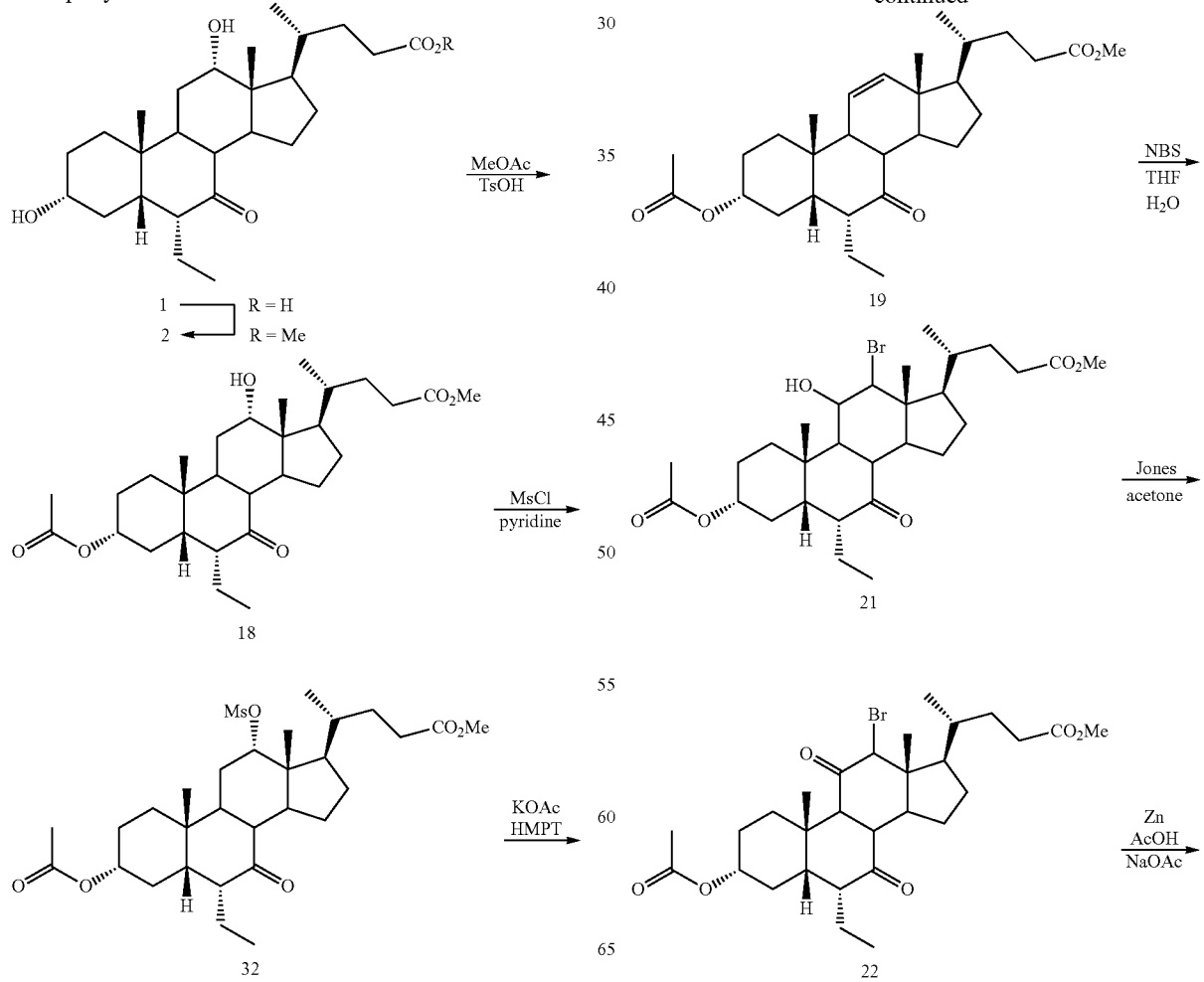

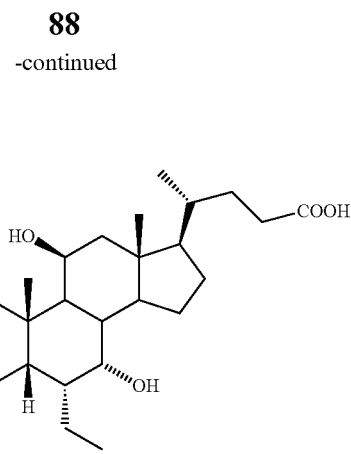
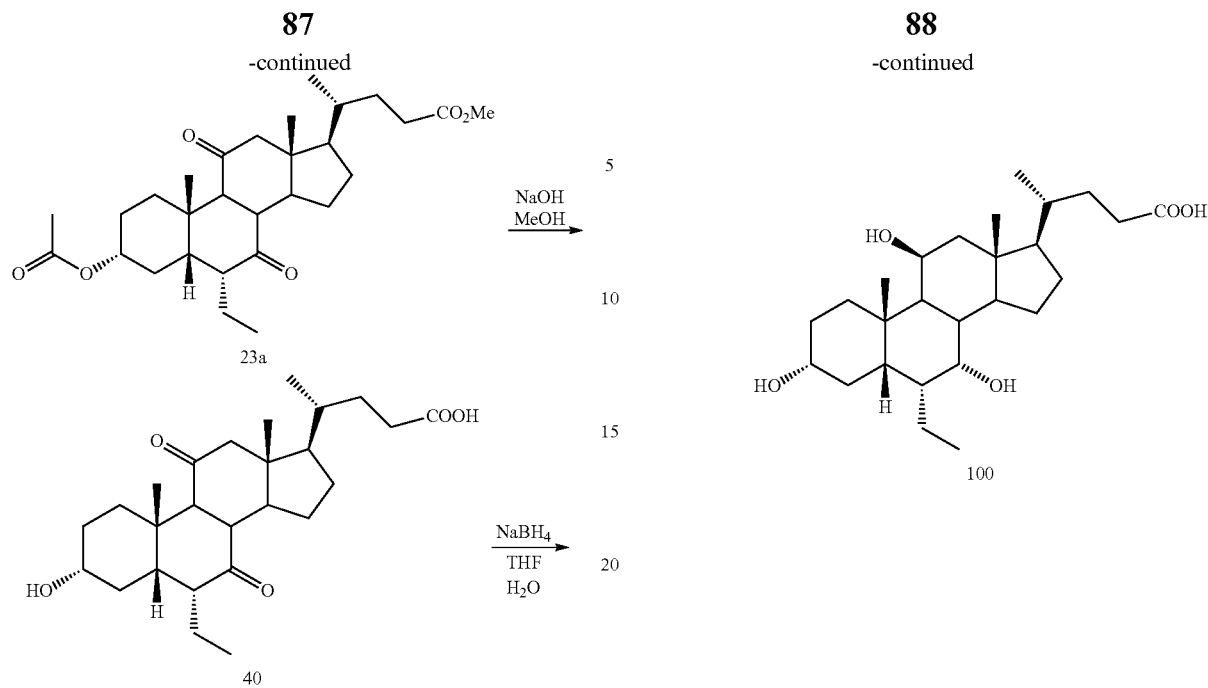
Exemplary Route 3:
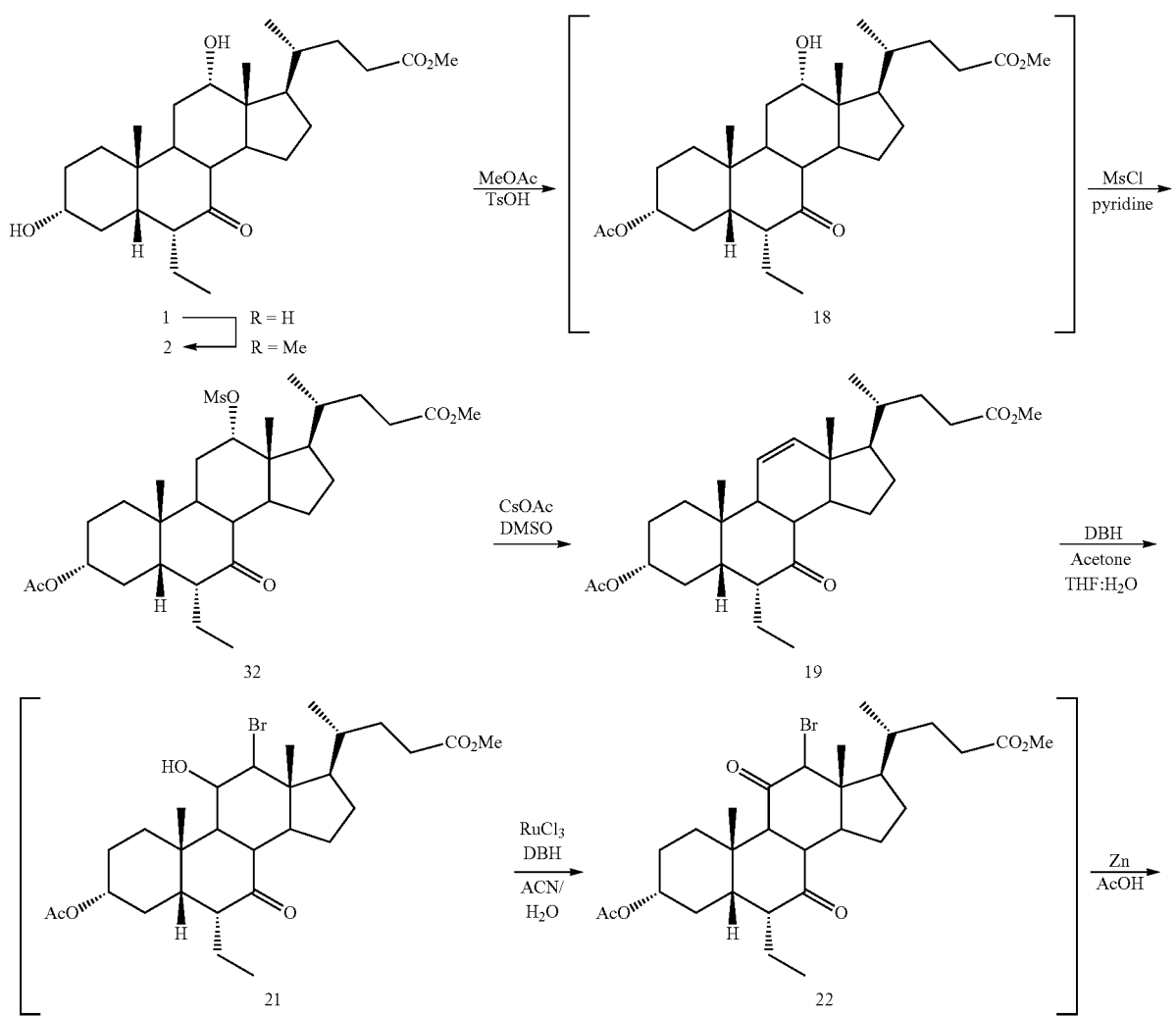

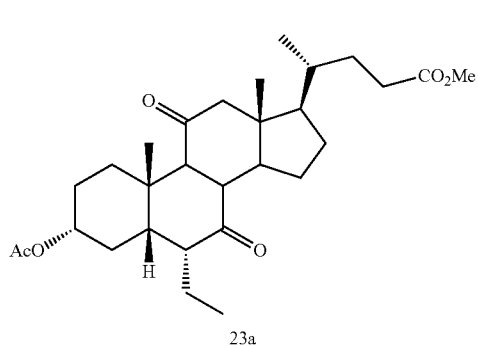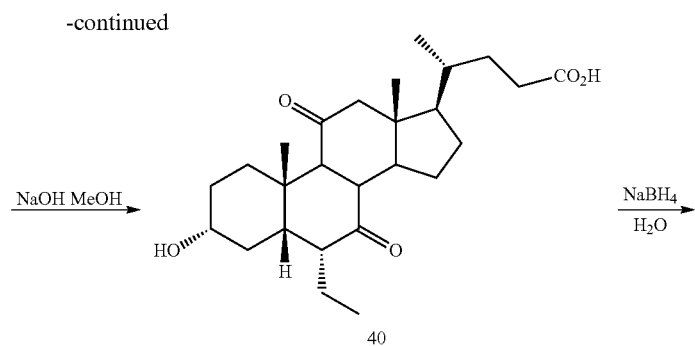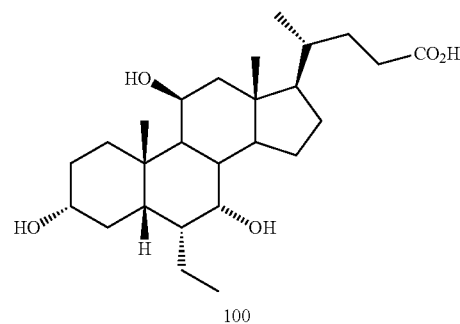
Routes 1-3 can be also carried out with other protecting groups at C3 hydroxy.
Exemplary Route 4:
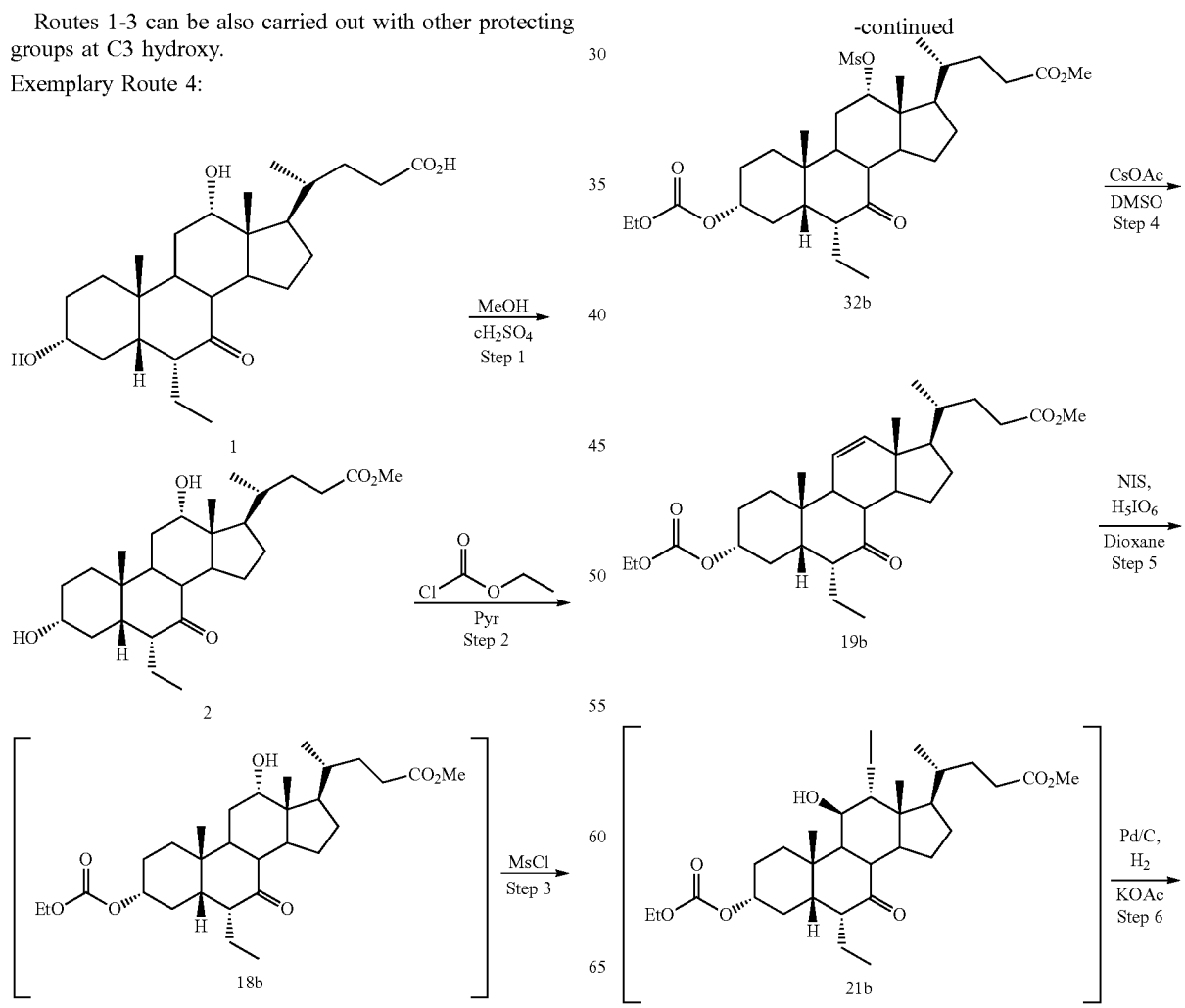

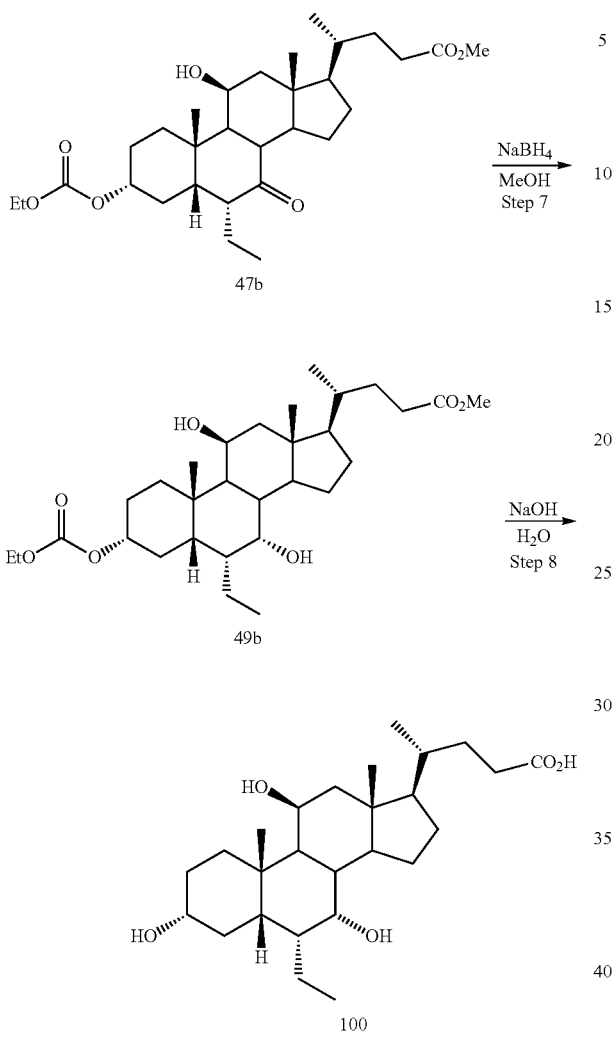

Route 4 can be also carried out with other protecting groups at C3 hydroxy (e.g., OAc).

Example 1-1: Methyl 3α,12α-dihydroxy-6α-ethyl-7-oxo-5β-cholan-24-oate (2)

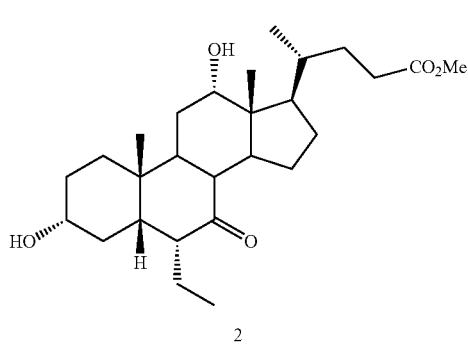

To a stirring solution of 6-ethyl-7-ketocholic acid (1, 25 g, 57.52 mmol) in CH$_2$Cl$_2$ (340 mL) was added MeOH (23 mL) followed by pTSA.H$_2$O (1.1 g, 5.75 mmol). The resulting solution was heated at 40° C. for 20 h. The reaction mixture was poured into a mixture of brine (500 mL) and NaHCO$_3$ (1.5 g). CH$_2$Cl$_2$ (500 mL) and brine (200 mL) were added, the layers were separated, dried over Na$_2$SO$_4$, filtered and concentrated under reduced pressure to afford 24.91 g (97%) as an off-white solid (compound 2). ES-API Pos: 466.2 [M+H$_2$O]. $^1$H-NMR (300 MHz, CDCl$_3$): δ 0.68 (s, 3H, 18-CH$_3$), 0.80 (t, 3H, 26-CH$_3$), 0.96 (d, 3H, 21-CH$_3$), 1.20 (s, 3H, 19-CH$_3$), 3.43-3.59 (3, 1H, 3-CH), 3.66 (s, 3H, CO$_2$CH$_3$), 3.99 (br. s, 1H, 12-CH).

Alternate Procedure of Making Compound 2:

To a suspension of 6-ethyl-7-ketocholic acid (1, 2.5 kg, 5.75 mol) in MeOH (12 L) was added conc. H$_2$SO$_4$ (16.1 mL; 0.29 mol) and the mixture was heated to 65° C. for 3 h. The mixture was cooled, the pH was adjusted with 1N NaOH (aq) to ca. pH 9, and water (12.5 L) was added to precipitate product. The solids were filtered, washed with 1:1 MeOH-water and dried under vacuum. Compound 2 (2.37 kg) was produced in 91.8% yield. (e.g., Route 4).

Example 1-2: Methyl 3α-acetoxy-12α-hydroxy-6α-ethyl-7-oxo-5β-cholan-24-oate (18)

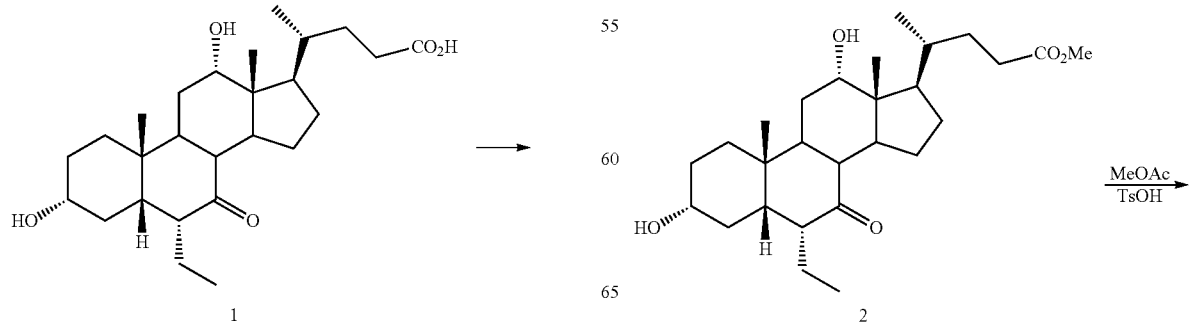

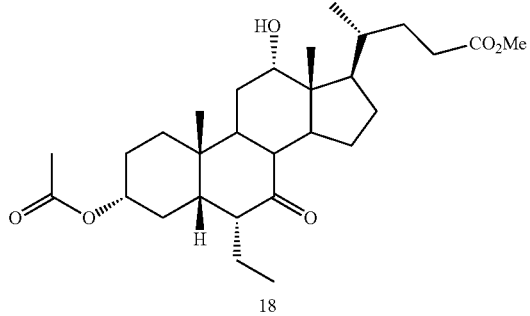

18

To a stirring suspension of compound 2 (24.9 g, 55.5 mmol) in MeOAc (660 mL) was added pTsOH.H$_2$O (1.01 g, 5.33 mmol). The resulting solution was heated at 75° C. for 4 days. EtOAc (950 mL) was added. The mixture was washed with saturated NaHCO$_3$, brine, dried over Na$_2$SO$_4$ and concentrated under reduced pressure to afford 27.2 g (quantitative yield) of compound 18 as a white foam. This material was used without purification for the next reaction step. ES-API Pos: 508.8 [M+H$_2$O]. $^1$H-NMR (400 MHz, CDCl$_3$): δ 0.67 (s, 3H, 18-CH$_3$), 0.78 (t, J=7.3 Hz, 3H, 26-CH$_3$), 0.96 (d, J=6.1 Hz, 3H, 21-CH$_3$), 1.20 (s, 3H, 19-CH$_3$), 1.98 (s, 3H, OCOCH$_3$), 3.65 (s, 3H, CO$_2$CH$_3$), 3.98 (s, 1H, 12-CH), 4.59-4.63 (m, 1H, 3-CH).

Alternate Procedure:

A solution of compound 2 (2.36 kg, 5.26 mol) in MeOAc (20 L) was added pTsOH.H$_2$O (100 g, 0.526 mol). The mixture was heated to reflux for 13-65 h, then solvents were distilled and fresh MeOAc was added and reflux continued. This was repeated three times until the reaction was complete. The mixture was concentrated and DCM (23.6 L) was added. The organic layer was washed with water (23.6 L), 8% NaHCO$_3$ (aq) (23.6 L) followed by saturated aqueous NaCl (11.8l). The organic layer was separated and dried over Na$_2$SO$_4$, then filtered and concentrated to a final volume of 11.7 L. The DCM solution of compound 18 was used directly in the next step.

Example 1-3: Methyl 3α-Acetoxy-6α-ethyl-7-keto-12α-((methylsulfonyl)oxy)-5β-cholan-24-oate (32)

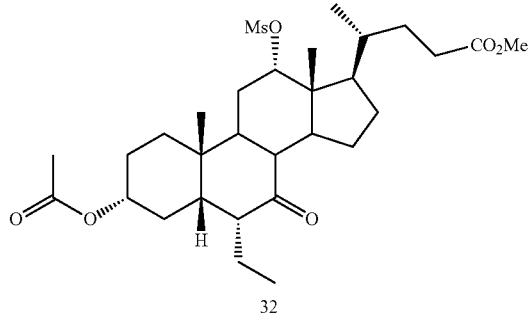

32

To a solution of compound 18 (27.2 g, 55.43 mmol) in pyridine (270 mL) at room temperature was added MsCl (8.58 mL, 110.87 mmol). The reaction was stirred at 20-30° C. overnight. The reaction mixture was poured into ice water and EtOAc (1 L) was added. The phases were separated and the aqueous phase was extracted with EtOAc (3×150 mL). The combined organic phases were washed with 2M aq. HCl (3×150 mL). The combined organic phases were washed with sat. NaHCO$_3$ (200 mL), dried over anhydrous Na$_2$SO$_4$, filtered and concentrated under reduced pressure. More EtOAc was added to remove the pyridine and the crude was dried under reduced pressure for three hours providing 31.13 g (99%) of product 32 as an off-white solid. $^1$H-NMR (400 MHz, CDCl$_3$): δ 0.75-0.81 (m, 6H, 18-CH$_3$, 26-CH$_3$), 0.96 (d, J=6.4 Hz, 3H, 21-CH$_3$), 1.21 (s, 3H, 19-CH$_3$), 2.01 (s, 3H, OCOCH$_3$), 3.04 (s, 3H, OSO$_2$CH$_3$), 3.67 (s, 3H, CO$_2$CH$_3$), 4.59-4.62 (m, 1H, 3-CH), 5.10 (s, 1H, 12-CH).

Alternative Procedure:

To a DCM solution of compound 18 (11.7 L, ca. 5.26 mol) was added pyridine (2.13 L, 26.3 mol) and MsCl (0.814 L, 10.52 mol) at 15-25° C. The mixture was stirred for 96 h, then diluted with DCM (12 L) and water (12 L). The organic layer was washed twice with 2N aq. HCl (12 L), 8% NaHCO$_3$ (aq) (12 L) then dried over Na$_2$SO$_4$, then concentrated to a final volume of 7.1 L. MTBE (24 L) was added in portions and concentrated to a final volume of 8 L. The resulting suspension was cooled and vacuum filtered. The solids were washed with 1:1 MTBE-heptane, then dried under vacuum to give compound 32 (2.576 kg) in 86.1% yield.

Alternatively, mesylate 32b can be prepared via a telescoped process, a one-pot procedure using ethyl chloroformate as a protecting group for C3-OH as shown in Example 1-3b. Ethyl carbonate protecting group which can be installed with high selectivity provides more crystalline solid and overcomes possible issues with completion of the reaction on larger scale. (Route 4)

Example 1-3a: Methyl 3α-(ethoxycarbonyl)oxy-12α-(methansulfonyl)oxy-6α-ethyl-7-oxo-5β-cholan-24-oate (32b)

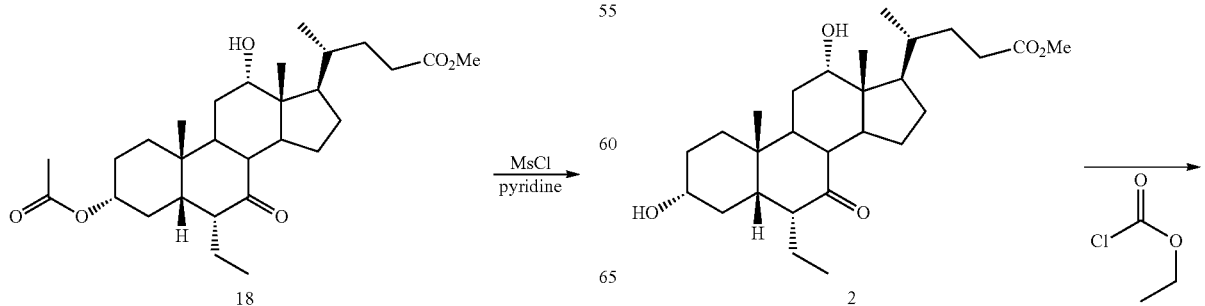

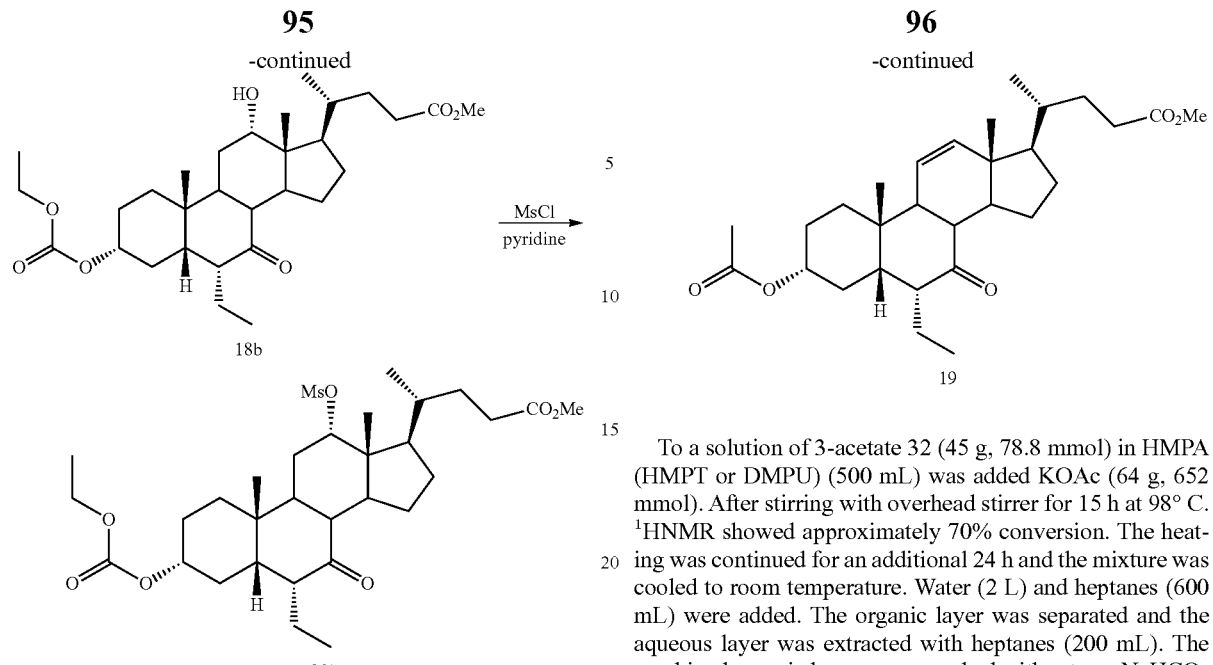

Methyl 3α,12α-dihydroxy-6α-ethyl-7-oxo-5β-cholan-24-oate (2)

(14.0 g, 31.2 mmol) was dissolved in pyridine (150 mL) and cooled to 0-5° C. Ethyl chloroformate, ClCO$_2$Et, (4.0 g, 37.4 mmol) was added and the mixture was stirred for 2 hours allowing to reach room temperature. Additional ClCO$_2$Et (1.5 g, 13.5 mmol) was added and stirring continued until the reaction was complete (within 16 hours). The mixture was cooled to 0-5° C. and MSCl (7.1 g, 62.4 mmol) was added, and the mixture was allowed to reach ambient temperature. Additional MSCl (3.5 g, 31.2 mmol) was added over 2 hours and stirring continued until reaction was complete (within 16 h). Heptanes (200 mL) were added followed by water (500 mL). The resulting suspension was stirred for 1 hour then vacuum filtered. The solids were triturated in heptanes/EtOAc (100 mL; 4:1) for 1 hour, filtered and washed with 25 mL of heptanes/EtOAc (4:1), then dried under vacuum. Compound 32b (14.7 g) was isolated as white solid in 83% yield. $^1$H-NMR (300 MHz, CDCl$_3$): δ 0.76 (s, 3H, 18-CH$_3$), 0.81 (t, 3H, 26-CH$_3$), 0.96 (d, 3H, 21-CH$_3$), 1.22 (s, 3H, 19-CH$_3$), 1.28 (t, J=7.3 Hz, 3H, OC(O)OCH$_2$CH$_3$), 3.04 (s, 3H, OSO$_2$CH$_3$), 3.66 (s, 3H, CO$_2$CH$_3$), 4.15 (q, 2H, OC(O)OCH$_2$CH$_3$), 4.39-4.56 (m, 1H, 3-CH), 5.10 (br. s, 1H, 12-CH). (e.g., Route 4).

Example 1-4: Methyl Δ$^{11,12}$-3α-Acetoxy-6α-ethyl-5β-cholan-24-oate (19)

To a solution of 3-acetate 32 (45 g, 78.8 mmol) in HMPA (HMPT or DMPU) (500 mL) was added KOAc (64 g, 652 mmol). After stirring with overhead stirrer for 15 h at 98° C. $^1$HNMR showed approximately 70% conversion. The heating was continued for an additional 24 h and the mixture was cooled to room temperature. Water (2 L) and heptanes (600 mL) were added. The organic layer was separated and the aqueous layer was extracted with heptanes (200 mL). The combined organic layers were washed with sat. aq. NaHCO$_3$ (300 mL) and brine (200 mL). The organic layer was dried over Na$_2$SO$_4$ treated with active carbon (3 g) and concentrated to provide 40 g (with some residual heptanes; about 98% yield) of crude compound 19. Material was of acceptable purity based on $^1$H-NMR. Material was analyzed by $^1$H-NMR and LCMS. ES-API Pos: 490.8 [M+H$_2$O]. $^1$H-NMR (400 MHz, CDCl$_3$): δ 0.74 (s, 3H, 18-CH$_3$), 0.82 (t, J=7.3 Hz, 3H, 26-CH$_3$), 1.00 (d, J=6.3 Hz, 3H, 21-CH$_3$), 1.16 (s, 3H, 19-CH$_3$), 2.02 (s, 3H, OCOCH$_3$), 3.66 (s, 3H, CO$_2$CH$_3$), 4.63-4.68 (m, 1H, 3-CH), 5.32 (d, J=10.3 Hz, 1H, 12-CH), 6.18 (dd, J$_1$=2.4 Hz, J$_2$=10.3 Hz, 1H, 11-CH).

Alternatively, compound 19 can be prepared according to the following procedure:

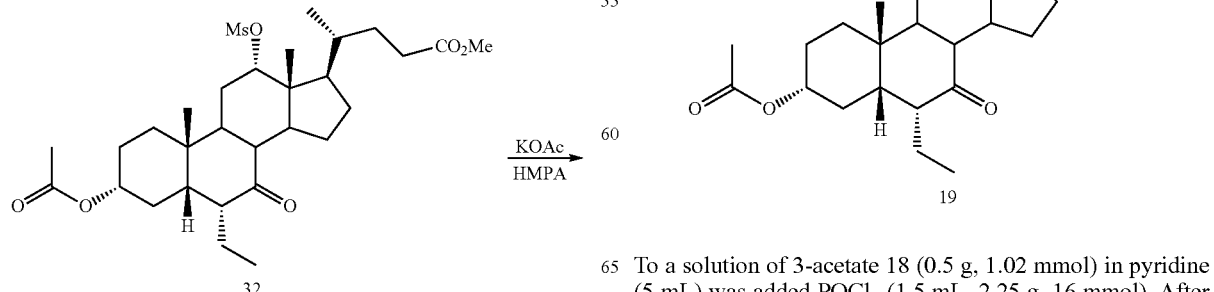

To a solution of 3-acetate 18 (0.5 g, 1.02 mmol) in pyridine (5 mL) was added POCl$_3$ (1.5 mL, 2.25 g, 16 mmol). After stirring overnight at 50° C. the mixture was cooled to room temperature. The mixture was poured in a mixture of ice (20 mL) and ethyl acetate (30 mL). To the mixture was added brine (10 mL). The organic layer was separated and washed with (HCl 4 N), sat. NaHCO$_3$ and brine. The organic layer was dried over Na$_2$SO$_4$ and concentrated providing 480 mg of compound 19 (approximately 80% yield by NMR and HPLC/ELSD). The product can be used for the next step without purification. The product was analyzed by $^1$H-NMR and LCMS. ES-API Pos: 490.8 [M+H$_2$O]. $^1$H-NMR (400 MHz, CDCl$_3$): δ 0.74 (s, 3H, 18-CH$_3$), 0.82 (t, J=7.3 Hz, 3H, 26-CH$_3$), 1.00 (d, J=6.3 Hz, 3H, 21-CH$_3$), 1.16 (s, 3H, 19-CH$_3$), 2.02 (s, 3H, OCOCH$_3$), 3.66 (s, 3H, CO$_2$CH$_3$), 4.63-4.68 (m, 1H, 3-CH), 5.32 (d, J=10.3 Hz, 1H, 12-CH), 6.18 (dd, J$_1$=2.4 Hz, J$_2$=10.3 Hz, 1H, 11-CH).

Alternatively, compound 19 can be prepared according to the following procedure:

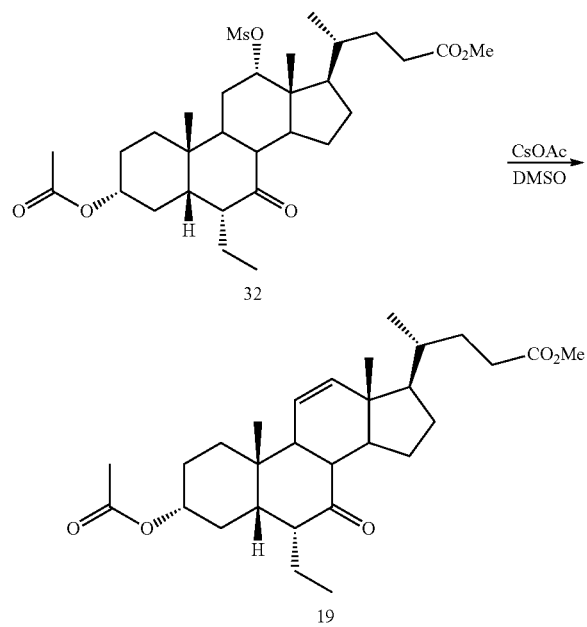

To a solution of compound 32 (2.59 kg, 4.55 mol) in DMSO (20.2 L) was added CsOAc (3.93 kg, 20.5 mol) and the mixture was heated to 90-100° C. for 16-20 h. The mixture was cooled to ambient temperature and added to cold water (62.1 L) over 0.5-1 h. The resulting suspension was filtered, washed with water (3×20 L), then dried under vacuum. The solids were taken up in EtOAc and chromatographed on silica gel (10% EtOAc-Heptane). The product-rich fractions were pooled and concentrated to give compound 19 (1.69 kg) as a solid in 79% yield. (Route 3)

Alternatively, Compound 19b can be prepared according to Example 1-4a.

Example 1-4a: Methyl Δ$^{11,12}$-3α-(ethoxycarbonyl) oxy-6α-ethyl-5β-cholan-24-oate (19b)

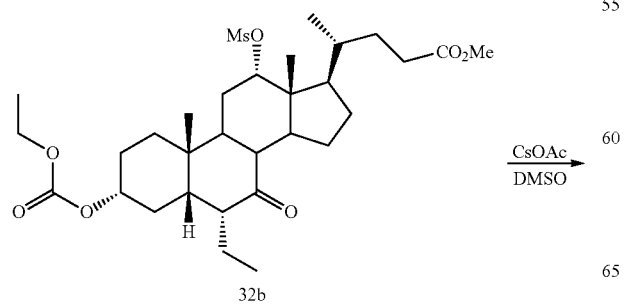

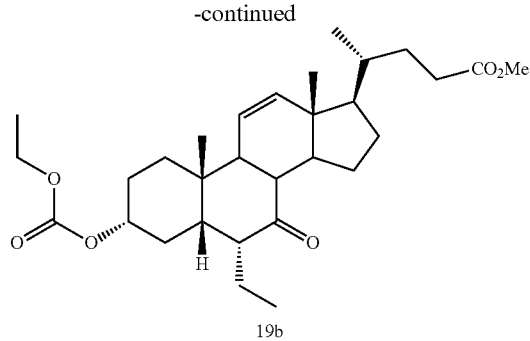

To a solution of methyl 3α-(ethoxycarbonyl)oxy-12α-(methansulfonyl)oxy-6α-ethyl-7-oxo-5β-cholan-24-oate (32b) (14.4 g, 25.3 mmol) in DMSO (150 mL) was added CsOAc (19.6 g, 102 mmol). The mixture was stirred at 90-100° C. for 18 hours before it was cooled to room temperature. The mixture was added to water (500 mL) and the resulting precipitate was filtered, washed with water and dried on the funnel. A 5.9 g portion of crude compound 19b was dissolved in MeOH (5.9 mL) at reflux. Water (3 mL) was added and the mixture was cooled to 25-35° C. and product precipitated. Additional water (56 mL) was added at 20-25° C., the suspension was stirred for 1.5 h then vacuum filtered and washed with water and dried under vacuum. Compound 19b (5.64 g) was isolated in 88.7% yield (from compound 32b). $^1$H-NMR (300 MHz, CDCl$_3$): δ 0.75 (s, 3H, 18-CH$_3$), 0.82 (t, J=7.3 Hz, 3H, 26-CH$_3$), 1.00 (d, J=6.3 Hz, 3H, 21-CH$_3$), 1.17 (s, 3H, 19-CH$_3$), 1.29 (t, J=7.3 Hz, 3H OC(O)OCH$_2$C$\underline{H}$$_3$), 3.66 (s, 3H, CO$_2$CH$_3$), 4.15 (q, 2H, OC(O)OC$\underline{H}$$_2$CH$_3$), 4.38-4.64 (m, 1H, 3-CH), 5.33 (d, J=10.3 Hz, 1H, 12-CH), 6.18 (dd, J$_1$=2.3 Hz, J$_2$=10.3 Hz, 1H, 11-CH).(Route 4)

Example 1-4b: Methyl Δ$^{11,12}$-3α-(ethoxycarbonyl) oxy-6α-ethyl-5β-cholan-24-oate (19b)

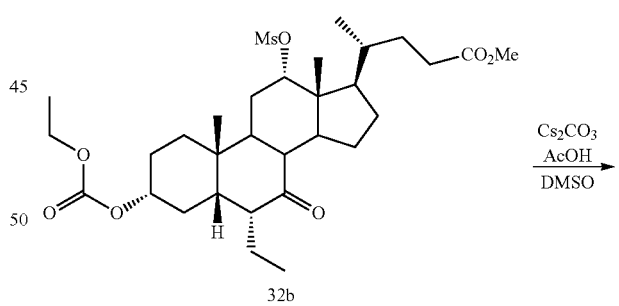

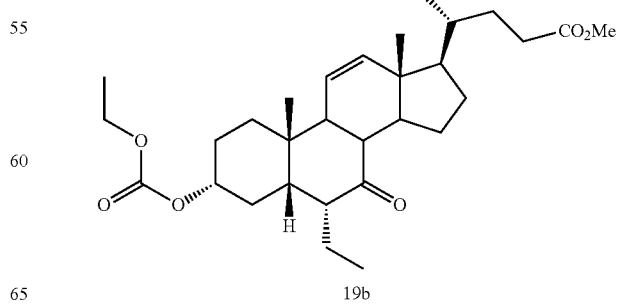

Cs₂CO₃ (278.6 g, 855.1 mmol) and AcOH (41.08 g, 39.1 mL, 684.0 mmol) were mixed in DMSO (1 L) and stirred for 30 min at 50-70° C. Methyl 3α-(ethoxycarbonyl)oxy-12α-(methansulfonyl)oxy-6α-ethyl-7-oxo-5β-cholan-24-oate (32b) (102.4 g, 171.0 mmol) was added and the mixture was stirred at 90° C. for 18 hours. The mixture was cooled to ambient temperature and then was added slowly to 4 L of pre-cooled water (0-5° C.) containing 200 mL of concentrated HCl. The off-white precipitate was filtered, washed with water (3×1 L) and dried on a vacuum filter. The solids were taken up in heptanes (2 L) and heated. The remaining water was removed and the solution containing insoluble brown tar was filtered over a layer of Celite. The resulting filtrate was concentrated affording compound 19b (84.9 g, 98.8%) as light-brown solid.

Example 1-5: Methyl 3α-Acetoxy-12-bromo-6α-ethyl-7-keto-11-hydroxy-5β-cholan-24-oate (21)

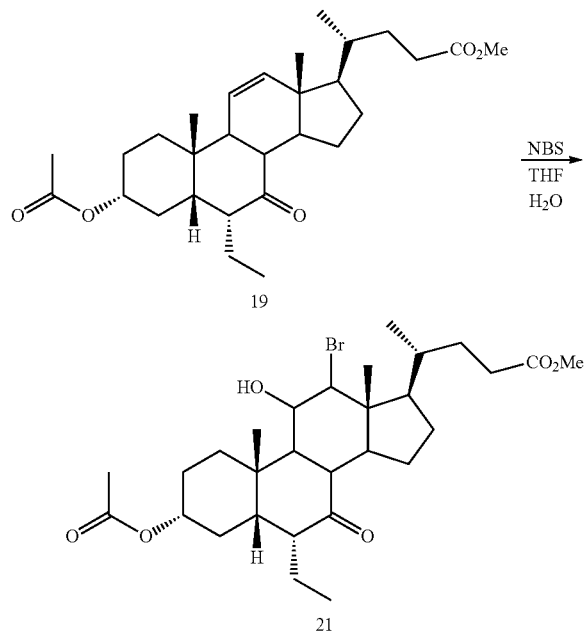

To a solution of compound 19 (53.5 g, 113 mmol) in MeCN (455 mL) and H₂O (116 mL) was added NBS (24.13 g, 135 mmol) at about −5° C. to about 5° C. in portions over 25 min. After complete addition, the mixture was stirred at room temperature. After 1.5 h the mixture was poured in 2.5% aq. NaHSO₃ (1.5 L) and stirred at room temperature. The mixture was extracted with EtOAc:heptanes 10:1 (500 mL and 200 mL). The combined organic layer was washed with 5% aq. NaHSO₃ (200 mL), 10% aq. NaHCO₃ (400 mL), brine (200 mL), dried over Na₂SO₄, filtered and concentrated to give compound 21 (62 g) as a yellowish foam. This material was used without purification in the next reaction step. ES-API Pos: 586.6 [M+H₂O]. ¹H-NMR (400 MHz, CDCl₃): δ 0.82 (s, 3H, 26-CH₃), 1.03-1.07 (m, 6H, 18-CH₃, 21-CH₃), 1.44 (s, 3H, 19-CH₃), 2.01 (s, 3H, OCOCH₃), 3.68 (s, 3H, CO₂CH₃), 4.37 (s, 1H, CH-11), 4.44 (s, 1H, CH-12), 4.63-4.69 (m, 1H, CH-3).

Alternatively, to a water bath cooled solution of compound 19 (1.5 g, 3.17 mmol) in THF (11 mL) and H₂O (4 mL) was added NBS (677 mg, 3.8 mmol) in portions over 5 min. at 20° C. At the end of the addition the color remained slightly orange. After complete addition, the mixture was stirred at room temperature. After 18 h the mixture was poured in 2.5% aq. NaHSO₃ (20 mL) and stirred at room temperature. To the mixture brine (10 mL) was added and the mixture was extracted with EtOAc:heptanes 10:1 (40 mL and 20 mL). The combined organic layer was washed with 10% aq. NaHCO₃ (15 mL), brine (20 mL) dried over Na2SO4, filtered and concentrated to give compound 21 (1.86 g) as a yellowish foam containing some EtOAc. This material was used without purification in the next reaction step.

Alternatively, compound 21 can be prepared according to the following procedure:

Dibromamine-T (TsNBr₂): To a solution of Chloramine-T (10 g, 40.7 mmol) in water 200 mL was added bromine (2 mL, 6.24 g, 78 mmol) in a dropwise fashion. After addition was completed, the mixture was stirred for 2 h. The mixture was filtered and the filtrate was washed with water (2×20 mL) and dried under vacuum to provide 12 g (90% yield) of dibromamine-T.

To a solution of compound 19 (416 mg, 1 mmol) in MeCN (4 mL) and H₂O (1 mL) was added dibromamine-T (329 mg, 1 mmol) in portions. After the addition was completed, the mixture was stirred at room temperature for about 5 to about 30 min. The mixture was quenched with sodium thiosulfate (284 mg, 1.8 mmol), diluted with water (20 mL) and extracted with EtOAc. The organic layer was washed with 10% NaHCO₃, dried over Na₂SO₄ filtered and concentrated to produce crude compound 21.

Alternatively, iodination of compound 19 using an iodination agent such as N-iodosuccinimide in the presence of TFA, followed by selective de-trifluoroacetylation of intermediate 21c can generate the halohydrin (iodohydrin) 21a. The procedure is shown in Example 1-5a.

Example 1-5a: Methyl 3α-Acetoxy-6α-ethyl-12-iodo-7-keto-11β-trifluoroacetoxy-5β-cholan-24-oate (21a)

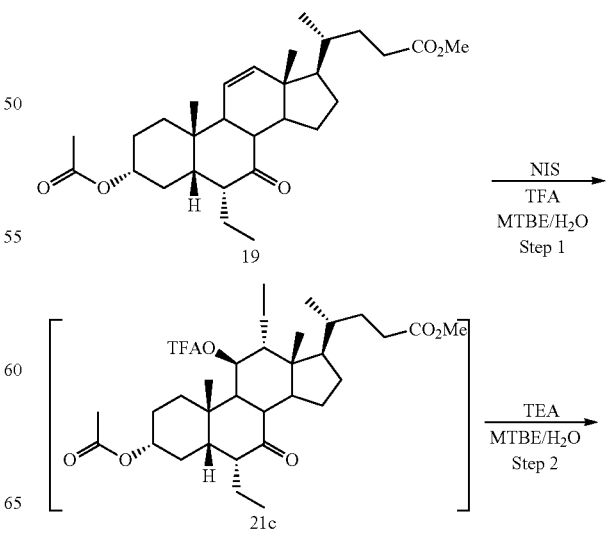

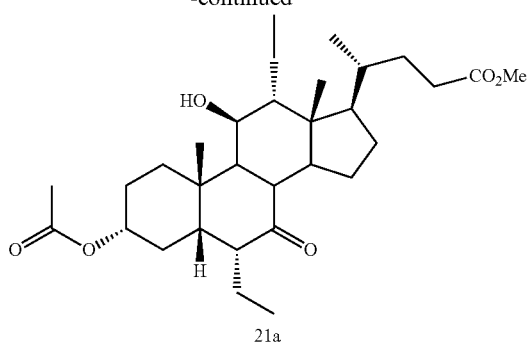

21a

To a mixture of compound 19 (10.0 g, 21.16 mmol), N-iodosuccinimide (6.66 g, 29.62 mmol), MTBE (100 mL) and water (6.47 mL) at 5-15° C. was charged trifluoroacetic acid (8.1 mL, 105.8 mmol). The mixture was warmed to 20-25° C. and stirred until reaction completion (within 7 h). A solution of 0.5M sodium bisulfite (50 mL) was added and the organic layer was separated and washed with saturated aqueous NaHCO$_3$. To the MTBE solution containing compound 21c was added water (1 mL) and triethylamine (4.42 mL, 31.74 mmol) and stirred at 20-25° C. until reaction completion (within 74 h). The pH was adjusted with acetic acid as needed until pH 5-7 was reached. The organic layer was washed with water (2×30.0 mL) then concentrated under vacuum to generate iodohydrin 21a (12.7 g, 20.60 mmol) as an off-white solid in 97.3% yield.

Alternatively, iodination of compound 19b using an iodination agent such as NIS in the presence of H$_5$IO$_6$ can generate the halohydrin 21b in a single step. The procedure is shown in Example 1-5b.

Example 1-5b: Methyl 3α-(ethoxycarbonyl)oxy-6α-ethyl-11β-hydroxy-12-iodo-7-keto-5β-cholan-24-oate (21b)

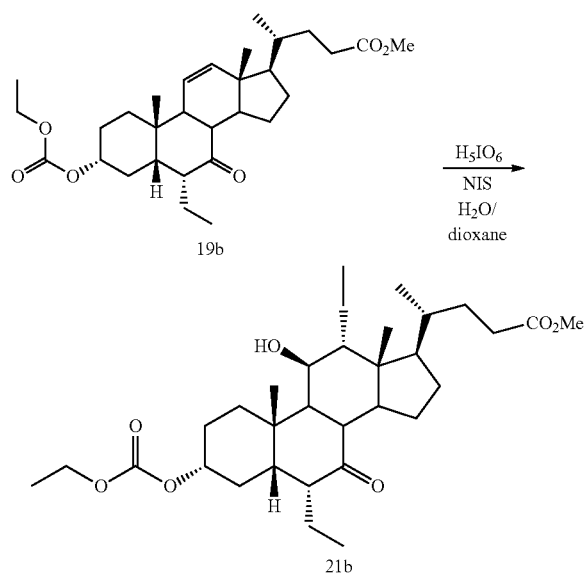

To a stirred mixture of compound 19b (4.1 g, 8.16 mmol), H$_5$IO$_6$ (0.45 g, 1.63 mmol), dioxane (41 mL), and water (10.3 mL) at 0-5° C. was added N-iodosuccinimide (2.75 g, 12.24 mmol). The mixture was stirred at 0-5° C. until reaction completion (within 3 h), then treated with 10 wt % aqueous sodium bisulfite (20.5 mL), diluted with methanol (41 mL), then added to cold water (0-5° C.). The resulting precipitate was filtered and dried under vacuum to give 5.4 g of wet compound 21b which was used directly in the next step (reductive dehalogenation step). $^1$H-NMR (300 MHz, CDCl$_3$): δ 0.82 (t, J=7.3 Hz, 3H, 26-CH$_3$), 1.05 (d, 3H, 21-CH$_3$), 1.10 (s, 3H, 18-CH$_3$), 1.29 (t, J=7.3 Hz, 3H OC(O)OCH$_2$CH$_3$), 1.41 (s, 3H, 19-CH$_3$), 2.01 (s, 3H, OCOCH$_3$), 3.66 (s, 3H, CO$_2$CH$_3$), 4.16 (q, 2H, OC(O)OCH$_2$CH$_3$), 4.39-4.59 (m, 2H, 3-CH, 11-CH), 4.64 (d, J=7.3 Hz, 1H, 12-CH).

Example 1-6: Methyl 3α-Acetoxy-12-bromo-6α-ethyl-7,11-diketo-5β-cholan-24-oate (22)

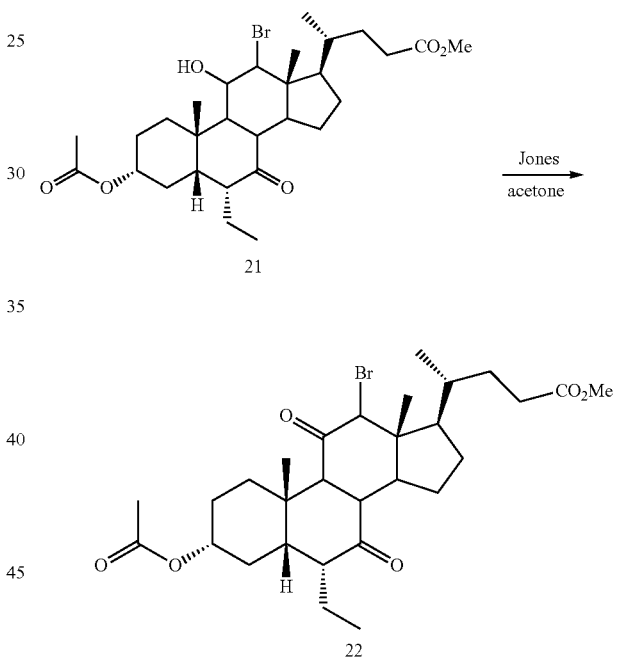

To an ice bath cooled stirred solution of bromohydrin 21 (crude, about 113 mmol) at 6° C. in acetone (1 L) was added dropwise Jones reagent (32 mL) over approximately 15 min. The reaction mixture was stirred for 30 min at 6° C. Isopropanol (45 mL) was added dropwise. After addition the reaction was stirred for 30 min. and filtered through Celite®. The filtrate was concentrated under reduced pressure, taken up in CH$_2$Cl$_2$ (700 mL), washed with water (400 mL), 10% aq. NaHCO$_3$ (100 mL) and dried over Na$_2$SO$_4$ and concentrated under reduced pressure to afford compound 22 (55 g). ES-API Pos: 584.2 [M+H$_2$O]. $^1$H-NMR (200 MHz, CDCl$_3$): δ 0.77-0.85 (m, 6H, 18-CH$_3$, 26-CH$_3$), 0.96 (d, J=6.1 Hz, 3H, 21-CH$_3$), 1.45 (s, 3H, 19-CH$_3$), 2.02 (s, 3H, OCOCH$_3$), 3.68 (s, 3H, CO$_2$CH$_3$), 4.28 (s, 1H, 12-CH), 4.59-4.70 (m, 1H, 3-CH).

Example 1-7: Methyl 3α-Acetoxy-6α-ethyl-7,11-diketo-5β-cholan-24-oate (23a)

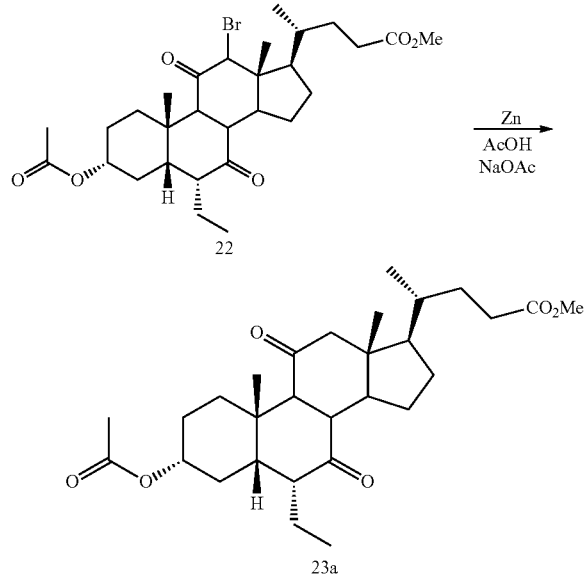

To a stirring solution of compound 22 (crude, about 113 mmol) in AcOH (1.2 L) was added NaOAc (64.5 g, 786 mmol) and Zn (56 g, 850 mmol). The resulting suspension was heated slowly to 78° C. After 5 h a $^1$H-NMR sample revealed full consumption of compound 22. The reaction mixture was allowed cool to room temperature and EtOAc (2.5 L) was added to the reaction mixture and the resulting suspension was filtered. The filtrate was washed with brine (2×500 mL). The organic layer was dried over $Na_2SO_4$ and concentrated under reduced pressure to afford of crude compound 23a. This crude material was suspended in $CH_2Cl_2$ (250 mL), purified by column chromatography ($SiO_2$, 2.5 kg, EtOAc:heptanes 1:4), and analyzed by $^1$H-NMR and LCMS. ES-API Pos: 506.8 [M+$H_2O$]. $^1$H-NMR (400 MHz, $CDCl_3$): δ 0.60 (s, 3H, 18-$CH_3$), 0.77 (t, J=7.3 Hz, 3H, 26-$CH_3$), 0.86 (d, J=5.2 Hz, 3H, 21-$CH_3$), 1.41 (s, 3H, 19-$CH_3$), 1.96 (s, 3H, $OCOCH_3$), 3.64 (s, 3H, $CO_2CH_3$), 4.58-4.63 (m, 1H, 3-CH).

Alternatively, compound 23a can be prepared via a telescoped process, where compound 22 is prepared without isolation of intermediate 21 and compound 23a is prepared without isolation of compound 22. The telescoped procedure is shown below.

Telescopic Procedure: Methyl 3α-Acetoxy-6α-ethyl-7,11-diketo-5β-cholan-24-oate (23a)

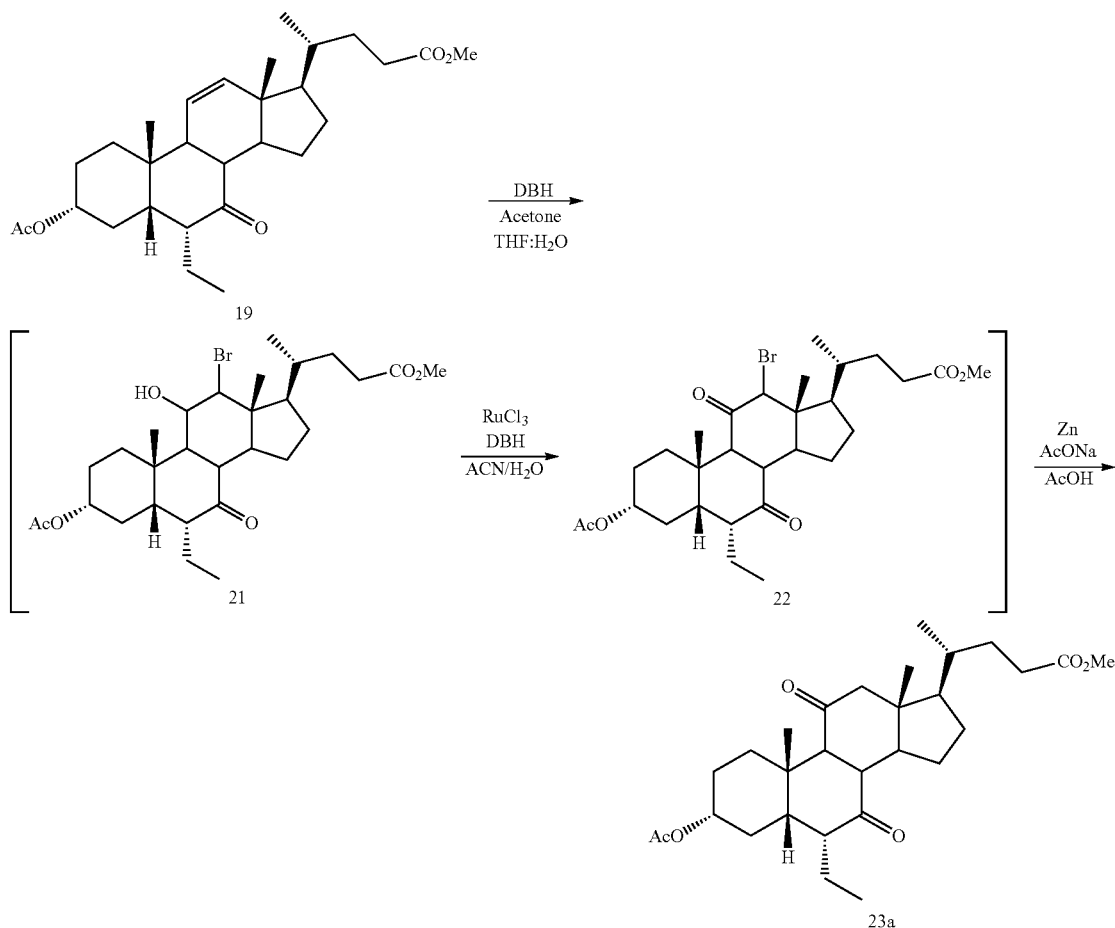

A solution of compound 19 (1.67 kg, 3.53 mol) in acetone (3.3 L), THF (10 L) and water (3.3 L) was sparged with nitrogen and cooled to 0-5° C. Dibromodimethyl hydantoin (DBH) (1.11 kg, 3.88 mol) was added in portions over 0.5 h. The mixture was stirred in the absence of light at 5-15° C. until the reaction was complete (within 12 h). The initial reaction mixture containing compound 21 was added to a stirred, pre-cooled (0-5° C.) mixture of DBH (1.01 kg, 3.53 mol), NaOAc (0.58 kg, 7.06 mol), and RuCl$_3$ (22 g, 0.106 mol) in acetonitrile (4.2 L) and water (4.2 L) over 0.5 h. The mixture was stirred at 4-10° C. until reaction completion (within 4 h). The reaction was quenched with 2.5 wt % NaHSO$_3$ (18 L) and partitioned with EtOAc (18 L). The aqueous layer was back washed with EtOAc and the combined organic layers were washed with 10 wt % Na$_2$SO$_4$ (aq) (2×10 L). The EtOAc solution of compound 22 was concentrated to a final volume of 8.4 L.

To a vessel containing NaOAc (1.16 kg, 14.12 mol) and zinc dust (1.15 kg, 17.65 mol) was added a solution of compound 22 in EtOAc (8.4 L) followed by glacial AcOH (8 L). The mixture was heated to 70-80° C. and agitated until reaction completion (within 4 h). The mixture was cooled to ambient temperature and filtered through Celite®, and the Celite® was washed with EtOAc (3×4 L). The filtrate was washed sequentially with water (10 L), 8% NaHCO$_3$ (aq) (2×10 L) and water (10 L). The organic layer was dried over Na$_2$SO$_4$, concentrated to a residue (1.74 kg) and chromatographed on silica gel (5-10% EtOAc-Heptane). The product-rich fractions were pooled and concentrated to give compound 23a (0.882 kg) in 51.1% yield (from compound 19). Fractions containing compound 19 (a reaction byproduct) were pooled and concentrated to give 0.266 kg of recovered compound 19.

Example 1-8: 3α-hydroxy-7,11-diketo-6α-ethyl-5β-cholan-24-oic acid (40)

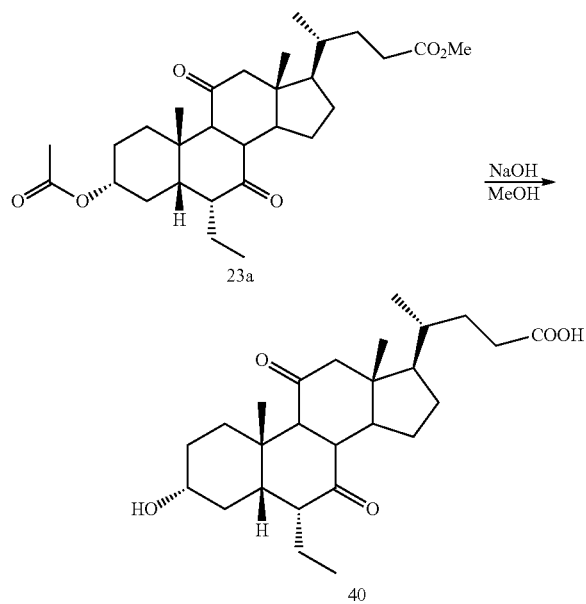

To a stirring solution of compound 23a (9.7 g, 19.8 mmol) in MeOH (170 mL) was added NaOH (9 g, 225 mmol). The resulting solution was heated at 45° C. for 18 h. $^1$H-NMR showed full conversion. The mixture was concentrated to approximately 30 mL. Water (150 mL) was added. The mixture was cooled in an ice bath and 3N aq. HCl was added dropwise to pH<2. The resulting suspension was stirred for an additional 0.5 h. The product was filtered off, washed with water (20 mL) and dried in vacuo to give 9.45 g of compound 40 as beige solid (about 100% yield), which was used without purification in the next reaction step. ES-API Pos: 450.6 [M+H$_2$O]. $^1$H-NMR (400 MHz, CDCl$_3$): δ 0.63 (s, 3H, 18-CH$_3$), 0.81 (t, J=7.2 Hz, 3H, 26-CH$_3$), 0.91 (d, J=5.2 Hz, 3H, 21-CH$_3$), 1.44 (s, 3H, 19-CH$_3$), 3.55-3.59 (m, 1H, 3-CH).

Example 1-9: 3α,7α,11β-Trihydroxy-6α-ethyl-5β-cholan-24-oic acid (100)

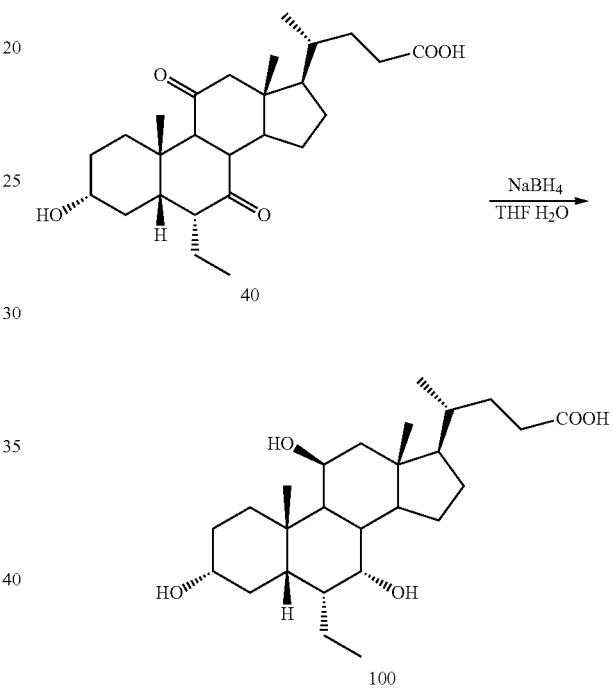

To a stirred ice-bath cooled solution of diketone 40 (about 6.7 g, 15.5 mmol) in a mixture of THF (160 mL) and water (30 mL), NaBH$_4$ (3.48 g, 91 mmol) was added in small portions. The resulting solution was stirred for 18 h at room temperature. $^1$H-NMR revealed full conversion. Brine (40 mL), EtOAc (100 mL) and 2N aq. HCl (to pH<2) were added, the layers were separated. The aqueous layer was extracted again with EtOAc (100 mL). The combined organic extracts were washed with brine (25 mL), dried over Na$_2$SO$_4$ and concentrated under reduced pressure to afford 6.2 g of compound 100. The final product was purified by column chromatography. ES-API Neg: 435.5 [M−H]. $^1$H-NMR (400 MHz, CD$_3$OD): δ 0.89-0.92 (s, 6H, 18-CH$_3$, 26-CH$_3$), 1.00 (d, J=6.35 Hz, 3H, 21-CH$_3$), 1.18 (s, 3H, 19-CH$_3$), 3.31-3.34 (m, 1H, 3-CH), 3.73 (s, 1H, 7-CH), 4.20 (s, 1H, 11-CH). $^{13}$C-NMR (100.6 MHz, CD$_3$OD): δ 10.1, 12.7, 16.8, 21.6, 22.7, 25.7, 27.0, 30.0 (×2), 30.3, 32.8, 34.4, 34.9 (×2), 36.3 (×2), 40.6, 40.8, 46.4, 48.1, 50.2, 55.8, 67.1, 69.4, 71.4, 177.4.

Example 1-10: 3α,7α,11β-Trihydroxy-6α-ethyl-5β-cholan-24-oic acid (100)

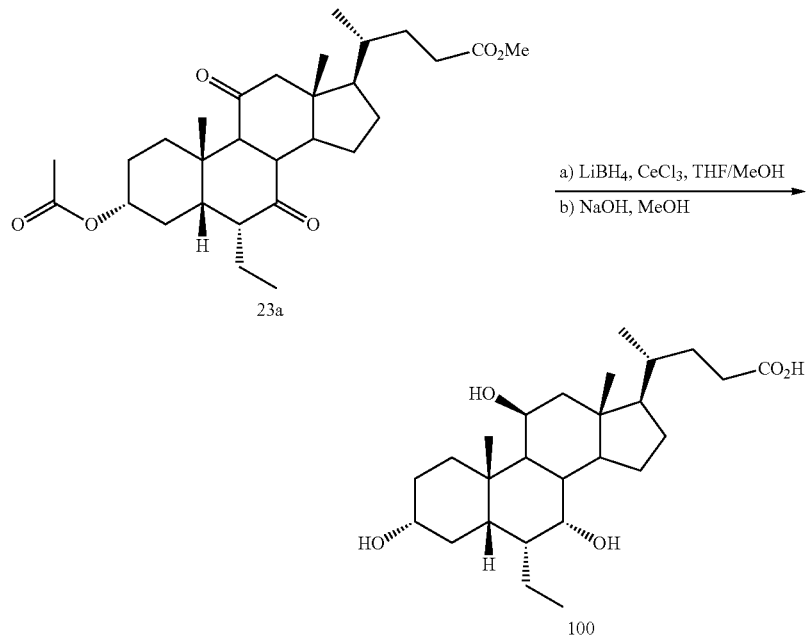

To a solution of compound 23a (442 mg, 0.91 mmol) in THF/MeOH (9 mL, 1:1), CeCl$_3$·7H$_2$O (674 mg, 1.81 mmol) and LiBH$_4$ (69 mg, 3.62 mmol) were sequentially added in one portion at 0° C. The resulting mixture was stirred at 0° C. for 4 h. The mixture was diluted with CH$_2$Cl$_2$ (15 mL) and quenched at 0° C. by adding H$_2$O (15 mL) and 3 N HCl (15 mL). The phases were separated and the aqueous phase was extracted with CH$_2$Cl$_2$ (2×15 mL). The combined organic extracts were washed with H$_2$O (20 mL), brine (20 mL), dried over anhydrous Na$_2$SO$_4$ and concentrated under reduced pressure. The crude (444 mg) was dissolved in MeOH/H$_2$O (4.5 mL, 9:1) and stirred overnight at room temperature in presence of NaOH (360 mg, 9.01 mmol). The mixture was concentrated under reduced pressure and the residue was dissolved in CH$_2$Cl$_2$ (20 mL) and acidified with 3 N HCl. The phases were separated and the aqueous phase was extracted with CH$_2$Cl$_2$ (3×20 mL). The combined organic extracts were washed with H$_2$O (30 mL), brine (30 mL), dried over anhydrous Na$_2$SO$_4$ and concentrated under reduced pressure. The crude was purified by flash chromatography on silica gel affording 272 mg of pure compound 100 (0.62 mmol). ES-API Neg: 435.5 [M−H]. $^1$H-NMR (400 MHz, CD$_3$OD): δ 0.89-0.92 (s, 6H, 18-CH$_3$, 26-CH$_3$), 1.00 (d, J=6.35 Hz, 3H, 21-CH$_3$), 1.18 (s, 3H, 19-CH$_3$), 3.31-3.34 (m, 1H, 3-CH), 3.73 (s, 1H, 7-CH), 4.20 (s, 1H, 11-CH). $^{13}$C-NMR (100.6 MHz, CD$_3$OD): δ 10.1, 12.7, 16.8, 21.6, 22.7, 25.7, 27.0, 30.0 (×2), 30.3, 32.8, 34.4, 34.9 (×2), 36.3 (×2), 40.6, 40.8, 46.4, 48.1, 50.2, 55.8, 67.1, 69.4, 71.4, 177.4.

Telescopic Procedure: 3α,7α,11β-Trihydroxy-6α-ethyl-5β-cholan-24-oic acid (100)

To a solution of methyl 3α-acetoxy-7-keto-Δ$^{11,12}$-6α-ethyl-5β-cholan-24 oate (19) (1.1 g, 2.4 mmol) in THF/H$_2$O (24 mL, 4:1), freshly crystallized N-iodosuccinimide (807 mg, 3.59 mmol) and Jones reagent (2.4 mL) were sequentially added at room temperature and the resulting mixture was refluxed for 1 h. The mixture was allowed to cool to room temperature and then quenched by adding MeOH (25 mL) and 5% w/v aqueous solution of Na$_2$S$_2$O$_3$ (25 mL). The mixture was diluted with EtOAc and filtered on a pad of Celite. The organic phase was washed with aqueous saturated solution of NaHCO$_3$, H$_2$O, brine, dried over anhydrous Na$_2$SO$_4$ and concentrated under reduced pressure. The crude (1.39 g, 95% recovery) was dissolved in AcOH (24 mL) and refluxed for 1.5 h in presence of NaOAc (1.18 g, 14.3 mmol) and Zn dust (1.17 g, 17.9 mmol). The suspension was allowed to cool to room temperature and filtered on a short pad of Celite. The mixture was diluted with EtOAc and washed with H$_2$O, aqueous saturated solution of NaHCO$_3$, H$_2$O, brine, dried over anhydrous Na$_2$SO$_4$ and concentrated under reduced pressure affording the crude diketo intermediate 23a (1.07 g, 92% recovery) as pale yellow solid. To a solution of methyl 3α-acetoxy-7,11-diketo-6α-ethyl-5β-cholan-24 oate (23a) (442 mg, 0.91 mmol) in anhydrous THF/MeOH (9 mL, 1:1), CeCl$_3$·7H$_2$O (674 mg, 1.81 mmol) and LiBH$_4$ (69 mg, 3.62 mmol) were sequentially added in one portion at 0° C. and the resulting mixture was stirred at 0° C. for 4 h. The mixture was diluted with CH$_2$Cl$_2$ and quenched at 0° C. by adding H$_2$O and 3 N HCl. The phases were separated and the aqueous phase was extracted with CH$_2$Cl$_2$. The combined organic extracts were washed with H$_2$O, brine, dried over anhydrous Na$_2$SO$_4$ and concentrated under reduced pressure. The crude (444 mg) was dissolved in MeOH/H$_2$O (4.5 mL, 9:1) and stirred overnight at room temperature in presence of NaOH (360 mg). The mixture was concentrated under reduced pressure and the residue was dissolved in CH$_2$Cl$_2$ and acidified with 3 N HCl (pH=2). The phases were separated and the aqueous phase was extracted with CH$_2$Cl$_2$. The combined organic extracts were washed with H$_2$O, brine, dried over anhydrous Na$_2$SO$_4$ and concentrated under reduced pressure. The crude was purified by flash chromatography on silica gel, affording 280 mg of compound 100.

Alternate Procedure:

A solution of compound 40 (0.736 kg, 1.70 mol) in water (6.94 L) containing 50 wt % NaOH (0.734 kg, 9.18 mol) was heated to 74-80° C. A solution of NaBH$_4$ (0.135 kg, 3.57 mol) in water (0.37 L) containing 50 wt % NaOH (68 g, 0.85 mol) was added and the mixture was stirred until reaction completion (within 21 h). The mixture was cooled and MTBE (7.3 L) was charged, followed by addition of 3N HCl (aq) (ca. 4.4 L) until pH 2 was reached. The aqueous layer was discarded and the organic layer was washed with water (5.4 L), then dried over Na$_2$SO$_4$ and concentrated to 1.2 L. The product solution was diluted with heptane (0.25 L) and chromatographed on silica gel (75-80% MTBE-Heptane). The product-rich fractions were concentrated to a solid and dissolved in water (5 L) containing 50 wt % NaOH (0.242 kg). The solution was concentrated under vacuum to remove ca. 2.2 L of distillates. The mixture was acidified to pH 2 with 2N HCl (1.55 L) and the suspension was further diluted with water (3 L). The suspension was heated to 40° C. for 1 h, cooled to 20-25° C. and vacuum filtered, washed with water (4×2 L) then dried under vacuum. Compound 100 (0.652 kg) was obtained in 88% yield.

A synthesis analogous to one shown in Exemplary Route 4 can proceed through intermediate 47a, which can be prepared by reductive dehalogenation of compound of formula 21a under mild hydrogenation conditions in the presence of catalytic palladium and a base as shown in Example 1-10.

Example 1-10: Methyl 3α-Acetoxy-6α-ethyl-11β-hydroxy-7-keto-5β-cholan-24-oate (47a)

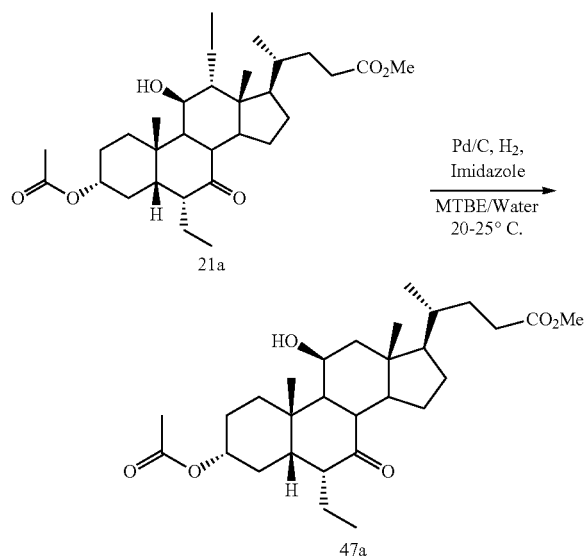

A mixture of compound 21a (100 mg, 0.16 mmol), Pd/C (12 mg), imidazole (54.5 mg, 0.80 mmol), MTBE (1.5 mL) and water (1 mL) was stirred under hydrogen atmosphere (1 atm) at 20-25° C. The mixture was stirred at 20-25° C. until reaction completion. The mixture was filtered through Celite® and Celite® was washed with MTBE (2 mL). The organic layer was separated and washed with water (2×1 mL), then concentrated to generate compound 47a (67 mg) in 78.5% yield.

Alternatively, as shown in Route 4, reductive dehalogenation of compound of formula 21b under mild hydrogenation conditions in the presence of catalytic palladium and a base can produce compound 47b as shown in Example 1-10a.

Example 1-10a: Methyl 3α-(ethoxycarbonyl)oxy-6α-ethyl-11β-hydroxy-7-keto-5β-cholan-24-oate (47b)

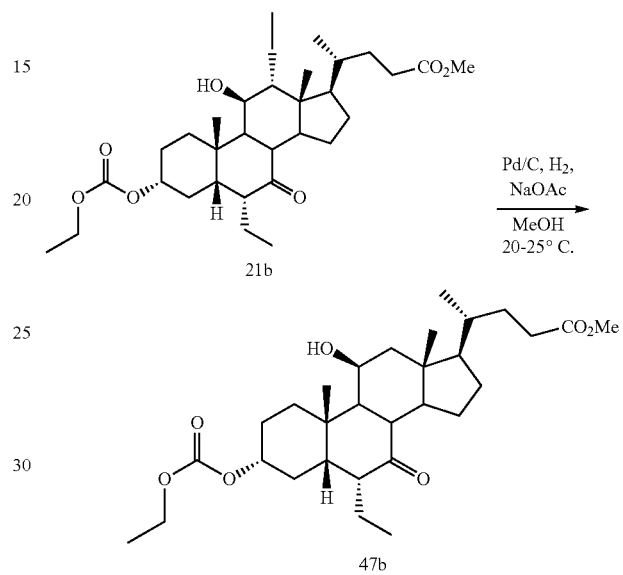

A mixture of compound 21b (5.4 g, wet weight), NaOAc (3.35 g, 40.8 mmol), Pd/C (0.41 g) in MeOH (82 mL) was stirred under a hydrogen atmosphere (0.5 to 2 bar) at 20-25° C. until reaction completion (within 18 h). The mixture was filtered over Celite® and the filtrate was added to a cold solution (0-5° C.) of 0.2 wt % sodium bisulfite (aq). The resulting solids were filtered, washed with water and dried under vacuum to give compound 47b (3.6 g) as a solid in 84.8% yield (2-step yield from compound 19b). $^1$H-NMR (300 MHz, CDCl$_3$): δ 0.81 (t, J=7.3 Hz, 3H, 26-CH$_3$), 0.88 (s, 3H, 18-CH$_3$), 0.91 (d, 3H, 21-CH$_3$), 1.28 (t, J=7.3 Hz, 3H OC(O)OCH$_2$C$\underline{H}_3$), 1.46 (s, 3H, 19-CH$_3$), 3.66 (s, 3H, CO$_2$CH$_3$), 4.00-4.24 (m, 3H, OC(O)OC$\underline{H}_2$CH$_3$, 11-CH), 4.39-4.69 (m, 1H, 3-CH).

Example 1-11: Methyl 3α-(ethoxycarbonyl)oxy-6α-ethyl-7α,11β-dihydroxy-5β-cholan-24-oate (49b)

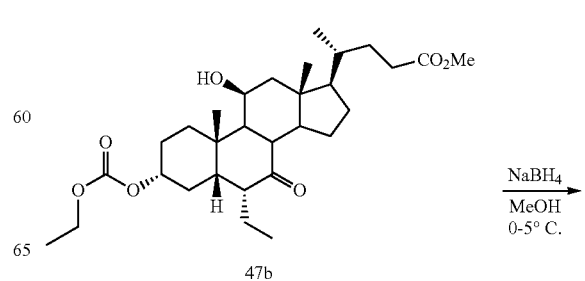

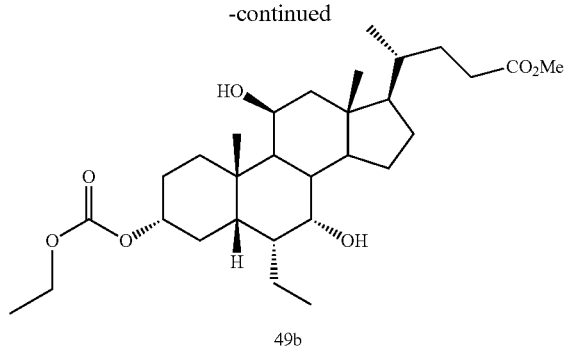

49b

A solution of compound 47b (3.6 g, 6.91 mmol) in methanol (72 mL) was cooled to 0-5° C. with stirring. To the cold solution was added NaBH4 (0.522 g, 13.82 mmol) in portions and continued to stir at 0-5° C. until reaction completion (within 1.5 h). The reaction was quenched with 1N HCl and the resulting precipitate was filtered, washed with water, and dried under vacuum to generate compound 49b (3.26 g) as a solid in 90% yield. $^1$H-NMR (300 MHz, CDCl$_3$): δ 0.80-1.00 (m, 6H, 26-CH$_3$, 21-CH$_3$), 0.91 (d, 3H, 21-CH$_3$), 1.15 (s, 3H, 18-CH$_3$), 1.29 (t, J=7.3 Hz, 3H OC(O)OCH$_2$C$\underline{H}_3$), 1.54 (s, 3H, 19-CH$_3$), 3.66 (s, 3H, CO$_2$CH$_3$), 4.18 (q, 3H, OC(O)OC$\underline{H}_2$CH$_3$), 4.23 (br. s, 1H, 11-CH) 4.30-4.55 (m, 1H, 3-CH).

Example 1-12: 3α,7α,11β-Trihydroxy-6α-ethyl-5β-cholan-24-oic acid (100)

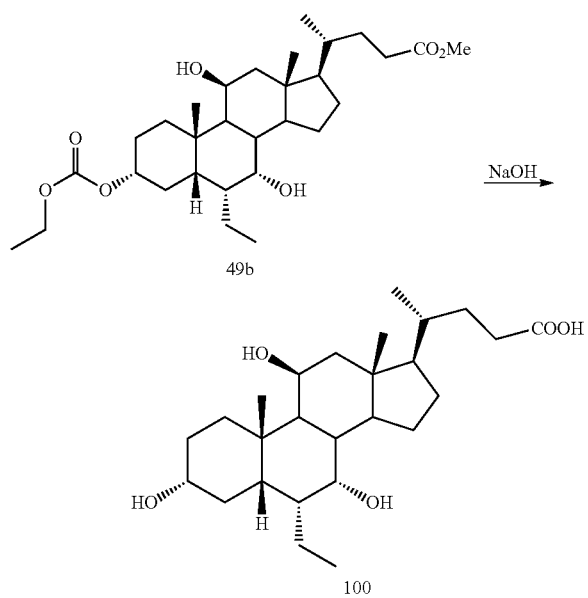 [SMILES: CCOC(=O)O[C@@H]1CC[C@]2(C)C3C(C4CC[C@H]([C@H](C)CCC(=O)OC)[C@@]4(C)C[C@@H]3O)[C@H](O)[C@H](CC)[C@@H]2C1 ; "NaOH" ; CC[C@H]1[C@@H](O)C2C3CC[C@H]([C@H](C)CCC(=O)O)[C@@]3(C)C[C@H](O)C2[C@@]2(C)CC[C@@H](O)C[C@@H]12]

To a solution of compound 49b (1.5 g, 2.8 mmol) in methanol (15 mL) at ambient temperature with stirring was added LiOH (0.20 g, 8.4 mmol). The mixture was warmed to 30-35° C. and was stirred until reaction completion (within 36 h). Water (20 mL) was added and the mixture was concentrated under vacuum. The residue was diluted with water (20 mL) and MTBE (40 mL), then acidified with 1N HCl (aq) to pH 1-2. The solids were vacuum filtered and washed with water, then dried under vacuum to generate compound 100 (1.1 g, 2.5 mmol) in 91% yield.

Example 2-1: 3α,7α-dihydroxy-6α-ethyl-12β-methyl-13-nor-5β-cholan-24-oic acid (45)

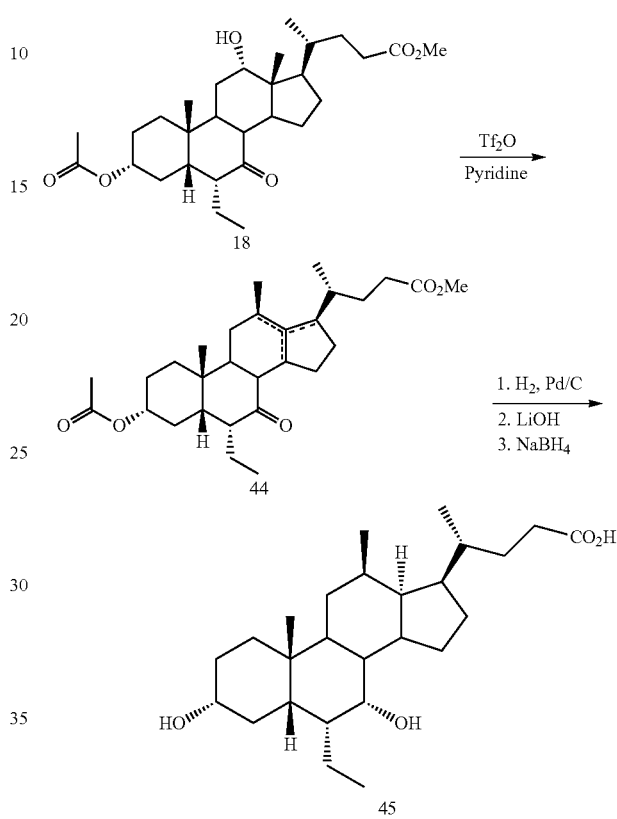

To a solution of compound 18 (49 mg, 0.1 mmol) in anhydrous DCM (0.5 mL) and pyridine (2.4 eq) at −15~−10° C. was added Tf$_2$O (1.1 eq). The reaction was gradually warmed to 0-5° C. and stirred for 2 h, then gradually warmed to room temperature and stirred an additional 15 h. The reaction was diluted with ethyl acetate, and washed with 1N HCl (aq), aqueous NaHCO$_3$, and saturated aqueous NaCl. The organic layer was dried over Na$_2$SO$_4$, concentrated and chromatographed on silica gel (10% ethyl acetate in heptanes) to yield 40 mg of compound 44 as a mixture of regioisomers (85% yield). ES-API Pos: 473.2 [M+1]; 413.2 [M-OAc]. $^1$H-NMR (300 MHz, CDCl$_3$): δ 0.84 (t, 3H, 26-CH$_3$), 0.98 (d, 3H, 21-CH$_3$), 1.14 (s, 3H, 19-CH$_3$), 1.59 (s, 3H, 18-CH$_3$), 2.00 (s, 3H, —OCOCH$_3$), 3.66 (s, 3H, CO$_2$CH$_3$), 4.63-4.67 (m, 1H, 3-CH).

The product (compound 44) is dissolved in methanol and 5% Palladium on carbon is added. The mixture is stirred in the presence of hydrogen pressure until hydrogenation is complete. The product mixture is filtered and treated with excess LiOH until the reaction was complete. The mixture was quenched with HCl (aq) and the product was extracted with DCM, washed with water, dried over Na$_2$SO$_4$ and concentrated to dryness. The product from the previous step was dissolved in aqueous NaOH, and contacted with NaBH$_4$ and stirred until the reaction is complete. The reaction is quenched with HCl (aq) and extracted into ethyl acetate, washed with water and dried over Na$_2$SO$_4$. The ethyl acetate solution was concentrated to dryness to generate 20 mg of Compound 45. ES-API Pos: 492.2 [M+H$_2$O]. $^1$H-NMR (300 MHz, CDCl$_3$): δ 0.75-0.90 (m, 6H, C18-CH3/26-CH$_3$), 0.93 (d, 3H, 21-CH$_3$), 1.14 (s, 3H, 19-CH$_3$), 1.98 (s, 3H, —OCOCH$_3$), 3.64 (s, 3H, CO$_2$CH$_3$), 4.55-4.69 (m, 1H, 3-CH).

The invention claimed is:

1. A method of preparing a compound of formula I

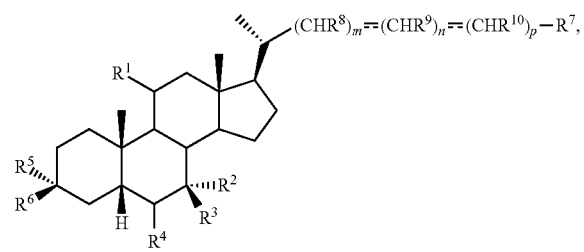

I or a pharmaceutically acceptable salt, hydrate, solvate, or amino acid, sulfate or glucuronide conjugate, or prodrug thereof, wherein:

R$_1$ is OH, alkoxy, or oxo;

R$^2$ is OH, OSO$_3$H, OCOCH$_3$, OPO$_3$H$_2$, halogen, or alkyl optionally substituted with one or more halogen;

R$^3$ is H; or R$^2$ and R$^3$ taken together with the carbon atom to which they are attached form a carbonyl;

R$^5$ is OH, OR$^{11}$, OSO$_3$H, OCOCH$_3$, OPO$_3$H$_2$, halogen, or alkyl optionally substituted with one or more halogen;

R$^6$ is H; or R$^5$ and R$^6$ taken together with the carbon atom to which they are attached form a carbonyl;

R$^4$ is alkyl optionally substituted with one or more halogen or OH, alkenyl, or alkynyl;

R$^7$ is OH, OSO$_3$H, SO$_3$H, OSO$_2$NH$_2$, SO$_2$NH$_2$, OPO$_3$H$_2$, PO$_3$H$_2$, CO$_2$H, C(O)NHOH, NH(CH$_2$)$_2$SO$_3$H, NHCH$_2$CO$_2$H or optionally substituted tetrazolyl, oxadiazolyl, thiadiazolyl, 5-oxo-1,2,4-oxadiazolyl, 5-oxo-1,2,4-thiadiazolyl, oxazolidine-dionyl, thiazolidine-dionyl, 3-hydroxyisoxazolyl, 3-hydroxyisothiazolyl, pyrimidine, 3,5-difluoro-4-hydroxyphenyl, or 2,4-difluoro-3-hydroxyphenyl;

R$^8$, R$^9$, and R$^{10}$ are each independently H, OH, halogen, or alkyl optionally substituted with one or more halogen or OH, or R$^8$ and R$^9$ taken together with the carbon atoms to which they are attached form a 3- to 6-membered carbocyclic or heterocyclic ring comprising 1 or 2 heteroatoms selected from N, O, and S, or R$^9$ and R$^{10}$ taken together with the carbon atoms to which they are attached form a 3- to 6-membered carbocyclic or heterocyclic ring comprising 1 or 2 heteroatoms selected from N, O, and S;

m is 0, 1, or 2;

n is 0 or 1; and p is 0 or 1;

the method comprising the step of reacting a compound of formula I-4 with a halogenating reagent to provide a compound of formula I-5a

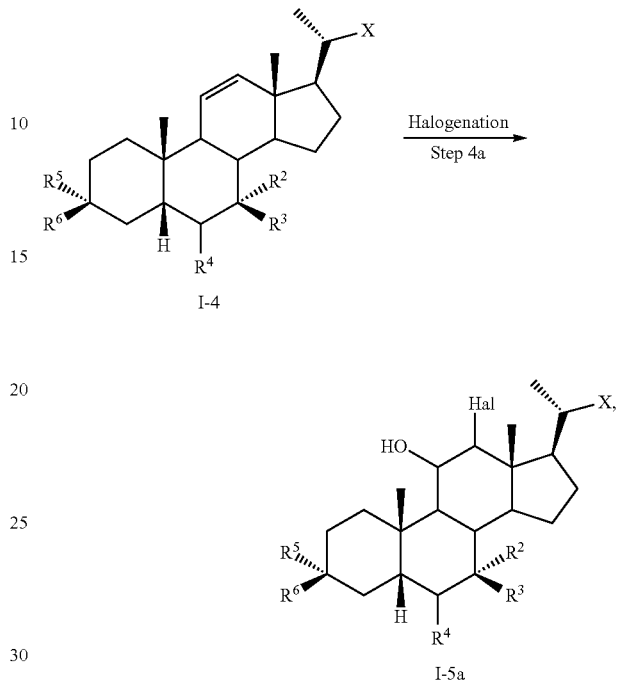

wherein X is —(CHR$^8$)$_m$===(CHR$^9$)$_n$===(CHR$^{10}$)$_p$—R$^7$, and R$^7$, R$^8$, R$^9$, and R$^{10}$ may be protected by R$^{11}$ selected from acetyl, benzoyl, C(O)C$_1$-C$_4$ alkyl, C$_1$-C$_6$ alkoxycarbonyl, optionally substituted aryloxycarbonyl, benzyl, pivaloyl, tetrahydropyranyl ether, tetrahydrofuranyl, 2-methoxyethoxymethyl ether, methoxymethyl ether, ethoxyethyl ether, p-methoxybenzyl ether, methylthiomethyl ether, triphenylmethyl, dimethoxytrityl, methoxytrityl, and silyl ether.

2. The method of claim 1, wherein the compound of formula I is a compound of formula I-9

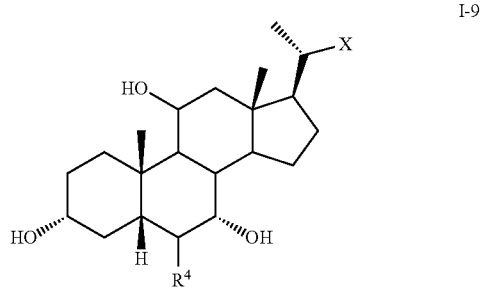

or a pharmaceutically acceptable salt, hydrate, solvate, or amino acid, sulfate or glucuronide conjugate, or prodrug thereof.

3. The method of claim 1, wherein the compound of formula I is a compound of formula II

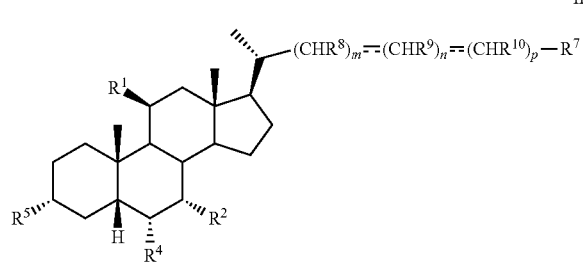

II or a pharmaceutically acceptable salt, hydrate, solvate, or amino acid, sulfate or glucuronide conjugate, or prodrug thereof.

4. The method of claim 1, wherein the compound of formula I is a compound of formula III

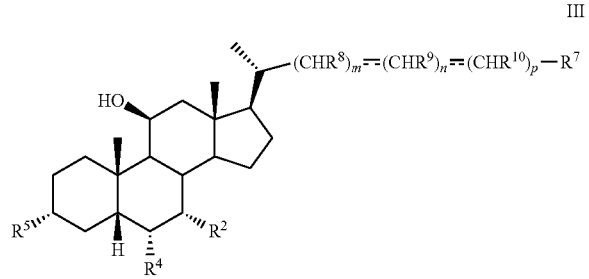

III or a pharmaceutically acceptable salt, hydrate, solvate, or amino acid, sulfate or glucuronide conjugate, or prodrug thereof.

5. The method of claim 1, wherein the compound of formula I is compound 100

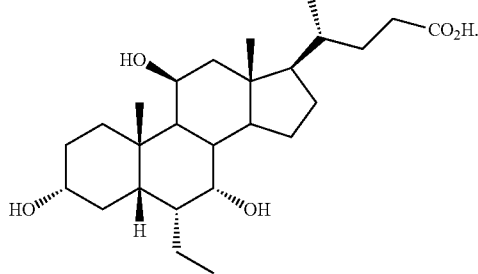

100

6. The method of claim 1, wherein the halogenating agent is a brominating agent.
7. The method of claim 1, wherein the halogenating reagent is an iodinating reagent.
8. The method of claim 1, further comprising converting a compound of formula I-1 into the compound of formula I-4, comprising the steps of 1) protecting the compound of formula I-1 to provide compound of formula I-2;

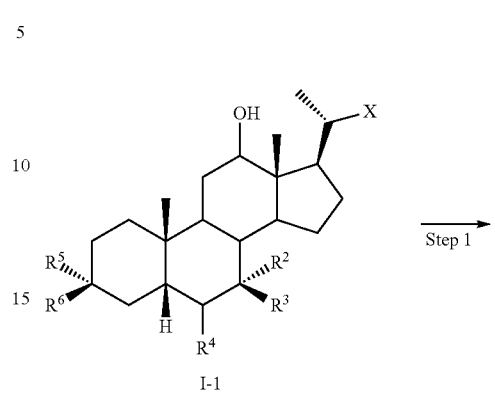

I-1

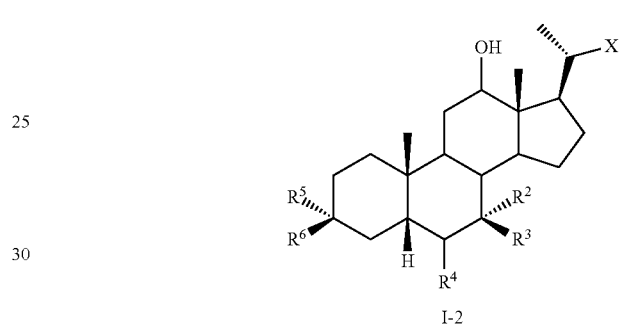

I-2

2) forming a leaving group at C12 to provide a compound of formula I-3; and
3) eliminating the leaving group at C12 to provide the alkene compound of formula I-4

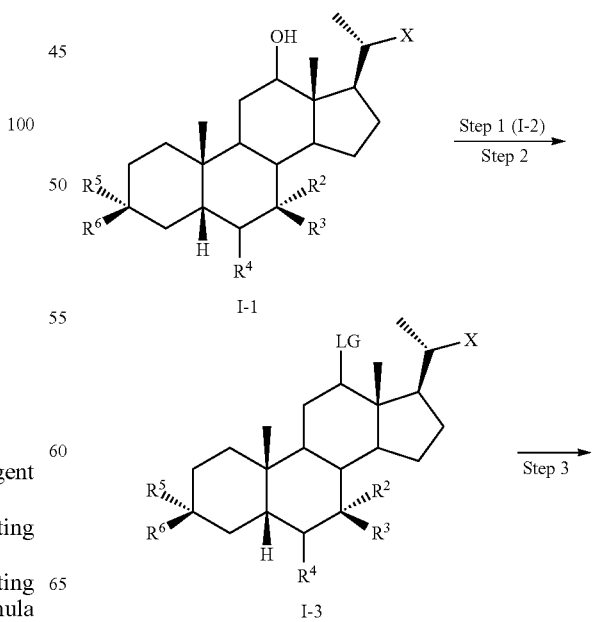

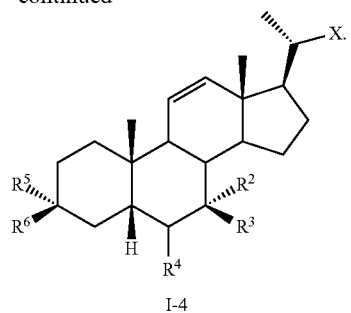

I-4

9. The method of claim 1, further comprising converting the compound of formula I-5a into a compound of formula I-6a, comprising the step of 5) reacting the compound of formula I-5a with an oxidizing agent to prepare the compound of formula I-6a

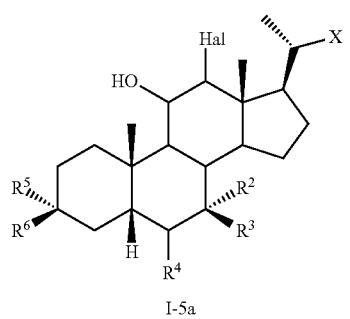

I-5a

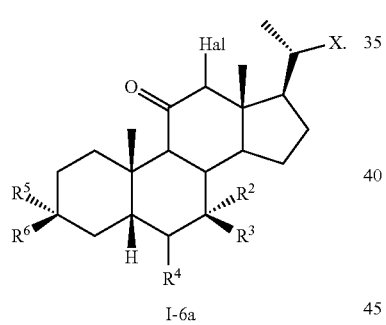

I-6a

10. The method of claim 9, further comprising converting the compound of formula I-6a into a compound of formula I-7, comprising the step of 6) reacting the compound of formula I-6a with a reducing agent to prepare the compound of formula I-7

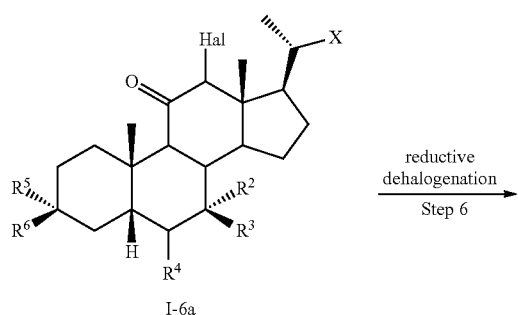

I-6a

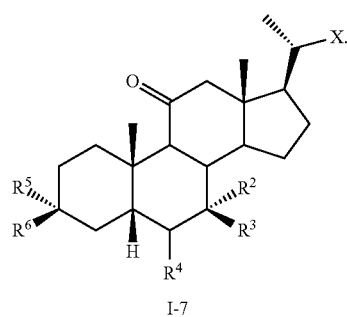

I-7

11. The method of claim 10, further comprising converting the compound of formula I-7 into the compound of formula I, comprising the step of 8) reacting the compound of formula I-7 with a reducing agent to provide the compound of formula I.

12. The method of claim 2, further comprising converting the compound of formula I-5a into the compound of formula I, wherein the compound of formula I-5a is a compound of formula I-5b and the compound of formula I is a compound of formula I-9, comprising the steps of:

1) reacting the compound of formula I-5b with a reducing agent to prepare the compound of formula I-5c

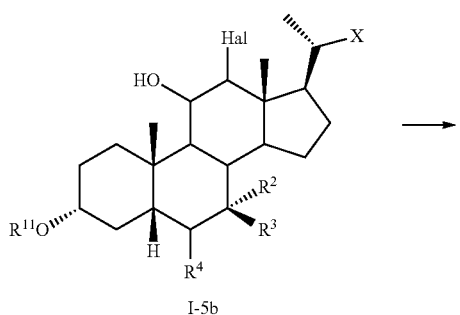

I-5b

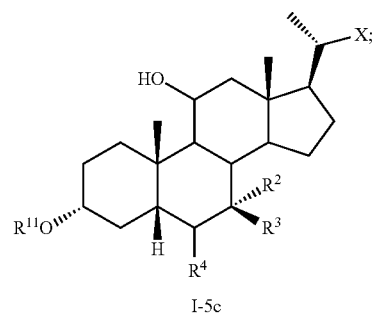

I-5c 2) reacting the compound of formula I-5c with a reducing agent to provide the compound of formula I-5d

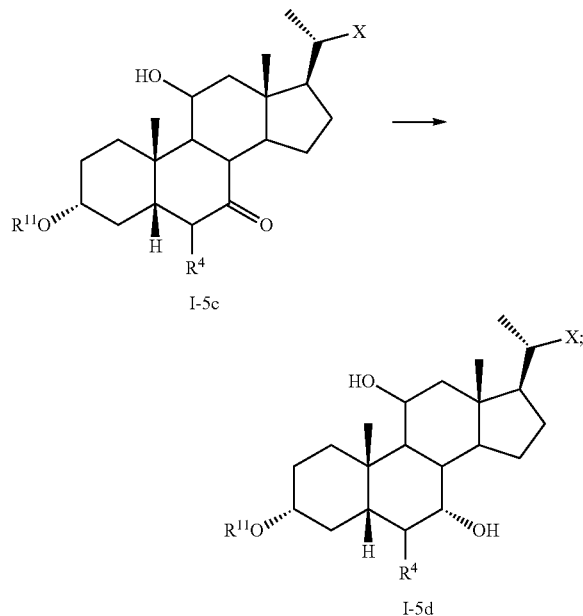

I-5c

I-5d and deprotecting the compound of formula I-5d to provide the compound of formula I-9.

13. The method of claim 10, further comprising converting the compound of formula I-7 into the compound of formula I, wherein the compound of formula I-7 is a compound of formula I-7a and the compound of formula I is a compound of formula I-9, comprising the steps of:

1) reacting the compound of formula I-7a with a reducing agent to provide a compound of formula I-8a; and
2) deprotecting the compound of formula I-8a to obtain the compound of formula I-9

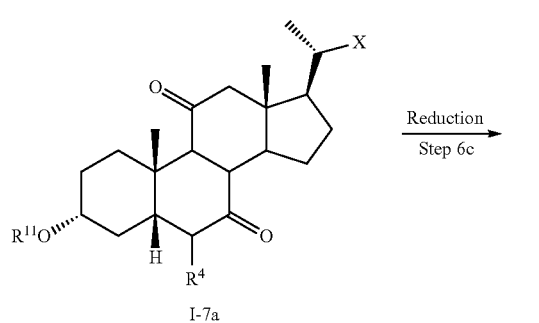

I-7a

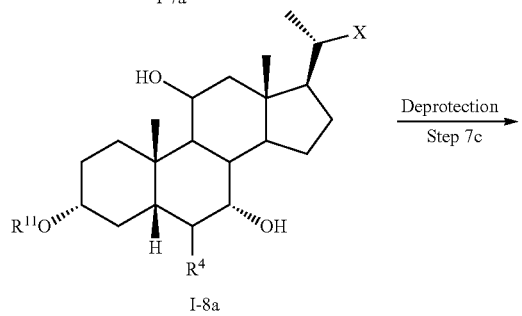

I-8a

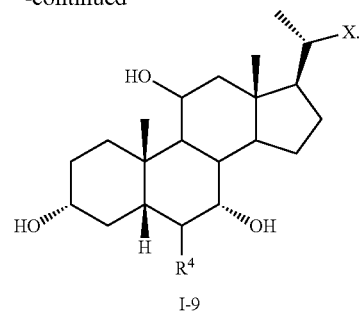

I-9

14. The method of claim 6, wherein the brominating agent is N-bromosuccinimide.

15. The method of claim 7, wherein the iodinating agent is N-iodosuccinimide.

16. The method of claim 9, wherein the oxidizing agent is $RuCl_3$.

17. The method of claim 10, wherein the reducing agent is zinc metal.

18. The method of claim 11, wherein the reducing agent is sodium borohydride.

19. The method of claim 12, wherein the compound of formula I-9 is compound 100

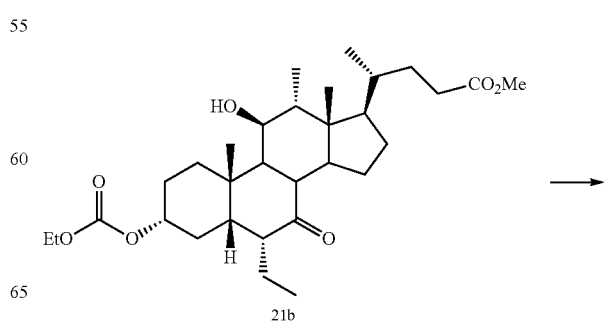

100

20. The method of claim 5, further comprising converting the compound of formula I-5a into the compound of formula I, wherein the compound of formula I-5a is a compound of formula 21b and the compound of formula I is compound 100, comprising the steps of:

1) reacting the compound of formula 21b with a reducing agent to prepare a compound of formula 47b;
2) reacting the compound of formula 47b with a reducing agent to provide a compound of formula 49b; and
3) deprotecting the compound of formula 49b to provide compound 100

21b

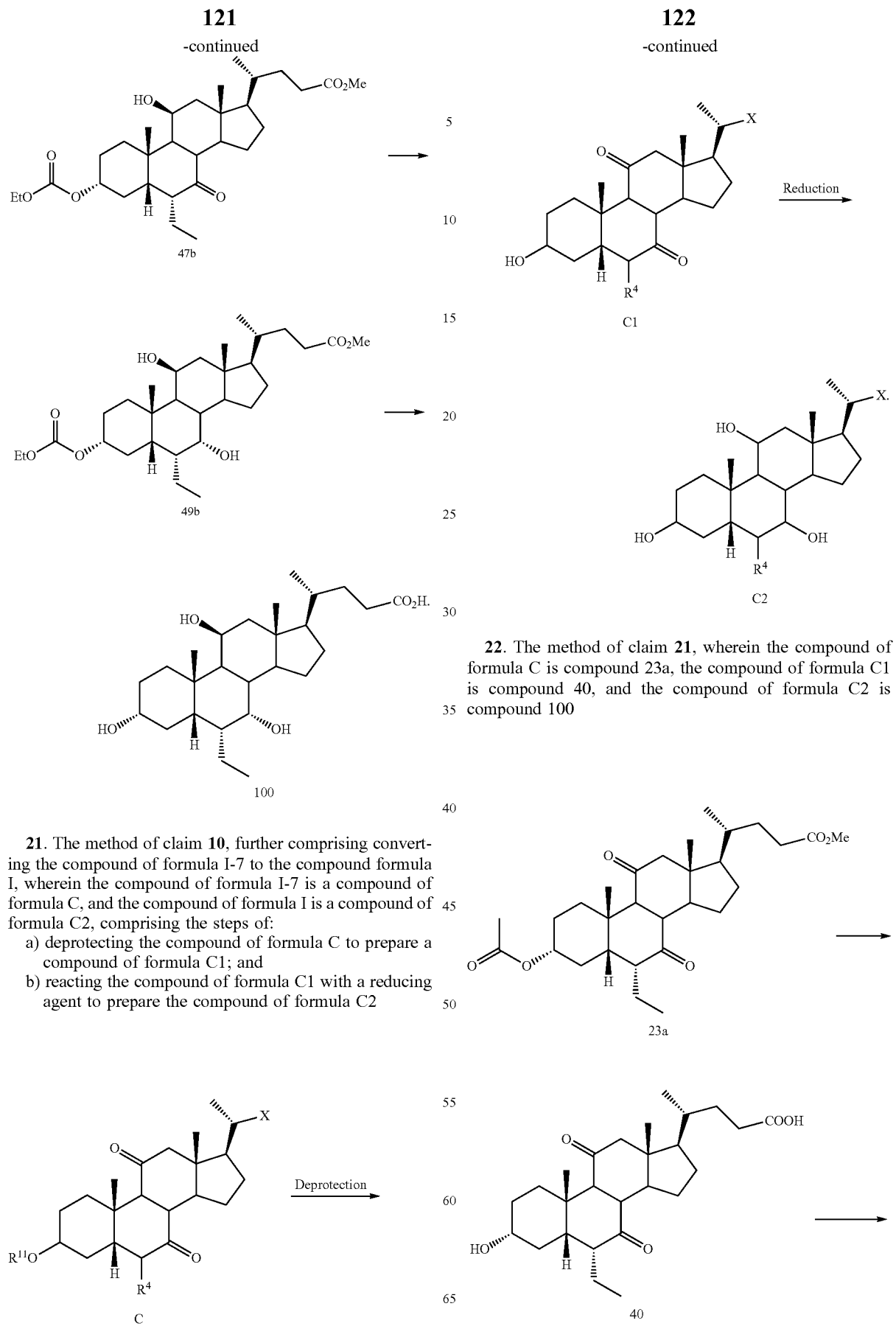

21. The method of claim 10, further comprising converting the compound of formula I-7 to the compound formula I, wherein the compound of formula I-7 is a compound of formula C, and the compound of formula I is a compound of formula C2, comprising the steps of:
 a) deprotecting the compound of formula C to prepare a compound of formula C1; and
 b) reacting the compound of formula C1 with a reducing agent to prepare the compound of formula C2

22. The method of claim 21, wherein the compound of formula C is compound 23a, the compound of formula C1 is compound 40, and the compound of formula C2 is compound 100

-continued
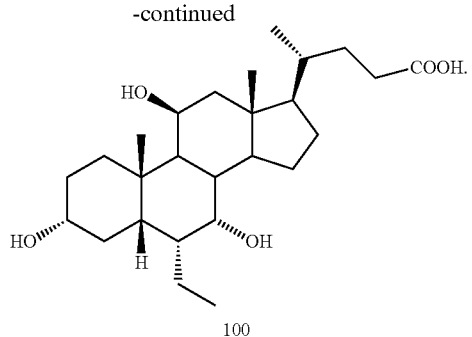
100
* * * * *

UNITED STATES PATENT AND TRADEMARK OFFICE
CERTIFICATE OF CORRECTION

PATENT NO. : 11,066,437 B2
APPLICATION NO. : 16/016486
DATED : July 20, 2021
INVENTOR(S) : Roberto Pellicciari et al.

It is certified that error appears in the above-identified patent and that said Letters Patent is hereby corrected as shown below:

In the Specification

At Column 90, compound structure 21b:

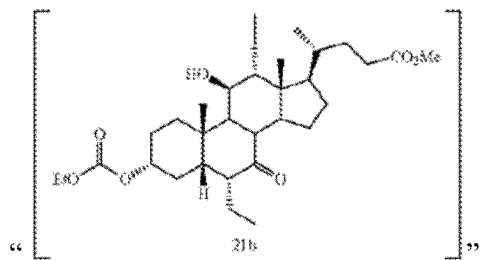

Should read:

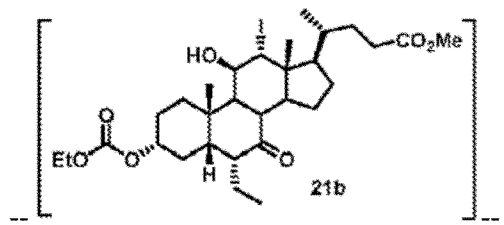

At Column 100, compound structure 21c:

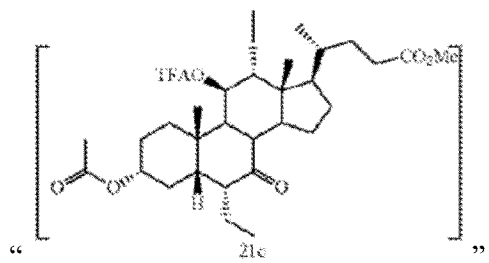

Signed and Sealed this
Twenty-seventh Day of June, 2023

Katherine Kelly Vidal
*Director of the United States Patent and Trademark Office*

CERTIFICATE OF CORRECTION (continued)
U.S. Pat. No. 11,066,437 B2

Page 2 of 4

Should read:

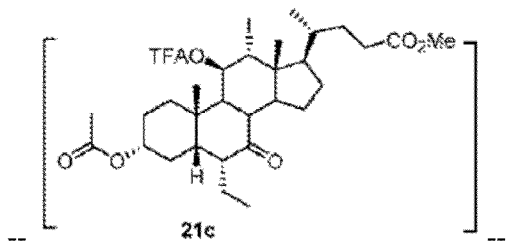

At Column 101, compound structure 21a:

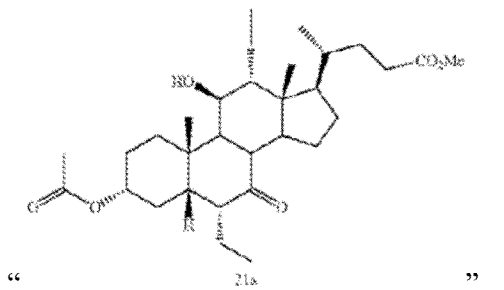

" "

Should read:

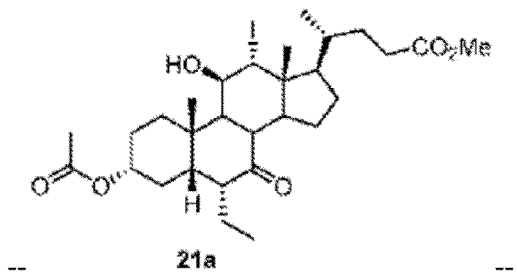

At Column 101, compound structure 21b:

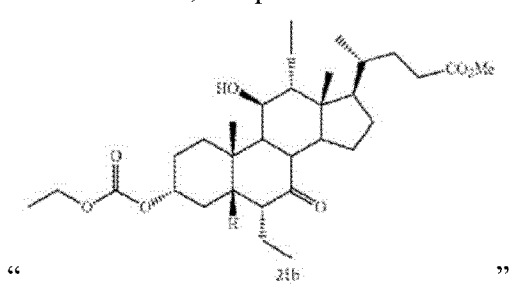

" "

Should read:

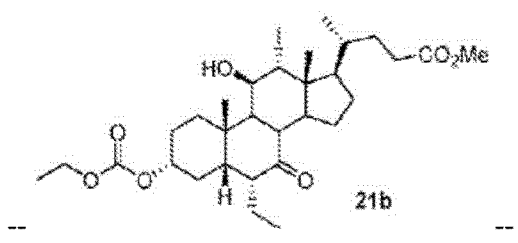

At Column 109, compound structure 21a:
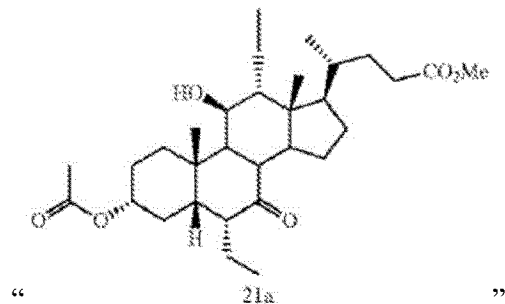
" 21a "
Should read:
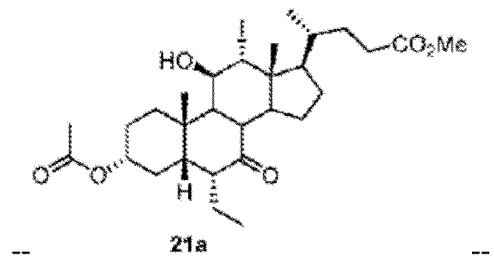
-- 21a --
At Column 110, compound structure 21b:
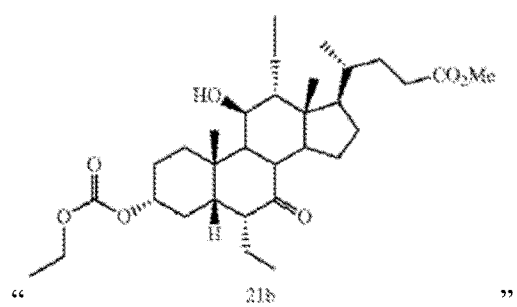
" 21b "
Should read:
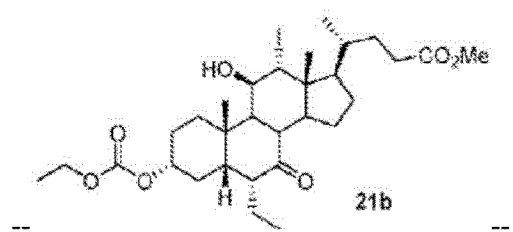
-- 21b --

CERTIFICATE OF CORRECTION (continued)
U.S. Pat. No. 11,066,437 B2

In the Claims

At Column 118, Claim 12, compound structures I-5b and I-5c:

"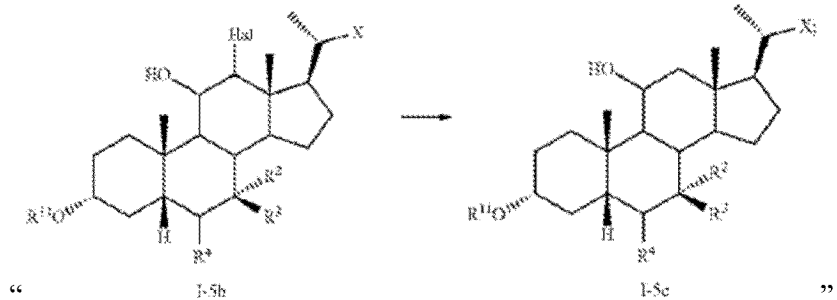"

Should read:

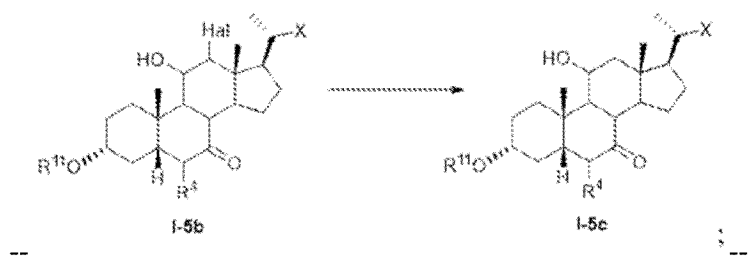
--

At Column 120, Claim 20, compound structure 21b:

"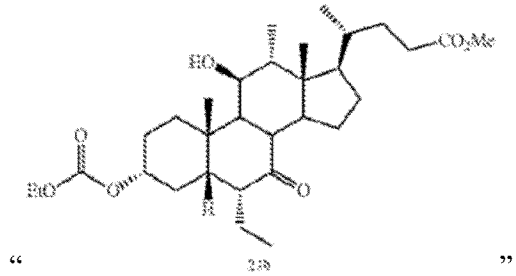"

Should read:

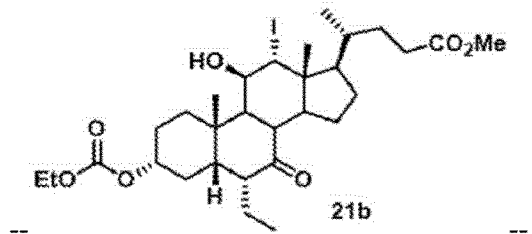
--